(12) United States Patent
Riscoe et al.

(10) Patent No.: US 9,206,131 B2
(45) Date of Patent: Dec. 8, 2015

(54) COMPOUNDS HAVING ANTIPARASITIC OR ANTI-INFECTIOUS ACTIVITY

(71) Applicants: Oregon Health & Science University, Portland, OR (US); The Department of Veterans Affairs, Washington, DC (US); University of South Florida, Tampa, FL (US); Medicines for Malaria Venture, Geneva (CH)

(72) Inventors: Michael K. Riscoe, Tualatin, OR (US); Jane X. Kelly, Lake Oswego, OR (US); Rolf W. Winter, Portland, OR (US); David J. Hinrichs, Lake Oswego, OR (US); Martin J. Smilkstein, Portland, OR (US); Aaron Nilsen, Portland, OR (US); Jeremy Burrows, Eysins (CH); Dennis Kyle, Lithia, FL (US); Roman Manetsch, Tampa, FL (US); Richard M. Cross, Brandon, FL (US); Andrii Monastyrskyi, Tampa, FL (US); David L. Flanigan, Riverview, FL (US)

(73) Assignees: Oregon Health & Science University, Portland, OR (US); The Department of Veterans Affairs, Washington, DC (US); Medicines for Malaria Venture, Geneva (CH); University of South Florida, Tampa, FL (US)

( * ) Notice: Subject to any disclaimer, the term of this patent is extended or adjusted under 35 U.S.C. 154(b) by 0 days.

(21) Appl. No.: 14/055,757

(22) Filed: Oct. 16, 2013

(65) Prior Publication Data
US 2014/0045888 A1 Feb. 13, 2014

Related U.S. Application Data

(60) Division of application No. 13/153,350, filed on Jun. 3, 2011, now Pat. No. 8,598,354, which is a continuation-in-part of application No. PCT/US2009/066841, filed on Dec. 4, 2009.

(60) Provisional application No. 61/201,082, filed on Dec. 5, 2008.

(51) Int. Cl.
C07D 215/233 (2006.01)
C07D 215/42 (2006.01)
(Continued)

(52) U.S. Cl.
CPC .......... C07D 215/233 (2013.01); C07D 215/42 (2013.01); C07D 215/60 (2013.01);
(Continued)

(58) Field of Classification Search
None
See application file for complete search history.

(56) References Cited

U.S. PATENT DOCUMENTS 2,647,901 A 8/1953 Archer
2,709,171 A 5/1955 Stoughton
(Continued)

FOREIGN PATENT DOCUMENTS

DE 551 029 5/1932
EP 0 110 298 6/1984
(Continued)

OTHER PUBLICATIONS

Burckhalter & Mikolasek, Antimalarial agents. IX. 3-Alkylquinolones as Potential Repository Drugs, 56(2) J. Pharma. Sci. 236-9 (1967).*

(Continued)

*Primary Examiner* — Timothy R Rozof
(74) *Attorney, Agent, or Firm* — Klarquist Sparkman, LLP

(57) ABSTRACT

Compounds of formula I:

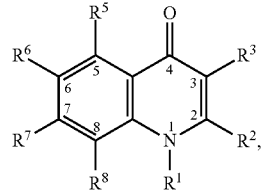

or formula II:

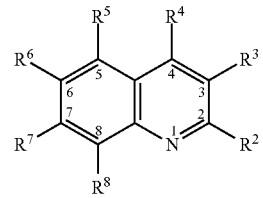

or a pharmaceutically acceptable salt of formula I or formula II, wherein:
$R^1$ is H, hydroxyl, alkoxy, acyl, alkyl, cycloalkyl, aryl, or heteroaryl;
$R^2$ is methyl or haloalkyl;
$R^4$ is hydroxyl, carbonyloxy, or carbonyldioxy; and
$R^3$ is aliphatic, aryl, aralkyl, or alkylaryl; and
$R^5$, $R^6$, $R^7$ and $R^8$ are each individually H, halogen, alkoxy, alkyl, haloalkyl, aryl, nitro, cyano, amino, amido, acyl, carboxyl, substituted carboxyl, or $-SO_2R^{10}$, wherein $R^{10}$ is H, alkyl, amino or haloalkyl;
provided that in formula I, $R^5$ and $R^7$ are not both H or $R^6$ is not H or methoxy; and in formula II that if $R^4$ is carbonyldioxy then $R^7$ is not methoxy.

31 Claims, 42 Drawing Sheets

(51) Int. Cl.

| | |
|---|---|
| C07D 215/60 | (2006.01) |
| C07D 239/90 | (2006.01) |
| C07D 279/16 | (2006.01) |
| C07D 401/04 | (2006.01) |
| C07D 401/06 | (2006.01) |
| C07D 401/12 | (2006.01) |
| C07D 403/04 | (2006.01) |
| C07D 403/06 | (2006.01) |
| C07D 413/04 | (2006.01) |
| C07D 491/052 | (2006.01) |

(52) U.S. Cl.
CPC ............ *C07D239/90* (2013.01); *C07D 279/16* (2013.01); *C07D 401/04* (2013.01); *C07D 401/06* (2013.01); *C07D 401/12* (2013.01); *C07D 403/04* (2013.01); *C07D 403/06* (2013.01); *C07D 413/04* (2013.01); *C07D 491/052* (2013.01)

(56) References Cited

U.S. PATENT DOCUMENTS

| | | |
|---|---|---|
| 2,732,373 A | 1/1956 | Steiger |
| 2,732,374 A | 1/1956 | Steiger |
| 3,636,216 A | 1/1972 | Baron et al. |
| 3,981,903 A | 9/1976 | Hirano et al. |
| 4,250,182 A | 2/1981 | Gorvin |
| 5,656,643 A | 8/1997 | Spada et al. |
| 5,977,077 A | 11/1999 | Winter et al. |
| 6,248,891 B1 | 6/2001 | Sharp et al. |
| 6,541,483 B2 | 4/2003 | Michejda et al. |
| 6,613,797 B2 | 9/2003 | Winter et al. |
| 6,645,983 B1 | 11/2003 | Joseph et al. |
| 6,686,469 B2 | 2/2004 | Eberle et al. |
| 6,703,388 B2 | 3/2004 | Miyamoto et al. |
| 7,109,338 B2 | 9/2006 | Tamura et al. |
| 7,579,353 B2 | 8/2009 | Fiandor Roman et al. |
| 7,829,578 B1 | 11/2010 | Riscoe et al. |
| 2002/0055644 A1 | 5/2002 | Winter et al. |
| 2004/0087618 A1 | 5/2004 | Yamamoto et al. |
| 2010/0130546 A1 | 5/2010 | Otsubo et al. |
| 2010/0196476 A1 | 8/2010 | Correa et al. |

FOREIGN PATENT DOCUMENTS

| | | |
|---|---|---|
| EP | 0 332 033 | 9/1989 |
| EP | 0 878 194 | 11/1998 |
| EP | 1 386 914 | 2/2004 |
| WO | WO 2005/058834 | 6/2005 |
| WO | WO 2008/064011 A1 | 5/2008 |
| WO | WO 2010/065905 | 6/2010 |

OTHER PUBLICATIONS

Stephen et al., Tetrahydroacridones and related compounds as antimalarial, J.O.C. 1034-9 (1947).*
Salzer et al., A new type of compounds active against avian malaria, 81 Chemische Berichte 12-19 (1948).*
Adams et al., "The Iron Environment in Heme and Heme-Antimalarial Complexes of Pharmacological Interest," *Journal of Inorganic Biochemistry* 63:69-77, 1996.
Ager, A.L. Jr., "Rodent Malaria Models," 68/1, Springer-Verlag, Berlin, 1984.
Ahmed et al., "A new rapid and simple non-radioactive assay to monitor and determine the proliferation of lymphocytes: an alternative to [$^3$H]thymidine incorporation assay," *Journal of Immunological Methods* 170:211-224, 1994.
Ahua et al., "Antileishmanial and antifungal acridone derivatives from the roots of *Thamnosma rhodesica*," *Phytochemistry* 65:963-868, 2004.
Ambroise-Thomas, P., "Antimalarial vaccines. Disappointments and hopes.,"*Bull. Acad. Natl. Med.* 181(8):1637-1650, Nov. 18, 1997. (Abstract only).

Anderson et al., "Parallel synthesis of 9-aminoacridines and their evaluation against chloroquine-resistant *Plasmodium falciparum*," *Bioorganic & Medicinal Chemistry* 14(2):334-343, Jan. 15, 2006.
Atkinson et al., "Ultrastructure of Malaria-Infected Erythrocytes," *Blood Cells* 16:351-368, 1990.
Bastow, K.F., "New Acridone Inhibitors of Human Herpes Virus Replication," *Current Drug Targets—Infectious Disorders* 4(4):323-330, 2004.
Boehme et al., "Beta-Substituted enamines. VII. 3-Amino- and 3-mercapto-4(1H)-quinolones,"*Archiv Der Pharmazie and Berichte Der Deutschen Pharmazeutischen Gesellschaft* 305(2):93-6, 1972.
Bojang et al., "Follow-up of Gambian children recruited to a pilot safety and immunogenicity study of the malaria vaccine SPf66," *Parasite Immunology* 19:579-581, 1997.
Boudreau et al., "Tolerability of prophylactic Lariam® regimens," *Trop. Med. Parasitol.* 44:257-265, 1993.
Brewer et al., "Neurotoxicity in animals due to arteether and artemether," *Transactions of the Royal Society of Tropical Medicine and Hygiene* 88(1):33-36, 1994.
Brewer et al., "Factors Relating to Neurotoxicity or Artemisinin Antimalarial Drugs «Listening to Arteether»," *Me.d Trop.* 58(3):22S-27S, 1998.
Broudy et al., "Moncytes Stimulate Fibroblastoid Bone Marrow Stromal Cells to Produce Multilineage Hematopoietic Growth Factors," *Blood* 65(2):530-534, Aug. 1986.
Burckhalter et al., "Antimalarial Agents IX, 3-Alkylquinolones as Potential Repository Drugs," *Journal of Pharmaceutical Sciences* 56(2):236-239, Feb. 1967.
Carter & Mendis, "Evolutionary and Historical Aspects of the Burden of Malaria," *Clinical Microbiology Reviews* 15(4):564-594, Oct. 2002.
Casey, A. "Synthesis of some 4-quinolones and related structures for evaluation as potential antimalarial agents," *University of Bridgeport for Army Medical Research and Development Command*, Nov. 30, 1974.
Casey, "4(1H)-Quinolones. 2. Antimalarial Effect of Some 2-Methyl-3-(1'-alkenyl)-or-3-alkyl-4(1H)-quinolones," *Journal of Medicinal Chemistry* 17:255-256, 1974.
Clark et al., "Developmental Toxicity of Artesunate and an Artesunate Combination in the Rat and Rabbit," *Birth Defects Research (Part B)* 71:380-394, 2004.
Coleman et al., "Gametocytocidal and Sporontocidal Activity of Antimalarials Against *Plasmodium Berghei* Anka in ICR Mice and *Anopheles Stephensi* Mosquitoes," *Am. J. Trop. Med. Hyg.* 46(2):169-182, 1992.
Croft et al., "The activity of hydroxynaphthoquinones against *Leishmania donovani*," *Journal of Antimicrobial Chemotherapy* 30:827-832, 1992.
Doolan et al., "DNA Vaccination as an Approach to Malaria Control: Current Status and Strategies," *Curr. Top. Microbiol. Immunol.* 226:37-56, 1998.
Fidock et al., "Antimalarial Drug Discovery: Efficacy Models for Compound Screening," *Nature Reviews* 3:509-520, Jun. 2004.
Fivelman et al., "Modified Fixed-Ratio Isobologram Method for Studying In Vitro Interactions between Atovaquone and Proguanil or Dihydroartemisinin against Drug-Resistant Strains of *Plasmodium falciparum*," *Antimicrobial Agents and Chemotherapy* 48(11):4097-4102, Nov. 2004.
Fujioka et al., "Activities of New Acridone Alkaloid Derivatives against Plasmodium yoelii in vitro,"*Arzneim-Forsch/Drug Res.* 40(11):1026-1029, 1990.
Fusetti et al., "Meflochina ed ototossicita: descrizione di tre casi," *Clin Ter* 150:379-382, 1999 (Abstract only).
Guillouzo, André, "Liver Cell Models in in Vitro Toxicology," *Environmental Health Perspectives* 106(7):511-532, Apr. 1998.
Hudson et al., "566C80: A Potent Broad Spectrum Anti-Infective Agent with Activity Against Malaria and Opportunistic Infections in AIDS Patients," *Drugs Exptl. Clin. Res.* 17(9):427-435, 1991.
Hudson, A.T., "Atovaquone—A Novel Broad-spectrum Anit-infective Drug," *Parasitology Today* 9(2):66-68, 1993.
Ignatushchenko et al., "Xanthones as antimalarial agents; studies of a possible mode of action," *FEBS Letters* 409:67-73, 1997.

(56) References Cited

OTHER PUBLICATIONS

Ignatushchenko et al., "Xanthones as Antimalarial Agents: Stage Specificity," *Am. J. Trop. Med. Hyg.* 62(1):77-81, 2000.

Kelly et al., "A spectroscopic investigation of the binding interactions between 4,5-dihydroxyxanthone and heme," *Journal of Inorganic Biochemistry* 86:617-625, 2001.

Kelly et al., "Optimization of Xanthones for Antimalarial Activity: the 3,6-Bis-ω -Diethylaminoalkoxyxanthone Series," *Antimicrobial Agents and Chemotherapy* 46(1):144-150, Jan. 2002.

Kelly et al., "The kinetics of uptake and accumulation of 3,6-bis-ω -diethylamino-amyloxyxanthone by the human malaria parasite *Plasmodium falciparum*," *Molecular & Biochemical Parasitology* 123:47-54, 2002.

Kelly et al., "Orally Active Acridones as Novel and Potent Antimalarial Chemotypes," Abstract, *ASTMH 55th Annual Meeting*, Atlanta, Georgia, 1 page (Nov. 12-16, 2006).

Kelly et al., "Structure-Activity Relationships of Orally Active Antimalarial Acridones: Synthesis, Optimization, and Biological Activity," Abstract, ASTMH 55th *Annual Meeting*, Atlanta, Georgia, 1 page (Nov. 12-16, 2006).

Kessl et al., "Molecular Basis for Atovaquone Resistance in *Pneumocystis jirovecii* Modeled in the Cytochrome $bc_1$ Complex of *Saccharomyces cerevisiae*," *The Journal of Biological Chemistry* 279(4): 2817-2824, Jan. 23, 2004.

Kessl et al., "Cytochrome *b* Mutations That Modify the Ubiquinol-binding Pocket of the Cythochrome $bc_1$ Complex and Confer Antimalarial Drug Resistance in *Saccharomyces cerevisiae*," *The Journal of Biological Chemistry* 280(17):17142-17148, Feb. 17, 2005.

Korsinczky et al., "Mutations in *Plasmodium falciparum* Cytochrome *b* That Are Associated with Atovaquone Resistance Are Located at a Putative Drug-Binding Site," *Antimicrobial Agents and Chemotherapy* 44(8):2100-2108, Aug. 2000.

Krungkrai, J., "The multiple roles of the mitochondrion of the malarial parasite," *Parasitology* 129:511-524, 2004.

Kuznetsov et al., "Approaches for introducing high molecular diversity in scaffolds: fast parallel synthesis of highly substituted 1H-quinolin-4-one libraries," *Molecular Diversity* 8(4):437-448, 2004.

Kyle et al., "Antimalarial Activity of 4(1H)-Quinolones," *American Society of Tropical Medicine and Hygiene 54th Annual Meeting*, Washington, D.C., USA, Dec. 11-15, 2005.

Learngaramkul et al., "Molecular Characterization of Mitochondria in Asexual and Sexual Blood Stages of *Plasmodim falciparum*," *Molecular Cell Biology Research Communications* 2:15-20, 1999.

Li et al., "Cryopreserved human hepatocytes: characterization of drug-metabolizing enzyme activities and applications in higher throughput screening assays for hepatotoxicity, metabolic stability, and drug-drug interaction potential," *Chemico-Biological Interactions* 121:17-35, 1999.

Low, Lawrence K., "Metabolic Changes of Drugs and Related Organic Compounds," Chapter 3, pp. 43-122 in J. N. Delgado and WA. Remers (ed.), *Wilson and Gisvold's Textbook of Organic Medicinal and Pharmaceutical Chemistry, 10th edition*, Raven Publishers, Philadelphia, 1998.

Lowden & Bastow, "Cell culture replication of herpes simplex virus and, or human cytomegalovirus is inhibited by 3,7-dialkoxylated, 1-hydroxyacridone derivatives," *Antiviral Research* 59:143-154, 2003.

Luzzi and Peto, "Adverse Effects of Antimalarials; An Update," *Drug Safety* 8(4):295-311, 1993.

Madan et al., "Effect of Cryopreservation on Cytochrome P-450 Enzyme Induction in Cultured Rat Hepatocytes," *Drug Metabolism and Disposition* 27(3):327-335, 1999.

Makler et al., "Detection of *Plasmodium falciparum* Infection with the Fluorescent Dye, Benzothiocarboxypurine," *Am. J. Trop. Med. Hyg.* 44(1):11-16(90-191), 1991.

Massey et al., "Action of nitric acid on polycyclic indole derivatives. XI. Combined addition and substitution," *J. Chem. Soc.* 2218-25, 1931.

Meshnick & Trumpower, "Multiple Cytochrome b Mutations May Cause Atovaquone Resistance," *JID Correspondence* 191:822-823, Mar. 1, 2005.

Michael, Joseph P., "Quinoline, quinazoline and acridone alkaloids," *Nat. Prod. Rep.* 18:543-559, 2001.

Michael, Joseph P., "Quinoline, quinazoline and acridone alkaloids," *Nat. Prod. Rep.* 20:476-493, 2003 (published online Aug. 19, 2003).

Milhous, W.K., "Development of New Drugs for Chemoprophylaxis of Malaria," *Med. Trop.* 61:48-50, 2001.

Mullock et al., "Synthetic uses of polyphosphoric acid and its ethyl ester. II. Syntheses of indolin-2(3H)-one and imidazoquinolines," *J. Chem. Soc.* 2218-25, 1931.

Nishiwaki et al., "Heterocyclizations of 2-aryl-3-arylamino-4,4,4,-trifluoro-2-butenenitrile hydrates to 3-aryl-2-trifluoromethyl-4-quinolones and to 4-N-methylamino-3H-pyrazole-3-spiro-2'-(3-arly-3'-trifluoromethyl)oxiranes," *J. Fluorine Chem.* 73(1):41-6, 1995.

Oettmeier et al., "Acridones and quinolones as inhibitors of ubiquinone functions in the mitochondrial respiratory chain," *Biochem Soc Trans.* 22:213-216, 1994.

Oettmeier et al., "Inhibition of electron transport through the $Q_p$ site in cytochrome $b/c_1$ complexes by acridones," *Biochimica et Biophysica Acta* 1188:125-130, 1994.

O1liaro & Yuthavong, "An Overview of Chemotherapeutic Targes for Antimalarial Drug Discovery," *Pharmacol. Ther.* 81(2):91-110, 1999.

Pessina et al., "In Vitro Tests for Haematotoxicity: Prediction of Drug-induced Myelosuppression by the CFU-GM Assay," *ATLA* 30(Supplement 2):75-79, 2002.

Pessina et al., "Application of the CFU-GM Assay to Predict Acute Drug-Induced Neutropenia: An International Blind Trial to Validate a Prediction Model for the Maxium Tolerated Dose (MTD) of Myelosuppressive Xenobiotics," *Toxicological Sciences* 75:355-367, 2003.

Peters et al., "The chemotherapy of rodent malaria, XXIII," *Annals of Tropical Medicine and Parasitology* 69(3):311-328, 1975.

Phillips-Howard & ter Kuile, "CNS Adverse Events Associated With Antimalarial Agents," *Drug Safety* 12(6):370-383, 1995.

Raether & Fink, "Antimalarial activity of Floxacrine (HOE 991) I; Studies on blood schizontocidal action of Floxacrine against *Plasmodium berghei, P. vinckei and P. cynomologi*," *Annals of Tropical Medicine and Parasitology* 73(6):505-526, 1979.

Raether & Mehlhom, "Action of a New Floxacrine Derivative (S 82 5455) on Asexual Stages of Plasmodium berghei: A Light and Electron Microscopical Study," *Zbl. Bakt. Hyg.* A256:335-341, 1984.

Rathbun et al., "Interferon-γ-induced apoptotic responses of Fanconi anemia group C hematopoietic progenitor cells involve caspase 8-dependent activation of caspase 3 family members," *Blood* 96(13):4204-4211, Dec. 15, 2000.

Riscoe et al., "Evaluation and Lead Optimization of Antimalarial Aromatic Ketones," Abstract, *ASTMH 55th Annual Meeting*, Atlanta, Georgia, 1 page (Nov. 12-16, 2006).

Sachs & Malaney, "The economic and social burden of malaria," *Nature* 415:680-685, Feb. 7, 2002.

Salzer et al., "Über eine neuen, gegen Vogelmalaria wirksamen Verbindungstypus," *Chem. Ber.* 81:12-19, 1948.

Schmidt, L.H., "Antimalarial Properties of Floxacrine, a Dihydroacridinedione Derivative," *Antimicrobial Agents and Chemotherapy* 16(4):475-485, Oct. 1979.

Singh & Puri, "Interaction between chloroquine and diverse pharmacological agents in chloroquine resistant *Plasmodium yoelii migeriensis*," *Acta Tropica* 77:185-193, 2000.

Slomianny & Prensier, "A Cytochemical Ultrastructural Study of the Lysosomal System of Different Species of *Malaria Parasites*," *J. Protozool.* 37(6):465-470, Nov. 1990.

Smilkstein et al., "Simple and Inexpensive Fluorescence-Based Technique for High-Throughput Antimalarial Drug Screening," *Antimicrobial Agents and Chemotherapy* 48(5):1803-1806, May 2004.

Smilkstein et al., "Novel Antimalarial Acridone Derivatives with Both Intrinsic Potency and Synergy with Selected Quinolines: In Vitro and In Vivo Studies," Abstract, *ASTMH 55th Annual Meeting*, Atlanta, Georgia, 1 page (Nov. 12-16, 2006).

(56) References Cited

OTHER PUBLICATIONS

Srivastava et al., "Atovaquone, a Broad Spectrum Antiparasitic Drug, Collapses Mitochondrial Membrane Potential in a Malarial Parasite," *The Journal of Biological Chemistry* 272(7):3961-3966, 1997.
Srivastava et al., "Resistance mutations reveal the atovaquone-binding domain of cytochrome *b* in malaria parasites," *Molecular Microbiology* 33(4):704-711, 1999.
Suswam et al., "*Plasmodium falciparum*: The Effects of Atovaquone Resistance on Respiration," *Experimental Parasitology* 98:180-187, 2001.
Taylor & White, "Antimalarial Drug Toxicity; A Review," *Drug Safety* 27(1):25-61, 2004.
Toovey & Jamieson, "Audiometric changes associated with the treatment of uncomplicated falciparum malaria with co-artemether," *Transactions of the Royal Societ of Tropical Medicine and Hygiene* 98:261-267, 2004.
Trouiller & olliaro, "Drug Development Output from 1975 to 1996: What Proportion for Tropical Diseases?" *Lancet* 354:164-166, 1999.
Trouiller & olliaro, "Drug development output: what proportion for tropical diseases?" *Lancet* 354:164-165, 1999.
Turker, M., "Estimation of mutation frequencies in normal mammalian cells and the development of cancer," *Cancer Biology* 8:407-419, 1998.
Vaidya & Mather, "Atovaquone resistance in malaria parasites," *Drug Resistance Updates* 3:283-287, 2000.
Vaidya, A., "Mitochondrial Physiology as a Target for Atovaquone and Other Antimalarials," I. Sherman (ed.), *Malaria: Parasite Biology, Pathogenesis, and Protection, American Society for Microbiology*, Washington, D.C. 355-368, 1996.
Varney et al., "Long-Term Neuropsychological Sequelae of Fever Associated with Amnesia," *Archives of Clinical Neuropsychology* 9(4):347-352, 1994.
Varney et al., "Neuropsychiatric Sequelae of Cerebral Malaria in Vietnam Veterans," *The Journal of Nervous and Mental Disease* 185(11):695-703, 1997.
Via et al., "Effects of cytokines on mycobacterial phagosome maturation," *Journal of Cell Science* 111:897-905, Mar. 9, 1998.

Weina, P., "From Atabrine in World War II to Mefloquine in *Somalia*: The Role of Education in Preventative Medicine," *Military Medicine* 163(9):635-639, 1998.
White et al., "Averting a malaria disaster," *The Lancet* 353:1965-1967, Jun. 5, 1999.
White, N., "Antimalarial drug resistance," *The Journal of Clinical Investigation* 113(8):1084-1092, Apr. 2004.
Williams, R. B., "The Mode of Action of Anticoccidial Quinolones (6-Decyloxy-4-hydroxyquinoline-3-carboxylates) in Chickens," *International Journal for Parasitology* 27(1):101-111, 1997.
Winkelmann & Raether, "Antimalarial and Anticoccidial Activity of 3-Aryl-7-chloro-3,4-dihydroacridine-1,9-(2H,10H)-diones," *Arzneim-Forsch./Drug Res.* 37(1):647-661, 1987.
Winter et al., "Hydroxy-Anthraquinones as Antimalarial Agents," *Bioorganic & Medicinal Chemistry Letters* 5(17):1927-1932, 1995.
Winter et al., "Potentiation of the Antimalarial Agent Rufigallol," *Antimicrobial Agents and Chemotherapy* 40(6):1408-1411, Jun. 1996.
Winter et al., "Potentiation of an Antimalarial Oxidant Drug," *Antimicrobial Agents and Chemotherapy* 41(7):1449-1454, Jul. 1997.
Winter et al., "Evaluation and lead optimization of anti-malarial acridones," *Experimental Parasitology* 114:47-56, 2006.
Winter et al., "Antimalarial quinolones: Synthesis, potency, and mechanistic studies," *Experimental Parasitology* 118:487-497, 2008 (Published online Nov. 7, 2007).
Yeates et al., "Synthesis and Structure-Activity Relationships of 4-Pyridones as Potential Antimalarials," *J. Med. Chem.* 2008(51):2845-2852, 2008.
International Search Reported from International Application No. PCT/US2007/084560, dated Mar. 31, 2008.
International Search Report from International Application No. PCT/US2009/066841, dated Aug. 18, 2010.
Written Opinion of the International Search Report from International Application No. PCT/US2009/066841, dated Aug. 18, 2010.
Non-Final Office action from corresponding U.S. Appl. No. 13/153,347 dated Aug. 2, 2012.
International Search Report and the Written Opinion of the International Searching Authority from related PCT Application No. PCT/US2012/040712 dated Jan. 30, 2013.

* cited by examiner

FIG. 1 General synthesis of 3-substituted-4(1H)-quinolones by the Conrad-Limpach method.

FIG. 2 Chemical synthesis of ELQ-121 via the Conrad-Limpach method.

FIG. 4

Data Table 1. Structure-activity relationship/profile (SAR) of endochin-like quinolones vs. *Plasmodium falciparum* strains *in vitro*.*

| Compound name | Code | MW | Chemical Structure | LogP | IC₅₀ D6 | ID₅₀ Dd2 | Tm90 C2B |
|---|---|---|---|---|---|---|---|
| Endochin (3-Heptyl-7-methoxy-2-methyl-4(1H)-quinolone | ELQ-100 | 287.4 | 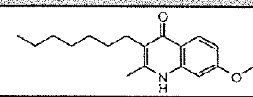 | 3.35 | 3.8 | 3.1 | 11.4 |
| 3-Heptyl-2-methyl-7-trifluoro-methoxy-4(1H)-quinolone | ELQ-102 | 341.4 | 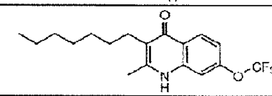 | 5.00 | 85.7 | 85.5 | 102 |
| 7-methoxy-2-methyl-3-(11,11,11-trifluoro-undecyl)-4(1H)-quinolone | ELQ-103 | 397.2 | | 5.31 | 1.2 | 1.4 | 4.7 |
| 7-Methoxy-2-methyl-3-(6,6,6-trifluoro-hexyl)-4(1H)-quinolone | ELQ-104 | 327.3 | 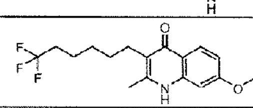 | 3.23 | 56.3 | 53 | 57 |
| 7-Hydroxy-2-methyl-3-(6,6,6-trifluoro-hexyl)-4(1H)-quinolone) | ELQ-105 | 313.3 | 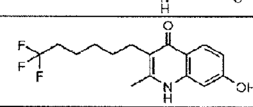 | 2.96 | 6,680 | 390 | 1,360 |
| 3-Heptyl-2-hydroxy-7-methoxy-4(1H)-quinolone | ELQ-106 | 289.4 | 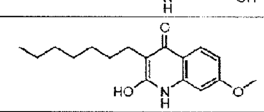 | 3.55 | >2,500 | >2,500 | >2,500 |
| 7-(2-Diethylaminoethoxy)-2-methyl-3-(6,6,6-trifluoro-hexyl) 4(1H) quinolone | ELQ-107 | 412.5 | | 3.90 | 1,800 | 1,500 | 1,300 |
| 3-Hexyl-7-methoxy-2-methyl 4(1H)-quinolone | ELQ-108 | 273.4 | 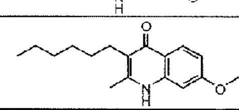 | 2.93 | 6 | 5.5 | 21.4 |
| 7-chloro-3-heptyl-2-methyl-4(1H)-quinolone | ELQ-109 | 291.8 | 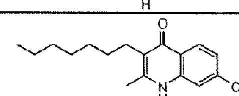 | 4.03 | 5.8 | 2.1 | 63.5 |
| 3-heptyl-2-methyl-7-nitro-4(1H)-quinolone | ELQ-110 | 302.4 | 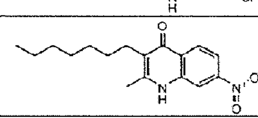 | 4.11 | 18.3 | 21.2 | 40.8 |

FIG. 4 Continued

| | | | | | | |
|---|---|---|---|---|---|---|
| 3-pentyl-7-methoxy-2-methyl-4(1H)-quinolone | ELQ-114 | 259.3 | | 2.52 | 8.1 | 11.9 | 52.0 |
| 3-butyl-7-methoxy-2-methyl-4(1H)-quinolone | ELQ-115 | 245.3 | | 2.10 | 29.1 | 29.3 | 91.8 |
| 3-heptyl-7-hydroxy-2-methyl-4(1H)-quinolone | ELQ-117 | 273.4 | | 3.09 | 759 | 805 | 824 |
| 7-cyano-3-heptyl-2-methyl-4(1H)-quinolone | ELQ-118 | 282.4 | | 3.51 | 17.5 | 44.8 | TBD |
| 4-Chloro-5,7-difluoro-3-heptyl-2-methyl-quinoline | ELQ-119 | 311.8 | | 6.7 | 567 | 455 | 2,625 |
| 7-fluoro-3-heptyl-2-methyl-4(1H)-quinolone | ELQ-120 | 275.4 | | 3.63 | 5.4 | 5.4 | 24.3 |
| 5,7-difluoro-3-heptyl-2-methyl-4(1H)-quinolone | ELQ-121 | 293.3 | | 3.79 | 0.15 | 0.15 | 80.5 |
| 3-(6-Chloro-hexyl)-5,7-difluoro-2-methyl-(4H)-quinolone | ELQ-122 | 313.8 | | 3.4 | 0.81 | 0.37 | 23.6 |
| 5,7-dichloro-3-heptyl-2-methyl-4(1H)-quinolone | ELQ-124 | 326.3 | | 4.59 | 112.2 | 101.4 | 1,700 |
| Carbonic acid 5,7-difluoro-3-heptyl-2-methyl-quinolin-4-yl ester 2-{2-[2-(2-methoxy-ethoxy)-ethoxy]-ethoxy}-ethyl ester | ELQ-125 | 527 | | | 0.4 | 0.4 | 146.1 |
| 3-heptyl-2-methyl-4(1H)-quinolone | ELQ-127 | 257 | | 3.5 | 35.4 | 34.3 | 42.6 |

FIG. 4 Continued

| | | | | | | |
|---|---|---|---|---|---|---|
| 3-heptyl-2-methyl-7-trifluoro-methyl-4(1H)-quinolone | ELQ-129 | 325 | | 4.4 | 216.5 | 179.8 | 7,900 |
| 6-chloro-3-heptyl-2-methyl-4(1H)-quinolone | ELQ-130 | 291.8 | | 4.03 | 18.0 | 12.1 | 15.7 |
| 6-fluoro-3-heptyl-2-methyl-4(1H)-quinolone | ELQ-131 | 275.4 | | 3.63 | 39.9 | 40.0 | 36.9 |
| 6,8-difluoro-3-heptyl-2-methyl-4(1H)-quinolone | ELQ-132 | 293.3 | | 3.79 | 115 | 134 | 110 |
| 3-heptyl-2-methyl-6-methyl-thio-4(1H)-quinolone | ELQ-133 | 303.2 | | 3.92 | 206 | 257 | 461 |
| 5,7-Difluoro-3-heptyl-1,2 dimethyl-4(1H)-quinolone | ELQ-134 | 307.4 | | 4.58 | 25.0 | 20.3 | >2,500 |
| 5-methoxy-2-methyl-3-(6,6,6-trifluoro-hexyl)-4(1H)-quinolone | ELQ-135 | 327.3 | | 3.23 | 1,910 | 1,080 | 1,980 |
| 5-fluoro-3-heptyl-2-methyl-4(1H)-quinolone | ELQ-136 | 275.4 | | 3.63 | <2.5 | <2.5 | 71 |
| 7-Methoxy-2-methyl-3-(3-methyl-butyl)-4(1H)-quinolone | ELQ-137 | 259.3 | | 2.43 | 57.7 | 55.8 | 274.1 |
| 5,7-difluoro-2-methyl-3-(3 methyl butyl)-4(1H)-quinolone | ELQ-138 | 265.3 | | 2.87 | 3.8 | 5.2 | >250 |
| 3-heptyl-2-methyl-5,6,7-trifluoro-quinolone | ELQ-140 | 311.3 | | 3.95 | 1.6 | 1.7 | 23.0 |

FIG. 4 Continued

| | | | | | | |
|---|---|---|---|---|---|---|
| 3-benzyl-5,7-difluoro-2-methyl-4-quinolone | ELQ-141 | 285.3 | | 2.89 | 26.5 | 26.1 | >250 |
| 5,7-Difluoro-3-(4-methoxy-benzyl)- 2-methyl-4-quinolone | ELQ-142 | 315.3 | | 2.77 | 187.7 | 111.7 | >250 |
| 5,7-Difluoro-3-methyl-4(1H)-quinolone | ELQ-144 | 195.1 | | 1.66 | >10,000 | >10,000 | >10,000 |
| 7-methoxy-2-methyl-3-undecyl-4(1H)-quinolone | ELQ-145 | 343.5 | | 5.02 | 1.8 | 1.8 | 2.6 |
| 3-heptyl-2-methyl-6-methane-sulfonyl-4(1H)-quinolone | ELQ-147 | 335.2 | | 2.18 | 79.2 | 97.7 | 211 |
| 5,7-difluoro-2-methyl-3-undecyl-4(1H)-quinolone | ELQ-148 | 349.5 | | 5.46 | 0.89 | 1.09 | 32.7 |
| 5,7-Difluoro-3-{2-[2-(2-methoxy-ethoxy)-ethoxy]-ethyl}-2-methyl-4-(1H)-quinolone | ELQ-149 | 341.3 | | 0.56 | 940 | 932 | 9,800 |
| 3-heptyl-6-methoxy-2-methyl-4(1H)-quinolone | ELQ-150 | 287.4 | | 3.35 | 462 | 481 | 650 |
| 5,7-Difluoro-1,2-dimethyl-3-(3-methyl-butyl)-4(1H)-quinolone | ELQ-151 | 279.3 | | 3.66 | 26.3 | 30.6 | >250 |
| 3-Heptyl-7-methoxy 1,2 dimethyl-4(1H)-quinolone | ELQ-152 | 301.4 | | 4.14 | >250 | >250 | >250 |
| Acetic acid 3-heptyl-7-methoxy-2-methyl-1,4-dihydro-quinolin-4-yl ester | ELQ-153 | 329.4 | | 5.27 | 2.0 | 2.7 | 12.6 |

FIG. 4 Continued

| Name | ID | MW | Structure | | | |
|---|---|---|---|---|---|---|
| 5,7-Difluoro-2-methyl-4(1H)-quinolone | ELQ-154 | 195.2 | | 0.94 | 3,090 | 3,290 | 2,250 |
| 8,10-Difluoro 2,2,5 trimethyl-3,4-dihydro 2H pyrano[3,2-c]quinoline | ELQ-155 | 263.3 | | 3.94 | >2,500 | >2,500 | >2,500 |
| 5,7-Difluoro-3-(6-hydroxy-hexyl)- 2-methyl-4(1H)-quinolone | ELQ-160 | 295.3 | | 2.18 | 17.5 | NT | >250 |
| Acetic acid 6-(5,7-difluoro-2-methyl-4(1H)-quinolin-3-yl)-hexyl ester | ELQ-161 | 337.4 | | 2.41 | 17.2 | 16.7 | >250 |
| 3-Heptyl-2-methyl-6-nitro-4(1H)-quinolone | ELQ-162 | 302.4 | | 4.11 | 59.9 | 59.8 | >250 |
| 3-(6-tert-Butylamino-hexyl)-5,7-difluoro-4(1H)-quinolone | ELQ-163 | 336.4 | | 3.56 | 984 | >250 | >250 |
| 5,7-Difluoro-3-heptyl-4(1H)-quinolone-2-carboxylic acid ethyl ester | ELQ-166 | 351.4 | | 3.67 | 9.8 | 9.1 | 343.2 |
| 5,7-Difluoro-3-heptyl-4(1H)-quinolone-2-carboxylic acid | ELQ-167 | 323.3 | | 3.07 | 202.7 | 207.5 | 1,230 |
| 5,7-Difluoro-3-heptyl-4(1H)-quinolone | ELQ-168 | 279.3 | | 4.17 | 2.3 | 2.7 | 125 |
| 2-methyl-4(1H)-quinolone | ELQ-169 | 159.2 | | 0.62 | >2,500 | >2,500 | >2,500 |

FIG. 4 Continued

| | | | | | | | |
|---|---|---|---|---|---|---|---|
| 3-bromo-2-methyl-4(1H)-quinolone | ELQ-170 | 224.0 | | 0.93 | 241.8 | NT | >2,500 |
| 3-Diethylaminomethyl 2 methyl-4(1H)-quinolone | ELQ-171 | 244.3 | | 1.1 | >2,500 | NT | >2,500 |
| Acetic acid 2-methyl-4(1H)-quinolin-3-yl)methyl ester | ELQ-172 | 231.2 | | 0.14 | >2,500 | NT | >2,500 |
| 4-Oxo-1,4 dihydro quinoline-2-carboxylic acid ethyl ester | ELQ-173 | 217.2 | | 0.5 | >2,500 | >2,500 | >2,500 |
| 3-Bromo-4-oxo-1,4-dihydro-quinoline-2-carboxylic acid ethyl ester | ELQ-174 | 296.1 | | 0.81 | >2,500 | >2,500 | >2,500 |
| 5,7-Difluoro-3-heptyl-4(1H)-quinoline-2-carboxylic acid amide | ELQ-176 | 322.3 | | 2.42 | >2,500 | >2,500 | >2,500 |
| 5,7-Difluoro-3-heptyl-4(1H)-quinoline 2 carboxylic acid (2 diethylamino ethyl)-amide | ELQ-177 | 421.5 | | 3.33 | 840 | 570 | 835 |
| 2-Methyl-3-phenylethynyl-4(1H)-quinolone | ELQ-178 | 259.3 | | 2.43 | 164.3 | 158.2 | 101.2 |
| 2-methyl-3-phenyl-4(1H)-quinolone | ELQ-179 | 235.3 | | 2.16 | 665 | 574 | 215 |
| 5,7-difluoro-4-quinolone-2-ethylester | ELQ-180 | 253.2 | | 0.82 | >2,500 | >2,500 | >2,500 |

FIG. 4 Continued

| | | | | | | | |
|---|---|---|---|---|---|---|---|
| 5,7-difluoro-4-quinolone-2-methylester | ELQ-181 | 239.2 | 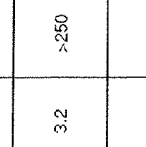 | 0.48 | >2,500 | >2,500 | >2,500 |
| 3-iodo-2-methyl-quinolone | ELQ-182 | 285.1 | | 1.46 | 298 | 518 | 254 |
| 4-butyl-5,7-difluoro-2-methylquinolone | ELQ-183 | 251.3 | 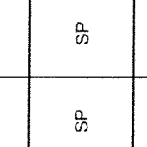 | 2.54 | 6.4 | 3.2 | >250 |
| 5,7-Difluoro-3-heptyl-4(1H)-quinolone-2-carboxylic acid ethylamide | ELQ-184 | 350.4 | 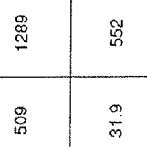 | 2.99 | 319 | 509 | 4,500 |
| 3-Heptyl-1-hydroxy-7-methoxy-2-methyl-4-quinolone | ELQ-185 | 303.4 | 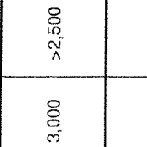 | 3.22 | SP | SP | SP |
| 6-chloro-2-methyl-3-phenyl-4(1H)-quinolone | ELQ-187 | 269.7 | | 2.72 | 470 | 509 | 1289 |
| 5,7-difluoro-2-methyl-3-propyl-4(1H)-quinolone | ELQ-188 | 237.2 | 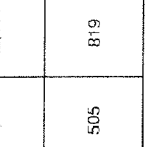 | 2.12 | 23.3 | 31.9 | 552 |
| 3-(4-Chloro-phenyl)-2-methyl-4(1H)-quinolone | ELQ-189 | 269.7 | | 2.72 | 1,500 | 3,000 | >2,500 |
| 2-Methyl-3-p-tolyl-4(1H)-quinolone | ELQ-190 | 249.1 |  | 2.65 | 16,000 | 18,000 | 22,000 |
| 3-(3-chloro-phenyl)-2-methyl-4(1H)-quinolone | ELQ-191 | 269.7 |  | 2.72 | 744 | 505 | 819 |

FIG. 4 Continued

| Name | ID | MW | Structure | | | | |
|---|---|---|---|---|---|---|---|
| 5,7-difluoro-2-methyl-3-phenyl-4(1H)-quinolone | ELQ-192 | 271.3 | 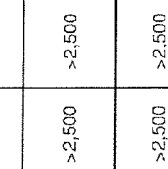 | 2.48 | 127 | 151 | 309 |
| 2-Methyl-3-phenyl-3H-quinazolin-4-one | ELQ-193 | 236.3 | 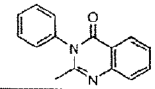 | | >2,500 | >2,500 | >2,500 |
| 3-Butyl-2-methyl-3H-quinazolin-4-one | ELQ-194 | 216.3 | 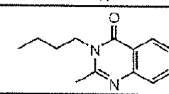 | | >2,500 | >2,500 | >2,500 |
| 5,7-difluoro-3-ethyl-2-methyl-4(1H)-quinolone | ELQ-195 | 223.2 | 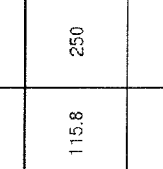 | 1.71 | 86.2 | 115.8 | 250 |
| 3-(2-Diethylamino-ethyl)-2-methyl-3H-quinazolin-4-one | ELQ-196 | 259.4 | 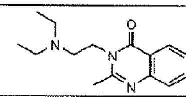 | | >2,500 | >2,500 | >2,500 |
| 7-Chloro-3-(2-diethylamino-ethyl)-2-methyl-3H-quinazolin-4-one | ELQ-197 | 293.8 | 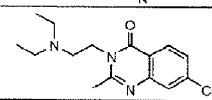 | | >2,500 | >2,500 | >2,500 |
| 5,7-Difluoro-3-heptyl-4(1H)-quinolone-2-carboxylic acid diethylamide | ELQ-198 | 378.5 | 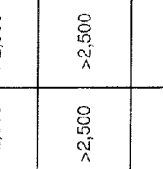 | 3.57 | 1,020 | 1,500 | 18,500 |
| 3-butyl-6-chloro-2-methyl-4(1H)-quinolone | ELQ-200 | 249.8 | 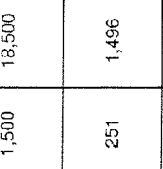 | 2.56 | 154.6 | 251 | 1,496 |
| 6-bromo-3-butyl-2-methyl-4(1H)-quinolone | ELQ-201 | 294.2 | 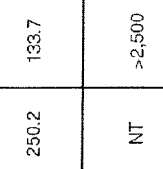 | 3.05 | 189.5 | 250.2 | 133.7 |
| 3-Butyl-6-chloro-4-oxo-1,4-dihydro-quinoline-2-carboxylic acid ethyl ester | ELQ-202 | 307.8 | 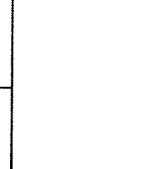 | 2.66 | 1,900 | NT | >2,500 |

FIG. 4 Continued

| | | | | | |
|---|---|---|---|---|---|
| 3-Butyl-6-chloro-4-oxo-1,4-dihydro-quinoline-2-carboxylic acid (4-chloro-phenyl)-amide | ELQ-203 | 389.3 | 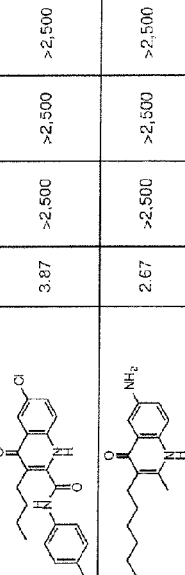 | 3.87 | >2,500 | >2,500 | >2,500 |
| 6-amino-3-heptyl-2-methyl-4(1H)-quinolone | ELQ-204 | 272.4 | 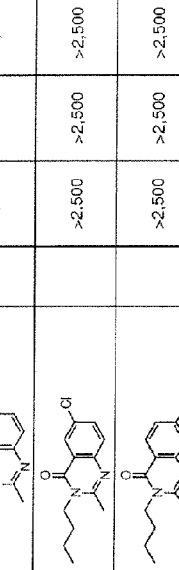 | 2.67 | >2,500 | >2,500 | >2,500 |
| 6-Chloro-3-(2-diethylamino-ethyl)-2-methyl-3H-quinazolin-4-one | ELQ-205 | 293.8 | 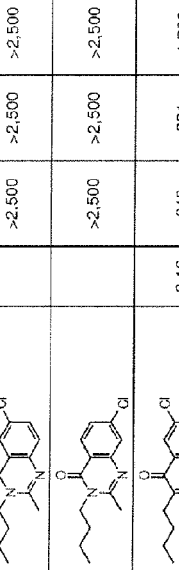 | | >2,500 | >2,500 | >2,500 |
| 3-Butyl-6-chloro-2-methyl-3H-quinazolin-4-one | ELQ-206 | 250.7 | 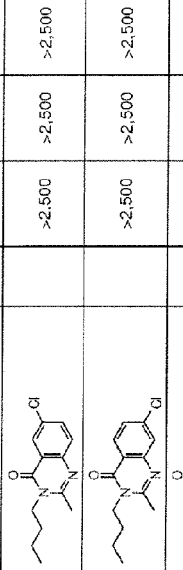 | | >2,500 | >2,500 | >2,500 |
| 3-Butyl-7-chloro-2-methyl-3H-quinazolin-4-one | ELQ-207 | 250.7 | 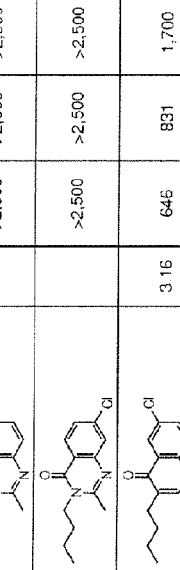 | | >2,500 | >2,500 | >2,500 |
| 3-Butyl-6-chloro-1H-quinolin-4-one | ELQ-208 | 235.7 | 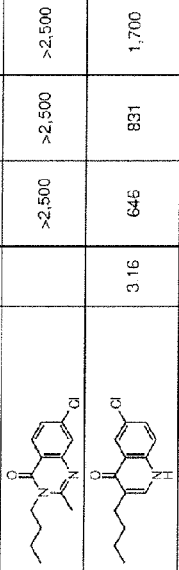 | 3.16 | 646 | 831 | 1,700 |
| 5,7-Difluoro-3-heptyl-2-methyl-4-oxo-quinolone-N-oxide | ELQ-209 | 309.3 | 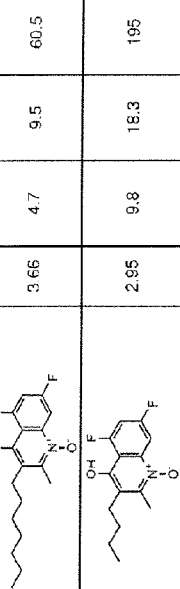 | 3.66 | 4.7 | 9.5 | 60.5 |
| 3-butyl-5,7-Difluoro-2-methyl 4 oxo quinolone-N-oxide | ELQ 210 | 267.3 | 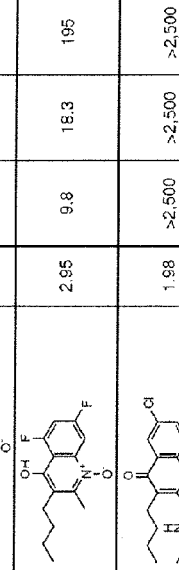 | 2.95 | 9.8 | 18.3 | 195 |
| 3-Butyl-6-chloro-4-(1H)-quinolone-2-carboxylic acid ethylamide | ELQ-216 | 306.8 | 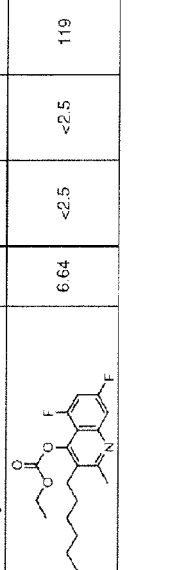 | 1.98 | >2,500 | >2,500 | >2,500 |
| Carbonic acid 5,7-difluoro-3-heptyl-2-methyl-quinolin-4-yl ester ethyl ester | ELQ-217 | 365.4 | 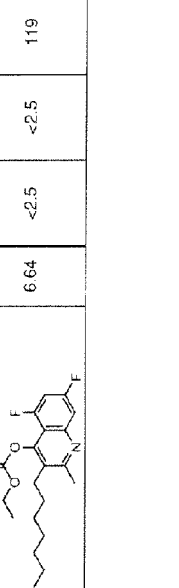 | 6.64 | <2.5 | <2.5 | 119 |

FIG. 4 Continued

| | | | | | | |
|---|---|---|---|---|---|---|
| Carbonic acid 5,7-difluoro-3-heptyl-2-methyl-1-oxy-quinolin-4-yl ester ethyl ester | ELQ-218 | 381.4 | | 5.10 | 17.7 | 33.3 | 86.8 |
| 3-Benzyl-6-chloro-2-methyl-1H-quinolin-4-one | ELQ-220 | 283.7 | | 3.14 | 352 | 393 | 2587 |
| 5,7-Difluoro-3-(3-methoxy-benzyl)-2-methyl-1H-quinolin-4-one | ELQ-223 | 315.3 | | 2.77 | 36.3 | 51.5 | >2,500 |
| 6-Chloro-2-methyl-3-o-tolyl-1H-quinolin-4-one | ELQ-226 | 283.7 | | 3.21 | 302 | 373 | 364 |
| 5,7-Difluoro-3-iodo-2-methyl-1H-quinolin-4-one | ELQ-231 | 321.1 | | 1.78 | 63.9 | 72.2 | 348 |
| 2-Methyl-3-(4-phenoxy-phenyl)-1H-quinolin-4-one | ELQ-233 | 327.4 | | 3.70 | 8.5 | 10.7 | 9.8 |
| 6-Chloro-3-iodo-2-methyl-1H-quinolin-4-one | ELQ-234 | 319.5 | | 2.02 | 145.4 | 164.3 | 190.5 |
| 5,7-Difluoro-2-isopropyl-1H-quinolin-4-one | ELQ-235 | 223.2 | | 1.82 | >2,500 | >2,500 | >2,500 |
| 6-Chloro-2-isopropyl-1H-quinolin-4-one | ELQ-236 | 221.7 | | 2.07 | >2,500 | >2,500 | >2,500 |
| 5,7-Difluoro-3-iodo-2-isopropyl-1H-quinolin-4-one | ELQ-237 | 349.1 | | 2.66 | >2,500 | >2,500 | >2,500 |

FIG. 4 Continued

| | | | | | | | |
|---|---|---|---|---|---|---|---|
| ELQ-238 | 347.6 | 6-Chloro-3-iodo-2-isopropyl-1H-quinolin-4-one | | 2.90 | >2,500 | >2,500 | >2,500 |
| ELQ-239 | 279.3 | 3-Butyl-5,7-difluoro-2-isopropyl-1H-quinolin-4-one | | 3.43 | 488 | 776 | >2,500 |
| ELQ-240 | 277.8 | 3-Butyl-6-chloro-2-isopropyl-1H-quinolin-4-one | | 3.67 | >2,500 | >2,500 | >2,500 |
| ELQ-241 | 295.3 | 5,7-Difluoro-2-methyl-3-phenylethynyl-1H-quinolin-4-one | | 2.74 | 181.8 | 190.4 | 378.1 |
| ELQ-242 | 341.4 | 3-(4-Benzyloxy-phenyl)-2-methyl-1H-quinolin-4-one | | 3.77 | 39.4 | 71.1 | 38.1 |
| ELQ-243 | 341.4 | 3-(3-Benzyloxy-phenyl)-2-methyl-1H-quinolin-4-one | | 3.77 | 258 | 298 | 171 |
| ELQ-244 | 277.3 | 3-(4-Fluoro-phenylethynyl)-2-methyl-1H-quinolin-4-one | | 2.59 | 493.5 | 466.9 | 170.3 |
| ELQ-245 | 302.4 | 3-(4-Dimethylamino-phenylethynyl)-2-methyl-1H-quinolin-4-one | | 2.71 | 424 | 318 | 94.1 |
| ELQ-246 | 293.7 | 3-(4-Chloro-phenylethynyl)-2-methyl-1H-quinolin-4-one | | 2.99 | 480 | 451 | 192 |

FIG. 4 Continued

| Name | ID | MW | Structure | | | | |
|---|---|---|---|---|---|---|---|
| 3-(3-Chloro-phenylethynyl)-2-methyl-1H-quinolin-4-one | ELQ-247 | 293.7 | 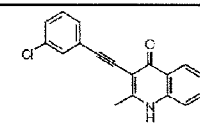 | 2.99 | 481 | 406 | 106 |
| 2-Methyl-3-(4-phenoxy-phenylethynyl)-1H-quinolin-4-one | ELQ-248 | 351.4 | 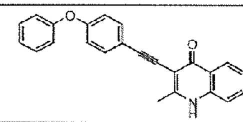 | 3.96 | 84.1 | 90.9 | 23.8 |
| 2-Methyl-3-(4-trifluoromethoxy-phenylethynyl)-1H-quinolin-4-one | ELQ-249 | 343.3 | 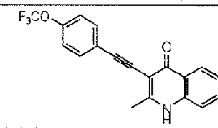 | 3.95 | 74.6 | 66.9 | 14.7 |
| 3-Butyl-6-fluoro-7-methoxy-2-methyl-4(1H)-quinolone | ELQ-250 | 263.3 | 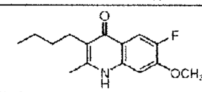 | 2.26 | 30.1 | 30.7 | 30.8 |
| 6-Chloro-3-isopropyl-2-methyl-4(1H)-quinolone | ELQ-251 | 235.7 | 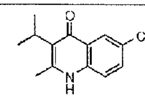 | 2.28 | >2,500 | >2,500 | >2,500 |
| 5,7-Difluoro-3-isopropyl-2-methyl-4(1H)-quinolone | ELQ-252 | 237.2 | 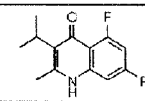 | 2.04 | 69.6 | 95.4 | 1,340 |
| 6-Fluoro-7-methoxy-2-methyl-4(1H)-quinolone | ELQ-253 | 207.2 | 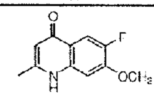 | 0.65 | >2,500 | >2,500 | >2,500 |
| 5,7-Difluoro-2-isopropyl-3-(4-trifluoromethoxyphenylethynyl)-4-(1H)-quinolone | ELQ-254 | 407.3 | | 5.16 | >2,500 | >2,500 | >2,500 |
| 5,7-Difluoro-2-methyl-3-(4-trifluoromethoxy-phenylethynyl)-(1H)-quinolone | ELQ-255 | 379.3 | 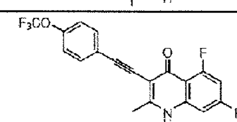 | 4.27 | 9.6 | 17.8 | 87.0 |

FIG. 4 Continued

| | | | | | | |
|---|---|---|---|---|---|---|
| ELQ-256 | 3-Butyl-6-fluoro-2-hydroxymethyl-7-methoxy-4(1H)-quinolone | 279.3 | 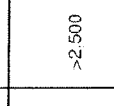 | 1.40 | 707 | 868 | 1,210 |
| ELQ-257 | 5,7-Difluoro-2-methyl-3-(4-phenoxy-phenyl)-4(1H)-quinolone | 363.4 | 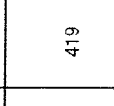 | 4.01 | <2 | <2 | 63.2 |
| ELQ-258 | 6-Fluoro-7-methoxy-2-methyl-3-(4-trifluoro-methoxy-phenylethynyl)-4(1H)-quinolone | 391.3 | 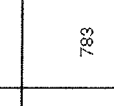 | 3.99 | >2,500 | >2,500 | >2,500 |
| ELQ-259 | 6-Fluoro-7-methoxy-2-methyl-3-pyridin-4-ylethynyl-4(1H)-quinolone | 308.3 | 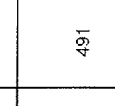 | 1.12 | 343 | 365 | 419 |
| ELQ-260 | 6-Fluoro-7-methoxy-2-methyl-3-pyridin-2-ylethynyl-4(1H)-quinolone | 308.3 | 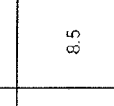 | 1.55 | 1,665 | 1,515 | 783 |
| ELQ-261 | 6-Fluoro-2-methyl-3-(4-trifluoromethoxy-phenylethynyl)-(41H)-quinolone | 361.3 | 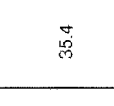 | 4.11 | 422 | 543 | 491 |
| ELQ-262 | 6-Fluoro-7-methoxy-2-methyl-3-(4-phenoxy-phenyl)-4(1H)-quinolone | 375.4 |  | 3.73 | 39.8 | 43.4 | 8.5 |
| ELQ-263 | 3-Biphenyl-4-yl-6-fluoro-7-methoxy-2-methyl-4(1H)-quinolone | 359.4 |  | 3.87 | 122.1 | 141.9 | 35.4 |

FIG. 4 Continued

| Name | ELQ | MW | Structure | | | | |
|---|---|---|---|---|---|---|---|
| 3-Biphenyl-4-yl-6-fluoro-2-methyl-4(1H)-quinolone | ELQ-264 | 329.4 | 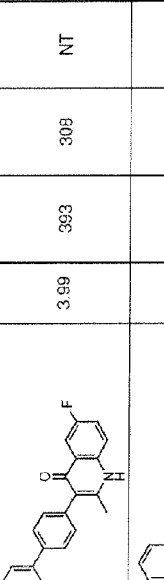 | 3.99 | 393 | 308 | NT |
| 6-Fluoro-7-methoxy-2-methyl-3-(4-trifluoro-methoxy-phenylethynyl)-4(1H)-quinolone | ELQ-265 | 391.3 | 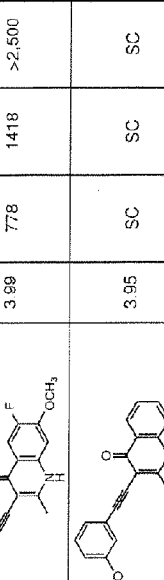 | 3.99 | 778 | 1418 | >2,500 |
| 2-Methyl-3-(3-trifluoromethoxy-phenyl-ethynyl)-4(1H)-quinolone | ELQ-266 | 343.3 | 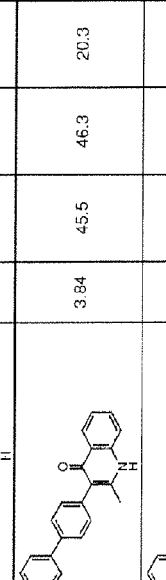 | 3.95 | SC | SC | SC |
| 3-Biphenyl-4-yl-2-methyl-4(1H)-quinolone | ELQ-267 | 311.4 | 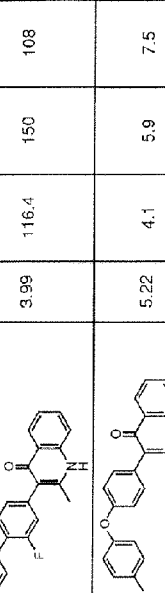 | 3.84 | 45.5 | 46.3 | 20.3 |
| 3-(2-Fluoro-biphenyl-4-yl)-2-methyl-4(1H)-quinolone | ELQ-268 | 329.4 | 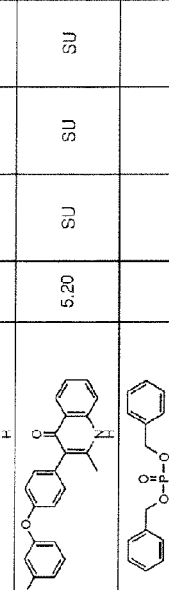 | 3.99 | 116.4 | 150 | 108 |
| 2-Methyl-3-[4-(4-trifluoromethoxy-phenoxy)-phenyl]-4(1H)-quinolone | ELQ-271 | 411.4 | 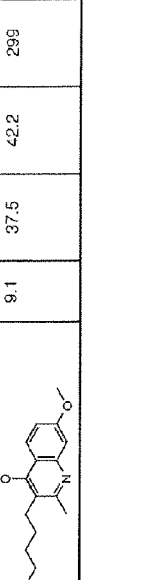 | 5.22 | 4.1 | 5.9 | 7.5 |
| 2-Methyl-3-[4-(3-trifluoromethoxy-phenoxy)-phenyl]-4(1H)-quinolone | ELQ-275 | 411.4 | 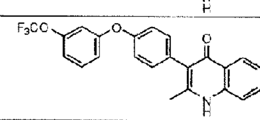 | 5.20 | SU | SU | SU |
| Dibenzoylphospho-4-oxo-endochin | ELQ-276 | 547.6 | 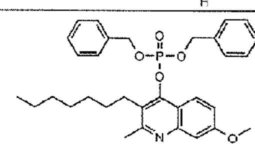 | 9.1 | 37.5 | 42.2 | 299 |

FIG. 4 Continued

| Name | ID | MW | Structure | | | | |
|---|---|---|---|---|---|---|---|
| Endochin-4-oxo-dimethylcarbamate | ELQ-277 | 358.4 | 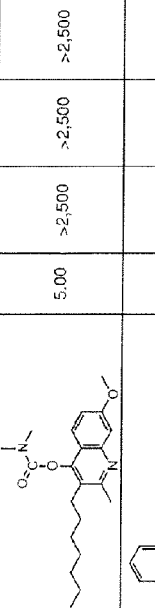 | 5.00 | >2,500 | >2,500 | >2,500 |
| 2-methyl-3-(2-methyl-[1,1'-biphenyl]-4-yl)-quinolin-4(1H)-one | ELQ-278 | 325.4 | 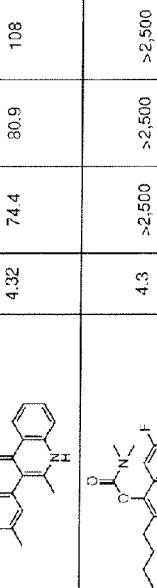 | 4.32 | 74.4 | 80.9 | 108 |
| 3-butyl-6-fluoro-7-methoxy-2-methylquinolin-4-yl dimethylcarbamate | ELQ-279 | 334.4 | 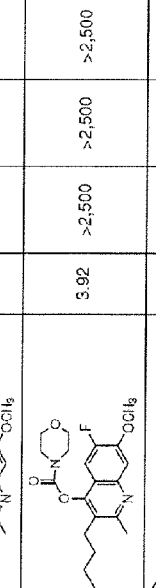 | 4.3 | >2,500 | >2,500 | >2,500 |
| 3-butyl-6-fluoro-7-methoxy-2-methylquinolin-4-yl morpholine-4-carboxylate | ELQ-280 | 376.2 | 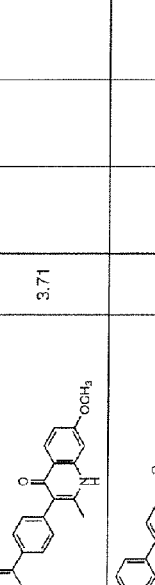 | 3.92 | >2,500 | >2,500 | >2,500 |
| 3-(2-fluoro-6-phenylpyridin-3-yl)-2-methyl-quinolin-4(1H)-one | ELQ-281 | 341.4 | 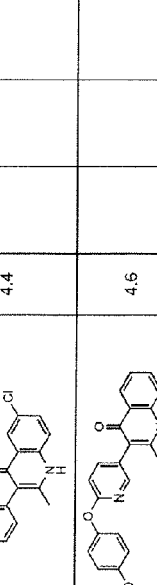 | 3.71 | | | |
| 3-([1,1'-biphenyl]-4-yl)-6-chloro-2-methyl-quinolin-4(1H)-one | ELQ-282 | 345.8 | 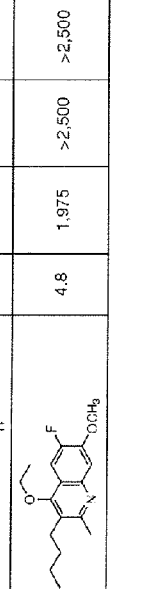 | 4.4 | | | |
| 2-methyl-3-(6-(4-(trifluoromethoxy)phenoxy)-pyridin-3-yl)quinolin-4(1H)-one | ELQ-284 | 412.4 | 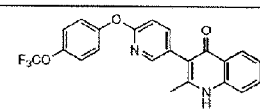 | 4.6 | | | |
| 3-butyl-4-ethoxy-6-fluoro-7-methoxy-2-methylquinoline | ELQ-286 | 291.4 | 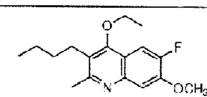 | 4.8 | 1,975 | >2,500 | >2,500 |

FIG. 4 Continued

| | | | | | | |
|---|---|---|---|---|---|---|
| Endochin-4-oxo-dimethylcarbamate | ELQ-277 | 358.4 | (structure) | 5.00 | >2,500 | >2,500 | >2,500 |
| 2-methyl-3-(2-methyl-[1,1'-biphenyl]-4-yl)-quinolin-4(1H)-one | ELQ-278 | 325.4 | (structure) | 4.32 | 74.4 | 80.9 | 108 |
| 3-butyl-6-fluoro-7-methoxy-2-methylquinolin-4-yl dimethylcarbamate | ELQ-279 | 334.4 | (structure) | 4.3 | >2,500 | >2,500 | >2,500 |
| 3-butyl-6-fluoro-7-methoxy-2-methylquinolin-4-yl morpholine-4-carboxylate | ELQ-280 | 376.2 | (structure) | 3.92 | >2,500 | >2,500 | >2,500 |
| 3-(2-fluoro-6-phenylpyridin-3-yl)-2-methyl-quinolin-4(1H)-one | ELQ-281 | 341.4 | (structure) | 3.71 | | | |
| 3-([1,1'-biphenyl]-4-yl)-6-chloro-2-methyl-quinolin-4(1H)-one | ELQ-282 | 345.8 | (structure) | 4.4 | | | |
| 2-methyl-3-(6-(4-(trifluoromethoxy)phenoxy)-pyridin-3-yl)quinolin-4(1H)-one | ELQ-284 | 412.4 | (structure) | 4.6 | | | |
| 3-butyl-4-ethoxy-6-fluoro-7-methoxy-2-methylquinoline | ELQ-286 | 291.4 | (structure) | 4.8 | 1,975 | >2,500 | >2,500 |

FIG. 4 Continued

| | | | | | | | |
|---|---|---|---|---|---|---|---|
| 4-ethoxy-7-methoxy-2-methyl-3-(4-phenoxyphenyl)-1,4-dihydroquinoline | ELQ-287 | 387.5 | 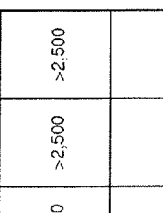 | 4.2 | >2,500 | >2,500 | >2,500 |
| 3-([1,1'-biphenyl]-4-yl)-4-ethoxy-7-methoxy-2-methyl-1,4-dihydroquinoline | ELQ-288 | 371.5 | 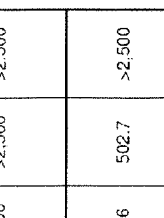 | 4.3 | >2,500 | >2,500 | >2,500 |
| 4-ethoxy-5,7-difluoro-3-heptyl-2-methyl-1,4-dihydroquinoline | ELQ-289 | 323.4 | 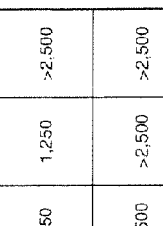 | 4.4 | 432.6 | 502.7 | >2,500 |
| 3-heptyl-2-methyl-6-(trifluoromethoxy)quinolin-4(1H)-one | ELQ-290 | 341.4 | 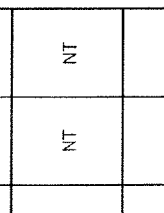 | 5.0 | 1,250 | 1,250 | >2,500 |
| 6-chloro-4-ethoxy-2-methyl-3-(4-(trifluoromethoxy)phenoxy)phenyl)quinoline | ELQ-295 | 473.9 | 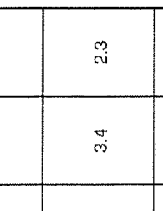 | 8.33 | >2,500 | >2,500 | >2,500 |
| 6-chloro-2-methyl-3-(4-(trifluoromethoxy)phenoxy)phenyl)quinolin-4(1H)-one | ELQ-296 | 445.8 | | 5.78 | 3.2 | NT | NT |
| 4-ethoxy-7-methoxy 2 methyl 3-(4-(trifluoromethoxy)phenoxy)phenyl)quinoline | ELQ-297 | 469.4 | 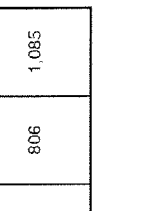 | 7.6 | <2.5* | 2.0* | 2.0* |
| 7-methoxy-2-methyl-3-(4-(trifluoromethoxy)phenoxy)phenyl)quinolin-4(1H)-one | ELQ-298 | 441.4 |  | 5.1 | 1.7 | 3.4 | 2.3 |
| 6-chloro-4-ethoxy-7-methoxy-2-methyl-3-(4-(trifluoromethoxy)phenoxy)phenyl)quinoline | ELQ-299 | 503.9 |  | 8.2 | 703 | 806 | 1,085 |

FIG. 4 Continued

| | | | | | | |
|---|---|---|---|---|---|---|
| 6-chloro-7-methoxy-2-methyl-3-(4-(4-(trifluoromethoxy)phenoxy)phenyl)quinolin-4(1H)-one | ELQ-300 | 475.8 | 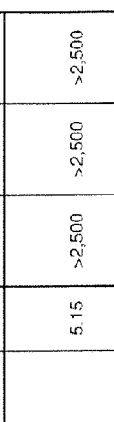 | 5.66 | 0.6 | 0.6 | 0.2 |
| 6-chloro-7-methoxy-2-methyl-3-(4-(4-(trifluoromethoxy)phenoxy)phenyl)quinolin-4-yl dimethylcarbamate | ELQ-301 | 546.9 | 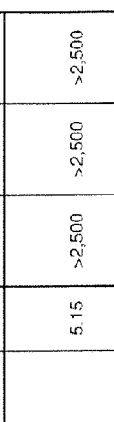 | 7.72 | 450 | 865 | 625 |
| 6-chloro-7-methoxy-2-methyl-3-(o-tolyl)-quinolin-4-yl dimethylcarbamate | ELQ-302 | 384.9 | 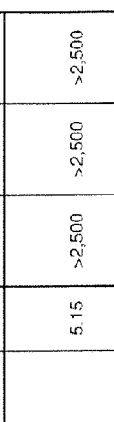 | 5.15 | >2,500 | >2,500 | >2,500 |
| 3-([1,1'-biphenyl]-4-yl)-7-methoxy-2-methylquinolin-4(1H)-one | ELQ-303 | 341.4 | 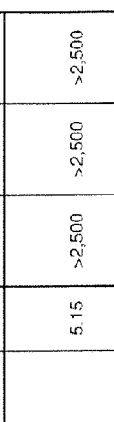 | 3.71 | 17.7 | 16.8 | 16.1 |
| 6-chloro-7-methoxy-2-methyl-3-(4-(4-(trifluoromethoxy)phenoxy)phenyl)quinolin-4-yl morpholine-4-carboxylate | ELQ-304 | 589.0 | 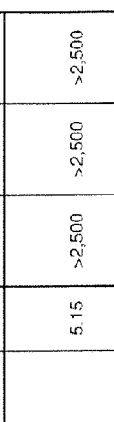 | 7.32 | >2,500 | >2,500 | >2,500 |
| 4-ethoxy-2-methyl-3-(4-(4-(trifluoromethoxy)phenoxy)phenyl)quinoline | ELQ-305 | 439.4 | 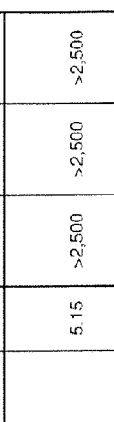 | 7.77 | >2,500 | >2,500 | >2,500 |
| 7-heptyl-6-methyl-[1,3]dioxolo[4,5-g]-quinolin-8(5H)-one | ELQ-306 | 301.4 | 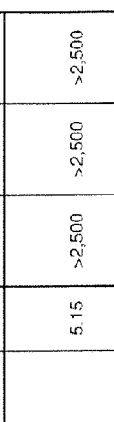 | 3.26 | 27.4 | 25.9 | >2,500 |

FIG. 4 Continued

| | | | | | | | |
|---|---|---|---|---|---|---|---|
| 6-chloro-7-methoxy-2-methyl-3-(4-(3-(trifluoro-methoxy)phenoxy)phenyl)quinolin-4(1H)-one | ELQ-307 | 475.8 | [structure] | 5.66 | 0.03 | 0.03 | <0.03 |
| 6-chloro-7-methoxy-2-methyl-3-(4-(4-(trifluoro-methyl)phenoxy)phenyl)quinolin-4(1H)-one | ELQ-309 | 459.8 | [structure] | 5.05 | 0.3 | 0.3 | 0.05 |
| 6-chloro-7-methoxy-2-methyl-3-(6-(4-(trifluoromethoxy)-phenoxy)pyridin-3-yl)quinolin-4(1H)-one | ELQ-310 | 476.8 | [structure] | 5.04 | 0.3 | 0.2 | 0.4 |
| 3-(4-(benzo[d][1,3]dioxol-5-yloxy)phenyl)-6-chloro-7-methoxy-2-methylquinolin-4(1H)-one | ELQ-311 | 435.9 | [structure] | 3.91 | 3.3 | 3.4 | 1.5 |
| 4-ethoxy-6-fluoro-2-methyl-3-(4-(trifluoromethoxy)phenoxy)phenyl)quinoline | ELQ-312 | 457.4 | [structure] | 7.93 | >2,500 | >2,500 | >2,500 |
| 6-chloro-7-methoxy-2-methyl-3-(5-(4-(trifluoromethoxy)-phenoxy)pyridin-2-yl)quinolin-4(1H)-one | ELQ-313 | 476.8 | [structure] | 4.74 | 0.4 | 0.5 | 0.2 |
| 6-fluoro-2-methyl-3-(4-(4-(trifluoromethoxy)-phenoxy)phenyl)quinolin-4(1H)-one | ELQ-314 | 429.4 | [structure] | 5.38 | 1.5 | 2.4 | 1.7 |
| 4-ethoxy-6-fluoro-7-methoxy-2-methyl-3-(4-(trifluoromethoxy)phenoxy)phenyl)quinoline | ELQ-315 | 487.4 | [structure] | 7.80 | >2,500 | >2,500 | >2,500 |

FIG. 4 Continued

| Name | ID | MW | Structure | | | |
|---|---|---|---|---|---|---|
| 6-fluoro-7-methoxy-2-methyl-3-(4-(4-(trifluoromethoxy)-phenoxy)phenyl)quinolin-4(1H)-one | ELQ-316 | 459.4 | 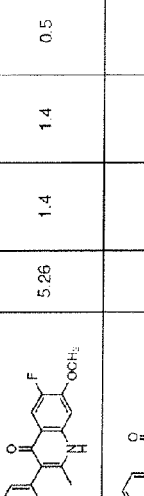 | 5.26 | 1.4 | 1.4 | 0.5 |
| 6-chloro-2-methyl-3-(6-(4-(trifluoromethoxy)-phenoxy)pyridin-3-yl)quinolin-4(1H)-one | ELQ-317 | 446.8 | 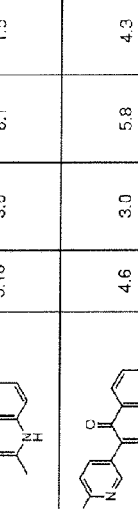 | 5.16 | 3.5 | 6.1 | 1.5 |
| 2-methyl-3-(6-(4-(trifluoromethoxy)phenoxy)pyridin-3-yl)-quinolin-4(1H)-one | ELQ-319 | 412.4 | 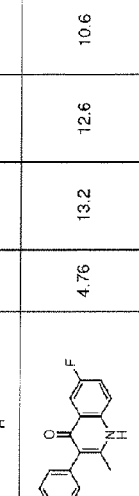 | 4.6 | 3.0 | 5.8 | 4.3 |
| 6-fluoro-2-methyl-3-(6-(4-(trifluoromethoxy)phenoxy)pyridin-3-yl)-quinolin-4(1H)-one | ELQ-320 | 430.3 | 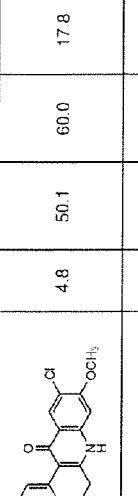 | 4.76 | 13.2 | 12.6 | 10.6 |
| 6-chloro-2-(hydroxymethyl)-7-methoxy-3-(4-(4-(trifluoromethoxy)phenoxy)phenyl)quinolin-4(1H)-one | ELQ-322 | 491.8 | 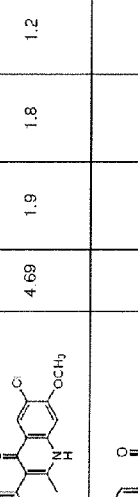 | 4.8 | 50.1 | 60.0 | 17.8 |
| 6-chloro-3-(4-(4-chlorophenoxy)phenyl)-7-methoxy-2-methylquinolin-4(1H)-one | ELQ-323 | 426.3 | 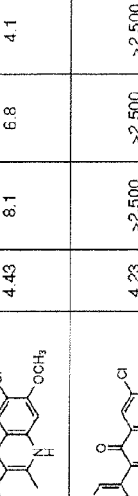 | 4.69 | 1.9 | 1.8 | 1.2 |
| 6-chloro-7-methoxy-2-methyl-3-(4-((5-(trifluoromethyl)pyridin-2-yl)oxy)phenyl)quinolin-4(1H)-one | ELQ-326 | 460.8 | 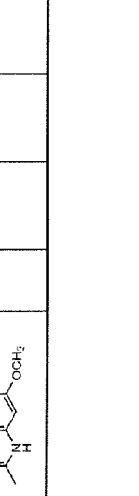 | 4.43 | 8.1 | 6.8 | 4.1 |
| 6-chloro-7-methoxy-2-methyl-3-(2-(4-(trifluoromethoxy)phenoxy)pyrimidin-5-yl)quinolin-4(1H)-one | ELQ-329 | 477.8 |  | 4.23 | >2,500 | >2,500 | >2,500 |

FIG. 4 Continued

| | | | | | | | |
|---|---|---|---|---|---|---|---|
| 6-chloro-3-(4-(hydroxymethyl)phenoxy)-phenyl)-7-methoxy-2-methylquinolin-4(1H)-one | ELQ-332 | 421.9 | | 3.56 | 3.1 | 10.4 | 2.2 |
| 6-chloro-3-(4-(4-fluorophenoxy)phenyl)-7-methoxy-2-methylquinolin-4(1H)-one | ELQ-333 | 409.8 | | 4.29 | 0.8 | 3.8 | NT |
| 6-chloro-7-methoxy-1,2-dimethyl-3-(4-(4-(trifluoro-methoxy)phenoxy)phenyl)quinolin-4(1H)-one | ELQ-335 | 489.9 | | 6.44 | 79.1 | 340 | NT |
| 6-chloro-3-(3-fluoro-4-(4-(trifluoromethoxy)phenoxy)phenyl)-7-methoxy-2-methylquinolin-4(1H)-one | ELQ-351 | 493.8 | | 5.81 | 9.8 | NT | NT |
| 6-chloro-3-(4-(4-fluoro-3-(trifluoromethoxy)phenoxy)phenyl)-7-methoxy-2-methylquinolin-4(1H)-one | ELQ-352 | 493.8 | | 5.81 | 0.45 | NT | NT |
| 6-chloro-3-(4-(3-fluoro-4-(trifluoromethoxy)phenoxy)phenyl)-7-methoxy-2-methylquinolin-4(1H)-one | ELQ-353 | 493.8 | | 5.81 | 18.1 | NT | NT |
| 5,7-difluoro-2-methyl-3-(4-(4-(trifluoromethoxy)phenoxy)-phenyl)quinolin-4(1H)-one | ELQ-400 | 447.3 | | 5.54 | 0.1 | 0.1 | 5 |
| 3-(4-(4-chlorophenoxy)phenyl)-5,7-difluoro-2-methylquinolin-4(1H)-one | ELQ-402 | 397.8 | | 4.57 | 0.6 | 0.6 | NT |

FIG. 4 Continued

| | | | | | | |
|---|---|---|---|---|---|---|
| Chloroquine | CQ | 319.9 | [structure] | 4.72 | 11.2 | 94.0 | 91.7 |
| Atovaquone | ATV | 366.8 | [structure] | 6.2 | 0.1 | 0.1 | 7,700 |

*Results are the average of at least 3 independent determinations, each carried out in triplicate. Testing underway = TU; NT = not tested; SU = Synthesis underway; SC = Synthesis complete; SP = Synthesis planned.

FIG. 5

Data Table 2. Structure-activity relationship/profile (SAR) of endochin-like quinolones vs. *T. gondii* in vitro. Compounds shaded in yellow have been synthesized.*

| Compound name | Code | MW. | Chemical Structure | Log P | IC$_{50}$ nM (T. gondii) | TD$_{50}$ nM (fibroblasts) | IVTI |
|---|---|---|---|---|---|---|---|
| Endochin (3-Heptyl-7-methoxy-2-methyl-4(1H)-quinolone) | ELQ-100 | 287.4 | 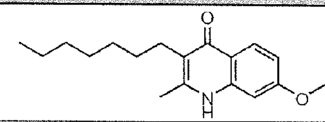 | 3.35 | 0.006 | 1.75x10$^5$ | 2.8x10$^7$ |
| 3-Heptyl-2-methyl-7-trifluoro-methoxy-4(1H)-quinolone | ELQ-102 | 341.4 | 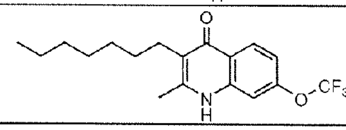 | 5.00 | 4.8 | >3.2 x 10$^5$ | >1.6x10$^4$ |
| 7-methoxy-2-methyl-3-(11,11,11-trifluoro-undecyl-4(1H)-quinolone | ELQ-103 | 397.2 | 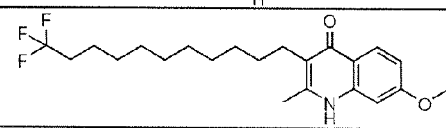 | 5.31 | 0.0004 | 8.1x10$^5$ | 2 X 10$^9$ |
| 7-Methoxy-2-methyl-3-(6,6,6-tri fluoro-hexyl)- 4(1H)-quinolone | ELQ-104 | 327.3 | 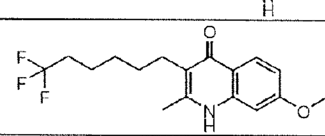 | 3.23 | 11.6 | >9.8x10$^5$ | >8.4x10$^4$ |
| 7-Hydroxy-2-methyl-3-(6,6,6-tri fluoro-hexyl)- 4(1H)-quinolone | ELQ-105 | 313.3 | 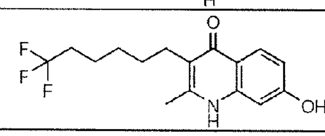 | 2.96 | 6,070 | >1.0x10$^6$ | >168 |
| 3-Heptyl-2-hydroxy-7-methoxy-4(1H)-quinolone | ELQ-106 | 289.4 | 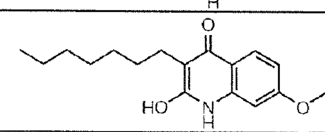 | 3.55 | 25,260 | >1.1x10$^6$ | >44 |

FIG. 5 Continued

| | | | | | | |
|---|---|---|---|---|---|---|
| 7-(2-Diethylaminoethoxy)-2-methyl-3-(6,6,6-trifluorohexyl)-4(1H)-quinolone | ELQ-107 | 412.5 | (structure) | 3.90 | 15,534 | 3.2x10$^4$ | 2.1 |
| 3-Hexyl-7-methoxy-2-methyl-4(1H)-quinolone | ELQ-108 | 273.4 | (structure) | 2.93 | 0.14 | >1.2x10$^6$ | >8.58x10$^6$ |
| 7-chloro-3-heptyl-2-methyl-4(1H)-quinolone | ELQ-109 | 291.8 | (structure) | 4.03 | 0.31 | >1.1x10$^6$ | >3.6x10$^6$ |
| 3-heptyl-2-methyl-7-nitro-4(1H)-quinolone | ELQ-110 | 302.4 | (structure) | 4.11 | 3.3 | >1.1x10$^6$ | >2.8x10$^5$ |
| 3-pentyl-7-methoxy-2-methyl-4(1H)-quinolone | ELQ-114 | 259.3 | (structure) | 2.52 | 1.3 | >1.2x10$^6$ | >9.7x10$^5$ |
| 3-butyl-7-methoxy-2-methyl-4(1H)-quinolone | ELQ-115 | 245.3 | (structure) | 2.10 | 530 | >1.3x10$^6$ | >2.4x10$^3$ |
| 3-heptyl-7-hydroxy-2-methyl-4(1H)-quinolone (desmethyl-endochin) | ELQ-117 | 273.4 | (structure) | 3.09 | 781 | >1.5x10$^5$ | >192 |
| 7-cyano-3-heptyl-2-methyl-4(1H)-quinolone | ELQ-118 | 282.4 | (structure) | 3.51 | 3.5 | >3.2 x 10$^5$ | >9.0x10$^4$ |

FIG. 5 Continued

| | | | | | | |
|---|---|---|---|---|---|---|
| 4-Chloro-5,7-difluoro-3-heptyl-2-methyl-quinoline | ELQ-119 | 311.8 | 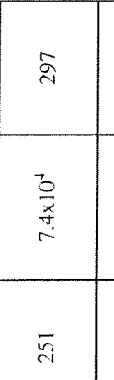 | 6.7 | 251 | 7.4x10⁴ | 297 |
| 7-fluoro-3-heptyl-2-methyl-4(1H)-quinolone | ELQ-120 | 275.4 | 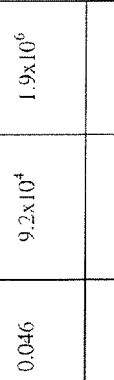 | 3.63 | 0.046 | 9.2x10⁴ | 1.9x10⁶ |
| 5,7-difluoro-3 heptyl-2-methyl-4(1H)-quinolone | ELQ-121 | 293.3 | 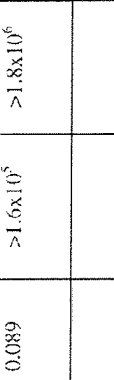 | 3.79 | 0.089 | >1.6x10⁵ | >1.8x10⁶ |
| 5,7-difluoro-3-(ω-chloro-hexyl)-2-methyl-4(1H)-quinolone | ELQ-122 | 327.8 | 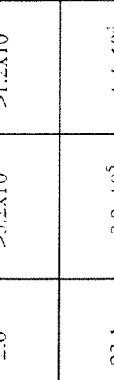 | 3.82 | 2.6 | >3.2x10⁵ | >1.2x10⁵ |
| 5,7-dichloro-3-heptyl-2-methyl-4(1H)-quinolone | ELQ-124 | 326.3 | 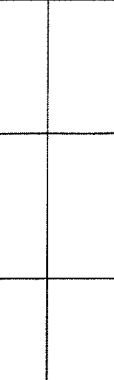 | 4.59 | 23.1 | >3.2x10⁵ | >1.4x10⁴ |
| Carbonic acid 5,7-difluoro-3-heptyl-2-methyl-quinolin-4-yl ester 2-[2-(2-methoxy-ethoxy)-ethoxy]-ethyl ester | ELQ-125 | 527.6 |  | 5.6 | | | |
| 3-heptyl-2-methyl-7-methylthio-4(1H)-quinolone | ELQ-126 | 303.5 | 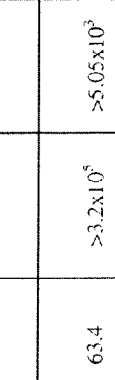 | 3.9 | 63.4 | | |
| 3-heptyl-2-methyl-4(1H)-quinolone | ELQ-127 | 257 |  | 3.5 | | >3.2x10⁵ | >5.05x10³ |

FIG. 5 Continued

| | | | | | | |
|---|---|---|---|---|---|---|
| 7-Methoxy-2-methyl-3-(3-methyl-butyl)-4(1H)-quinolone | ELQ-137 | 259.3 | 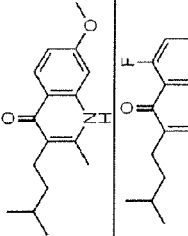 | 2.43 | 5.9 | >3.2x10$^5$ | >9.4x10$^4$ |
| 5,7-difluoro-2-methyl-3-(3-methyl-butyl)-4(1H)-quinolone | ELQ-138 | 265.3 | | 2.87 | 0.015 | >3.2x10$^5$ | >3.8x10$^7$ |
| 5,7-Difluoro-2-methyl-3-(3-methyl-but-2-enyl)-4(1H)-quinolone | ELQ-139 | 263.3 | | 2.40 | ND | ND | ND |
| 3-heptyl-2-methyl-5,6,7-trifluoro-quinolone | ELQ-140 | 311.3 | 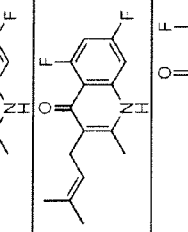 | 3.95 | 0.0002 | >3.2x10$^5$ | 2.8x10$^9$ |
| 3-benzyl-5,7-difluoro-2-methyl-4-quinolone | ELQ-141 | 285.3 | | 2.89 | 4.2 | >3.2x10$^5$ | >1.3x10$^5$ |
| 5,7-Difluoro-3-(4-methoxy-benzyl)-2-methyl-4(1H)-quinolone | ELQ-142 | 315.3 | | 2.77 | 157.2 | >3.2x10$^5$ | >3.5x10$^3$ |
| 5,7-Difluoro-2-methyl-3-pyridin-2-ylmethyl-4(1H)-quinolone | ELQ-143 | 286.3 | | 1.84 | ND | ND | ND |
| 7-methoxy-2-methyl-3-undecyl-4(1H)-quinolone | ELQ-145 | 343.5 | 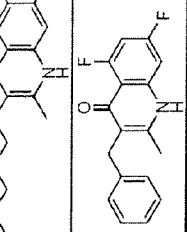 | 5.02 | <0.001 | >3.2x10$^5$ | ND |

FIG. 5 Continued

| | | | | | | |
|---|---|---|---|---|---|---|
| 3-heptyl-2-methyl-6-methane-sulfonyl-4(1H)-quinolone | ELQ-147 | 335.2 | [structure] | 2.18 | ND | ND |
| 5,7-difluoro-2-methyl-3-undecyl-4(1H)-quinolone | ELQ-148 | 349.5 | [structure] | 5.46 | <0.001 | >3.2x10⁵ |
| 5,7-Difluoro-3-[2-[2-(2-methoxy-ethoxy)-ethyl]-2-methyl-4-(1H)-quinolone | ELQ-149 | 341.3 | [structure] | 0.56 | ND | ND |
| 3-heptyl-6-methoxy-2-methyl-4(1H)-quinolone | ELQ-150 | 287.4 | [structure] | 3.35 | 5.8 | >3.2x10⁵ |
| Pyrimethamine | PYR | 248.7 | | 3.14 | 880 | 85,500 |
| Trimethoprim | TMP | 290.3 | | 1.43 | 18,300 | 220,290 |
| Sulfamethoxazole | SMX | 255.3 | | 0.9 | 32,000 | 1,250,000 |
| Atovaquone | ATV | 366.8 | | 3.68 | 220 | 18,530 |

| |
|---|
| ND |
| |
| ND |
| >9.8x10⁻¹ |
| 97 |
| 12 |
| 39 |
| 84.2 |

FIG. 9
Examples of 3-position alkyls.
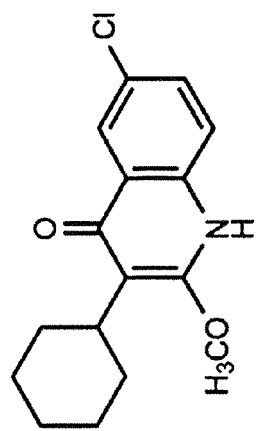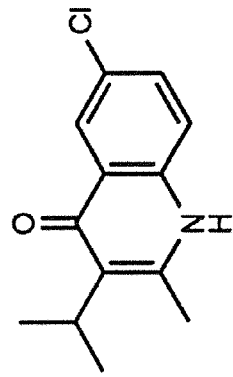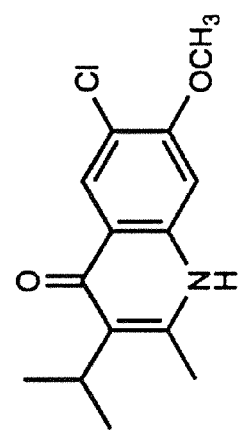
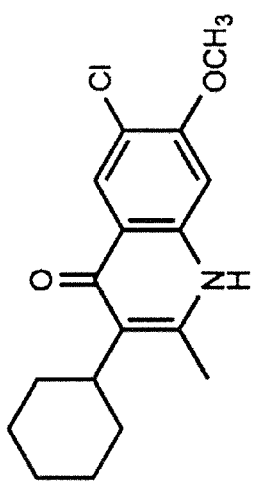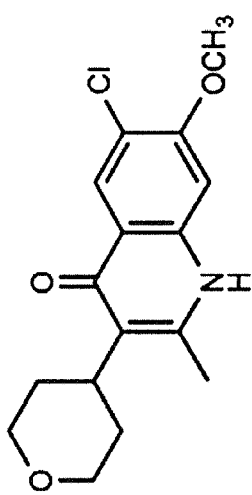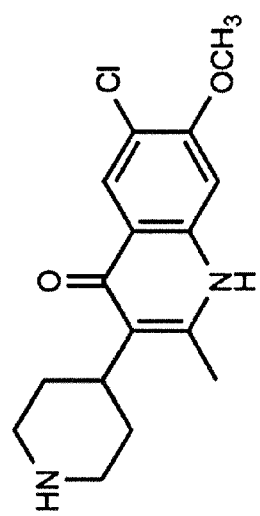
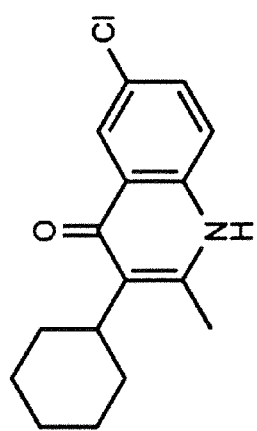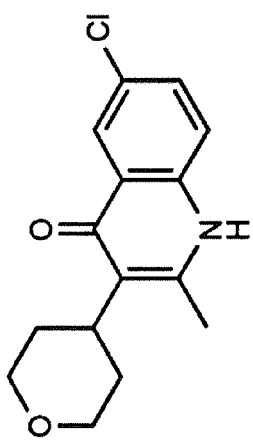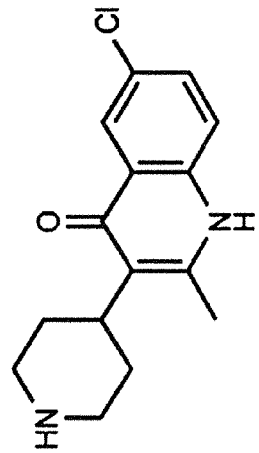

FIG. 10 Aryl-acetylene ELQ derivatives

FIG. 11
Examples of 3-position aryl/phenyl ELQs
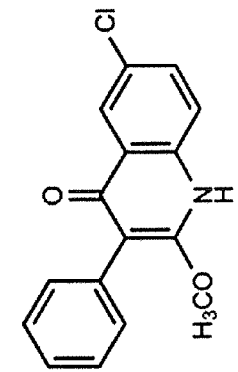
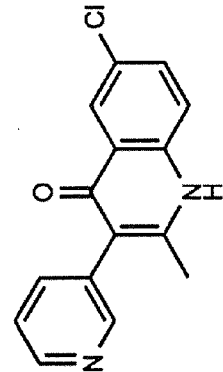
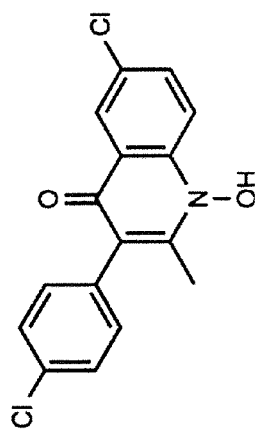
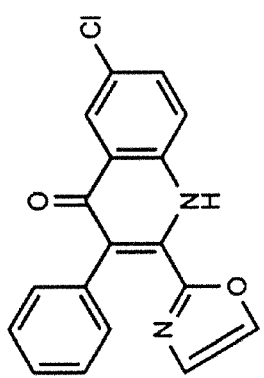
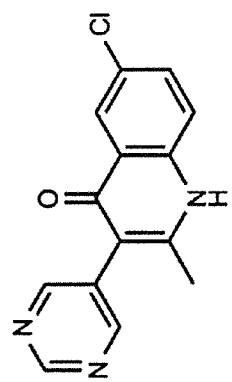
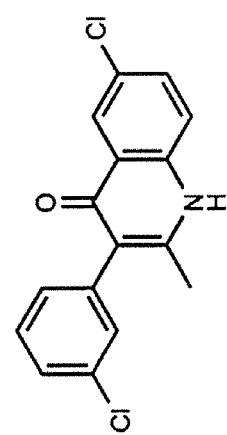
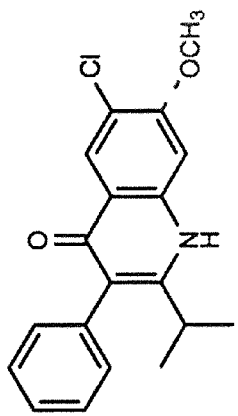
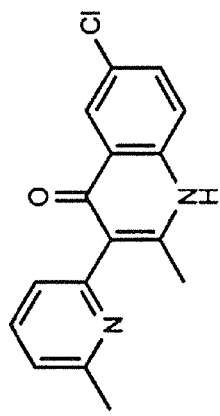
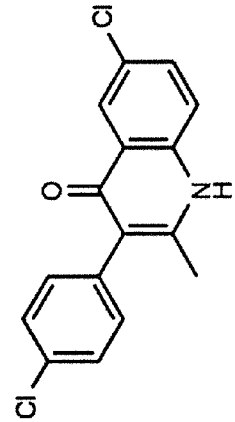

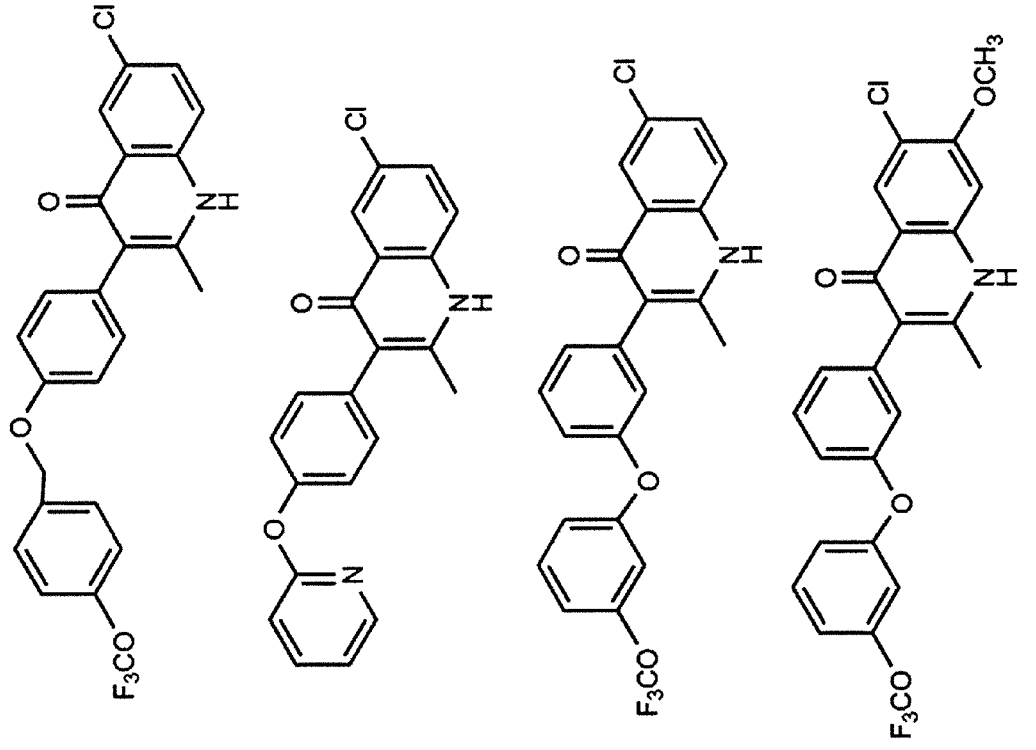
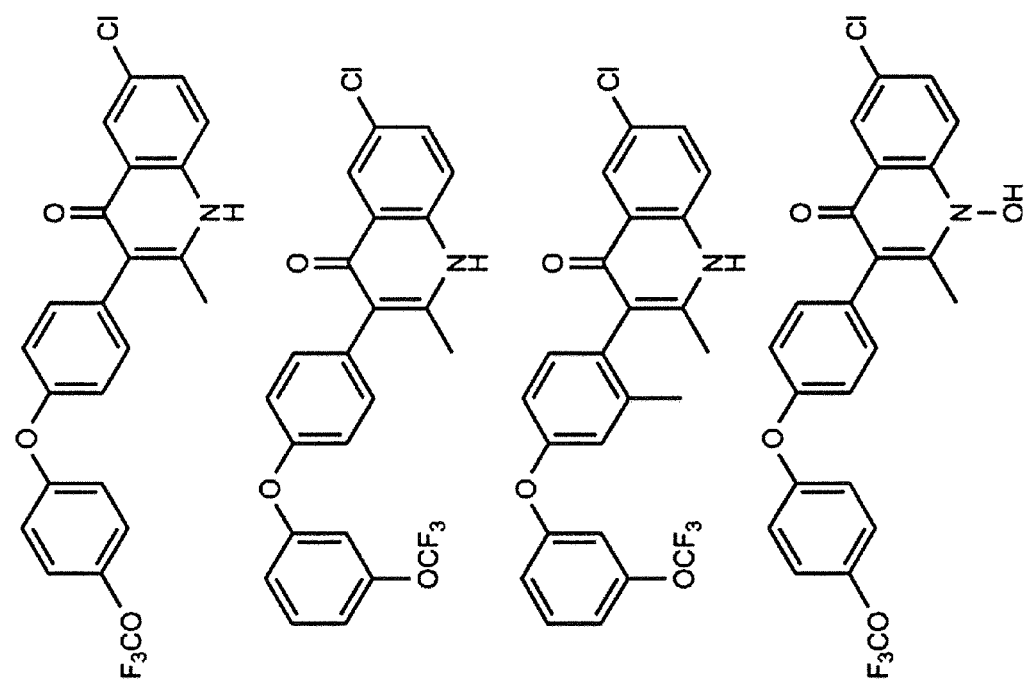
FIG. 12

Examples of 3-position alkyl ELQs with aqueous solubility enhanced by introduction of: 1) polar heteroatoms or ionizable moieties, 2) orthogonal groups/substituents, or 3) prodrug formulation.

Examples of 3-position aryl/phenyl ELQs with aqueous solubility enhanced by introduction of: 1) polar heteroatoms or ionizable moieties, 2) orthogonal groups/substituents, or 3) prodrug formulation.

Examples of aryl-acetylene ELQ derivatives with aqueous solubility enhanced by introduction of 1) polar heteroatoms or ionizable moieties, 2) orthogonal groups/substituents, or 3) prodrug formulation.

Examples of 3-position diarylether ELQs and biphenyl derivatives with aqueous solubility enhanced by introduction of: 1) polar heteroatoms or ionizable moieties, 2) orthogonal groups/substituents, or 3) prodrug formulation.

COMPOUNDS HAVING ANTIPARASITIC OR ANTI-INFECTIOUS ACTIVITY

This is a divisional application of U.S. patent application Ser. No. 13/153,350, which was filed on Jun. 3, 2011, and is a continuation-in-part of International Application No. PCT/US2009/066841, filed Dec. 4, 2009, which was published in English under PCT Article 21(2), which in turn claims the benefit of U.S. Provisional Application No. 61/201,082, filed on Dec. 5, 2008. Each of these is incorporated herein by reference in its entirety.

ACKNOWLEDGMENT OF GOVERNMENT SUPPORT

The United States Government may have certain rights to invention(s) disclosed herein as research that may be relevant to the development of the invention was funded by United States governmental grant funds from the United States Department of Veteran Affairs Medical Research Program.

FIELD

The compounds and composition disclosed herein relate to inhibiting infectious and parasitic diseases, particularly malaria and toxoplasmosis.

BACKGROUND

Diseases caused by organisms of the phylum Apicomplexa include malaria, toxoplasmosis and coccidiosis.

Malaria is a tropical disease, spread by mosquitoes from person to person, that exacts a devastating toll in endemic regions, especially Africa, where it claims 1 to 2 million lives each year. The deaths occur primarily among young children and pregnant women—vulnerable populations for whom therapeutic options are limited. These options are even more restricted in the current landscape of widespread drug resistance in the *Plasmodium* parasites that cause malaria. Together with an increasing incidence of malaria worldwide, there is an urgent and unmet need for new drugs to prevent and treat malaria, an infection that causes clinical disease manifestations in 300 to 500 million people each year.

Malaria is a worsening global health problem. The incidence of malaria continues to increase worldwide, due in part to the emergence of drug resistance but also due to global warming. Initially observed in the late 1950's and early 1960's in South America and Southeast Asia, chloroquine-resistant *Plasmodium* parasites that are associated with the most virulent form of malaria, cerebral malaria, have now spread to all malarious regions of the world. Varney et al. (1994) (1997) and others report a strong correlation between cerebral malaria and neuropsychiatric symptoms, such as poor dichotic listening, 'personality change', depression, and, in some cases, partial seizure-like symptoms. The tropical neuralnesia resulting from the legendary malarial fevers is well known in the endemic areas and has been documented throughout history.

Chloroquine replacement drugs are urgently needed to treat and prevent malaria. The endoperoxides, like artemisinin (derived from a Chinese herbal remedy extracted from the wormwood plant) are being used in other parts of the world for malaria therapy. However, the use of this remedy is limited by reports of ototoxicity and neurotoxic effects of the endoperoxides. More recently, severe reproductive toxicity in female rats has been reported in animals treated with artesunate and its active metabolite, dihydroartemisinin. These findings are mirrored in reports by others in several different animal models.

While the great panacea for malaria therapy would be the development of a long-lasting vaccine, the failure of the SPf66 vaccine and unrealized potential of newer multi-component DNA vaccines, combine to indicate that a vaccine is a long way from reality. As a result, the need continues to exist in the medical field for the development of safe, inexpensive anti-parasitic agents, especially agents that are useful against multi-drug-resistant organisms such as *P. falciparum* and *P. vivax*.

Toxoplasmosis, caused by *Toxoplasma gondii*, is a leading cause of birth defects and it is estimated that the health care costs due to toxoplasmosis are roughly 5 billion dollars each year in the United States. In addition, there are researchers who believe that latent toxoplasmosis infections may underlie certain mental illness conditions including schizophrenia.

Hans Andersag is well known for the discovery of chloroquine (resochin) in the 1930's. He was also connected with the discovery of "endochin", a compound that elicited great interest among Bayer scientists because of its efficacy in treatment and prevention of malaria in a bird model (P. cathemerium/canary) of the disease. In subsequent work summarized by Kikuth and Mudrow-Reichenow, Steck, and Wiselogle, endochin also demonstrated efficacy in treatment and prophylaxis against P. gallinaceum in the chick and P. lophurae in the turkey. Kikuth further reported that endochin exerted gametocidal action against male gametocytes undergoing exflagellation in finches infected with Haemoproteus, a closely related member of the Apicomplexa. Despite these unique and desirable qualities, endochin's antimalarial potential was never realized because it failed to cure malaria infections in subsequent experiments in mammalian species ranging from mice to non-human primates (Rhesus monkeys).

SUMMARY

Disclosed herein are compounds of formula I:

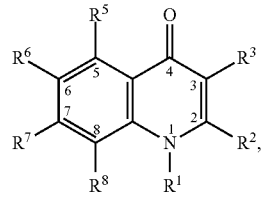

or formula II:

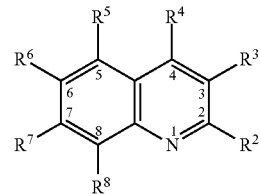

or a pharmaceutically acceptable salt of formula I or formula II, wherein:

$R^1$ is H, hydroxyl, alkoxy, acyl, alkyl, cycloalkyl, aryl, or heteroaryl;

$R^2$ is methyl, haloalkyl, or heteroaryl;

$R^4$ is hydroxyl, carbonyloxy, or carbonyldioxy;

$R^3$ is aliphatic, aryl, aralkyl, or alkylaryl; and $R^5$, $R^6$, $R^7$ and $R^8$ are each individually H, halogen, alkoxy, alkyl, haloalkyl, aryl, nitro, cyano, amino, amido, acyl, carboxyl, substituted carboxyl, or —SO$_2$R$^{10}$, wherein $R^{10}$ is H, alkyl, amino or haloalkyl;

provided that in formula I, $R^5$ and $R^7$ are not H or $R^6$ is not H or methoxy; and in formula II that if $R^4$ is carbonyldioxy then $R^7$ is not methoxy.

Also disclosed herein are compositions comprising a pharmacologically active amount of at least one compound of formula I or II, or a pharmaceutically acceptable salt thereof, and at least one pharmaceutically acceptable carrier.

Further disclosed herein are methods for inhibiting a parasitic or infectious disease in a subject comprising administering to the subject a therapeutically effective amount of a compound of formula I or II, or a pharmaceutically acceptable salt thereof.

The foregoing will become more apparent from the following detailed description, which proceeds with reference to the accompanying figures.

BRIEF DESCRIPTION OF THE DRAWINGS

FIG. 4 is a table listing compounds and their activity against *Plasmodium falciparum* strains in vitro.

FIG. 9 shows illustrative compounds.

FIG. 11 shows illustrative compounds.

FIG. 12 shows illustrative compounds.

DETAILED DESCRIPTION

Figure 1:
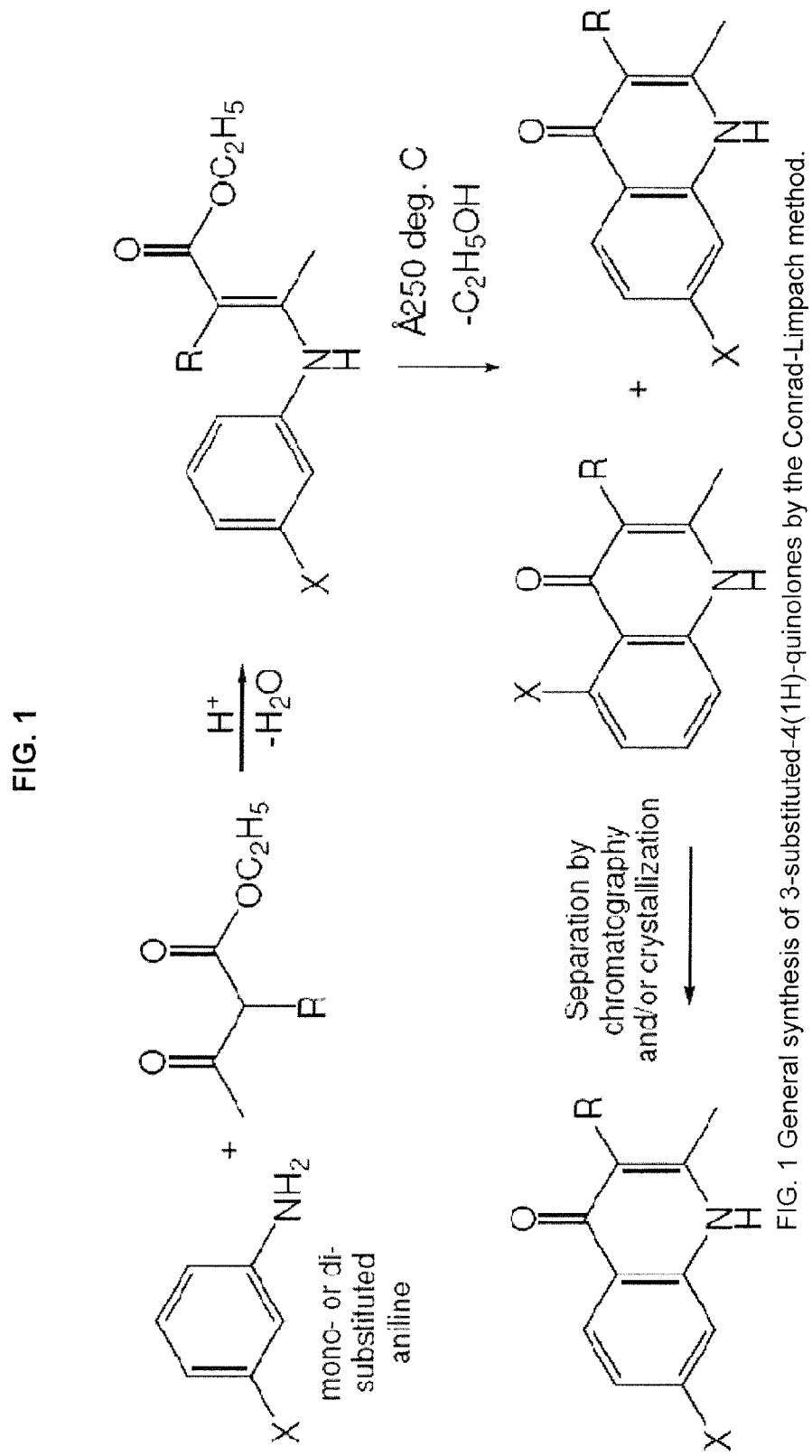
FIG. 1 is a general reaction scheme for synthesizing compounds disclosed herein.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular terms "a," "an," and "the" include plural referents unless context clearly indicates otherwise. Also, as used herein, the term "comprises" means "includes." Hence "comprising A or B" means including A, B, or A and B.

Variables such as $R^1$, $R^2$, $R^3$, $R^4$, $R^5$, $R^6$, $R^7$, $R^8$, $R^9$, n, X and Y, used throughout the disclosure are the same variables as previously defined unless stated to the contrary.

The term "acyl" refers group of the formula RC(O)— wherein R is an organic group.

"Administration of" and "administering a" compound should be understood to mean providing a compound, a prodrug of a compound, or a pharmaceutical composition as described herein. The compound or composition can be administered by another person to the subject (e.g., intravenously) or it can be self-administered by the subject (e.g., tablets).

The term "aliphatic" is defined as including alkyl, alkenyl, alkynyl, halogenated alkyl and cycloalkyl groups as described above. A "lower aliphatic" group is a branched or unbranched aliphatic group having from 1 to 10 carbon atoms.

"Alkanediyl" or "cycloalkanediyl" refers to a divalent radical of the general formula —$C_nH_{2n}$-derived from aliphatic or cycloaliphatic hydrocarbons.

The term "alkenyl" refers to a hydrocarbon group of 2 to 24 carbon atoms and structural formula containing at least one carbon-carbon double bond. A "lower alkenyl" group has 1 to 10 carbon atoms.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, or carboxyl.

The term "alkyl amino" refers to alkyl groups as defined above where at least one hydrogen atom is replaced with an amino group.

The term "alkynyl" refers to a hydrocarbon group of 2 to 24 carbon atoms and a structural formula containing at least one carbon-carbon triple bond.

The term "alkoxy" refers to a straight, branched or cyclic hydrocarbon configuration and combinations thereof, including from 1 to 20 carbon atoms, preferably from 1 to 8 carbon atoms, more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, or heterocycloalkyl group as described above. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

"Alkoxycarbonyl" refers to an alkoxy substituted carbonyl radical, —C(O)OR, wherein R represents an optionally substituted alkyl, aryl, aralkyl, cycloalkyl, cycloalkylalkyl or similar moiety.

The term "amine" or "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group described above.

"Aminocarbonyl" alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —N(R)—C(O)—R (wherein R is a substituted group or H) or —C(O)—N(R). An "aminocarbonyl" is inclusive of an amido group. A suitable aminocarbonyl group is acetamido.

The term "amide" or "amido" is represented by the formula —C(O)NRR', where R and R' independently can be a hydrogen, alkyl, alkenyl, alkynyl, aryl, aralkyl, cycloalkyl, halogenated alkyl, or heterocycloalkyl group described above. A suitable amido group is acetamido.

The term "aralkyl" refers to an aryl group having an alkyl group, as defined above, attached to the aryl group, as defined above. An example of an aralkyl group is a benzyl group.

The term "aryl" refers to any carbon-based aromatic group including, but not limited to, benzene, naphthalene, etc. The term "aryl" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

"Carbonyl" refers to a radical of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine.

"Carboxyl" refers to a —COOH radical. Substituted carboxyl refers to —COOR where R is aliphatic, heteroaliphatic, alkyl, heteroalkyl, or a carboxylic acid or ester.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

"Derivative" refers to a compound or portion of a compound that is derived from or is theoretically derivable from a parent compound.

"Equipotency" refers to the capacity of the inventive compounds disclosed herein to inhibit the growth of parasites, especially drug-resistant *Plasmodium* parasites, with roughly the same power or capacity (e.g., with a range of 2 to 3-fold), regardless of the level of intrinsic resistance to chloroquine, quinine, or other antimalarial agents.

The terms "halogenated alkyl" or "haloalkyl group" refer to an alkyl group as defined above with one or more hydrogen atoms present on these groups substituted with a halogen (F, Cl, Br, I).

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

"Inhibiting" (which is inclusive of "treating") refers to inhibiting the full development of a disease or condition, for example, in a subject who is at risk for a disease such as malaria. "Treatment" refers to a therapeutic intervention that ameliorates a sign or symptom of a disease or pathological condition after it has begun to develop. As used herein, the term "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. "Inhibiting" also refers to any quantitative or qualitative reduction including prevention of infection or complete killing of an invading organism, relative to a control. A "prophylactic" treatment is a treatment administered to a subject who does not exhibit signs of a disease or exhibits only early signs for the purpose of decreasing the risk of developing pathology. By the term "coadminister" is meant that each of at least two compounds be administered during a time frame wherein the respective periods of biological activity overlap. Thus, the term includes sequential as well as coextensive administration of two or more drug compounds.

"Invading" relates to a pathological activity of an organism against a healthy cell, a population of healthy cells, or whole organism.

"Multidrug-resistant" or "drug-resistant" refers to malaria, or the parasites causing malaria, that have developed resistance to treatment by at least one therapeutic agent historically administered to treat malaria. For example, there are multidrug-resistant strains of *Plasmodium falciparum* that harbor high-level resistance to chloroquine, quinine, mefloquine, pyrimethamine, sulfadoxine and atovaquone.

Optionally substituted groups, such as "optionally substituted alkyl," refers to groups, such as an alkyl group, that when substituted, have from 1-5 substituents, typically 1, 2 or 3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, halogen, optionally substituted heteroaryl, optionally substituted heterocyclyl, hydroxy, sulfonyl, thiol and thioalkoxy. In particular, optionally substituted alkyl groups include, by way of example, haloalkyl groups, such as fluoroalkyl groups, including, without limitation, trifluoromethyl groups.

"Optional" or "optionally" means that the subsequently described event or circumstance can but need not occur, and that the description includes instances where said event or circumstance occurs and instances where it does not.

The terms "pharmaceutically acceptable salt" or "pharmacologically acceptable salt" refers to salts prepared by conventional means that include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methylglutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

The term "pharmacologically active amount" relates to an amount of a compound that provides a detectable reduction in parasitic activity in vitro or in vivo, or diminishes the likelihood of emergence of drug resistance.

"Saturated or unsaturated" includes substituents saturated with hydrogens, substituents completely unsaturated with hydrogens and substituents partially saturated with hydrogens.

The term "subject" includes both human and veterinary subjects.

A "therapeutically effective amount" or "diagnostically effective amount" refers to a quantity of a specified agent sufficient to achieve a desired effect in a subject being treated with that agent. For example, this may be the amount of a compound disclosed herein useful in detecting or treating thyroid cancer in a subject. Ideally, a therapeutically effective amount or diagnostically effective amount of an agent is an amount sufficient to inhibit or treat the disease without causing a substantial cytotoxic effect in the subject. The therapeutically effective amount or diagnostically effective amount of an agent will be dependent on the subject being treated, the severity of the affliction, and the manner of administration of the therapeutic composition.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts Protective Groups in Organic Synthesis; 3rd Ed.; John Wiley & Sons, New York, 1999.

In general, protecting groups are removed under conditions which will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts Protective Groups in Organic Synthesis; 3rd Ed.; John Wiley & Sons, New York, 1999.

When an amine is deprotected, the resulting salt can readily be neutralized to yield the free amine. Similarly, when an acid moiety, such as a phosphonic acid moiety is unveiled, the compound may be isolated as the acid compound or as a salt thereof.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

It is understood that substituents and substitution patterns of the compounds described herein can be selected by one of ordinary skill in the art to provide compounds that are chemically stable and that can be readily synthesized by techniques known in the art and further by the methods set forth in this disclosure. Reference will now be made in detail to the presently preferred compounds.

The following abbreviations are used herein:
$ED_{50}$—effective drug concentration required to decrease parasitemia by 50% relative to control, untreated animals;
FACS—fluorescence activated cells sorting/scanning;
Gavage—oral route of drug administration;
$IC_{50}$—drug concentration required to inhibit parasite growth by 50% relative to control values;
i.p.—intraperitoneal;
i.v.—intravenous;
IVTI—in vitro therapeutic index; calculated from the ratio of $IC_{50}$ value based on the cytotoxicity observed in the blastogenesis assay and the anti-malarial potency against the D6 strain (non-drug resistant, drug sensitive) of *P. falciparum*.
MSF—malaria specific fluorescence assay;
PRBC—parasitized red blood cell(s);
RFU—relative fluorescence units Compounds Examples of the compounds disclosed herein exhibit equipotent activity against multidrug-resistant strains of *Plasmodium* parasites and may be of use in treating both the liver and blood stages of malaria as well as other infectious and/or parasitic diseases of humans and animals. Antimalarial drugs targeting the liver stage offer many advantages over drugs that merely target the blood stage. First, drugs active against the liver stage represent true causally prophylactic agents that can prevent all disease symptoms, including death, associated with malaria. Secondly, it has been established that while wild-caught mosquitoes may harbor thousands of sporozoites, only ≈10 sporozoites are transferred in a single bite to the human host. Over the next 2-3 weeks the sporozoite reproduces in the liver to produce 10,000-30,000 descendants before the schizont ruptures and parasites flood into the bloodstream where the absolute parasite burden may increase to ten thousand billion ($10^{13}$) circulating plasmodia. Clearly it is advantageous to strike at the liver stage where parasite numbers are low, to diminish the likelihood of selecting for a drug resistant mutant and before the infection has a chance to weaken the defenses of the human host. The compounds described herein may block sporozoite-induced infections in humans, due to their enhanced metabolic stability in the human system, a feature that endochin lacks. As a result, the compounds can be used prophylactically to prevent malaria due to their ability to interfere with parasite development in the liver stage of malaria infection in humans.

In examples of the compounds disclosed herein, the quinolone nucleus has been modified to enhance metabolic stability and incorporate additional structural changes that endow the compounds with potent intrinsic activity against aminoquinoline-, antifol-, and atovaquone-resistant parasites ($IC_{50}$'s in the low to sub-nanomolar range), low cytotoxicity toward mammalian cells ($IC_{50}$'s>50 μM) and with the therapeutic power to clear a robust *P. yoelii* infection in mice by the oral route of administration. The compounds may exhibit many desirable characteristics of therapeutic molecules: $MW_{(parentmolecule)}$<500, log P <5, achiral, tolerance to extremes of temperature, ease of synthesis, low cost of materials, scaleable chemical procedures, high level of potency, oral bioavailability, parenteral option for drug delivery, once-daily dosing 3-day curative regimen, lack of cytotoxicity, lack of observable whole animal toxicity, and the potential for targeting multiple developmental stages of the parasite life cycle in humans.

In the compounds of formula I, $R^1$ may be H, hydroxyl, alkoxy, acyl, alkyl, cycloalkyl, aryl, or heteroaryl. In certain embodiments, $R^1$ may be H or alkyl (e.g., a branched, linear or cyclic alkyl having 1 to 10 carbon atoms). In some examples, compounds wherein $R^1$ is an alkyl are particularly useful for treating toxoplasmosis.

In the compounds of formula I or II, $R^2$ may be methyl or haloalkyl (e.g., —$CF_3$), particularly methyl.

In the compounds of formula I or II, $R^3$ may be aliphatic, aryl, aralkyl, or alkylaryl. For example, $R^3$ may be cycloalkyl, hetero-cycloalkyl, aliphatic ether, trifluoromethoxy-aliphatic ether, arahaloalkyl, trifluoromethoxy-diarylether, alkyl-heteroaryl, or alkyl-halogenated heteroaryl. Illustrative aliphatic groups include branched, linear or cyclic alkyl or heteroalkyl, or branched or linear alkenyl, particularly alkyl or alkenyl groups having 3 to 12 carbon atoms. In one embodiment, the alkyl or alkenyl is substituted at its terminal end with one or more fluorine atoms. Illustrative terminal moieties include —$CH_2F$, —$CHF_2$, —$CF_3$, —$C_2F_5$, -n-$C_3F_7$, -i-$C_3F_7$, -n-$C_4F_9$, -i-$C_4F_9$, or —$SF_5$. $R^3$ also may be terminated in trifluoromethoxy. In an additional embodiment, $R^3$ is 3-methyl-butyl or 3-methyl-but-2-enyl. In another embodiment, $R^3$ is a heterocycloalkyl or a heteroaryl. In a further embodiment, $R^3$ is heptyl or fluorine-terminated heptyl.

In certain embodiments that may provide enhanced bioavailability, metabolic stability and/or aqueous solubility, $R^3$ of formula I or II may be an optionally substituted cycloalkyl, optionally substituted heterocycloalkyl or an optionally substituted heteroaryl. The cycloalkyl may be cyclohexyl. In certain embodiments, the heterocycloalkyl or heteroaryl are 5- or 6-membered rings that include at least one N and/or O heteroatom. Illustrative heterocycloalkyls include pyrrolidinyl and piperidinyl. Illustrative heteroaryls include pyrrolyl, furanyl, pyranyl, imidazolyl, pyrazolyl, pyridinyl, pyrazinyl, pyrimidinyl, pyridazinyl and isoxazolyl. In certain embodiments, the heterocycloalkyl or heteroaryl includes a single heteroatom (e.g., N or O) that is in the 4' position relative to the attachment point of the heterocycloalkyl to the quinolone. The cycloalkyl, heterocycloalkyl or heteroaryl may be substituted with alkoxy (e.g. lower alkoxy), halogen-substituted alkoxy (e.g. lower alkoxy), halogenated lower alkyl, alkyl and/or halogen.

Formulae V-VII below are examples of structures wherein $R^3$ is an optionally substituted cycloalkyl, optionally substituted heterocycloalkyl or an optionally substituted heteroaryl:

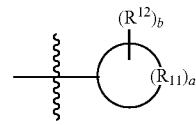

Formula V wherein $R^{11}$ is C or a heteroatom that may be at any position on the ring; a is 3 to 6 (e.g., the ring may contain 0 to 4 heteroatoms); $R^{12}$ is selected from at least one of alkoxy (e.g. lower alkoxy), halogen-substituted alkoxy (e.g. lower alkoxy such as trifluoromethoxy), halogenated lower alkyl, alkyl or halogen; and b is 0 to 5;

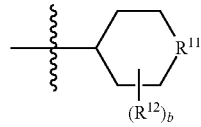

Formula VI wherein $R^{11}$ is a heteroatom and $R^{12}$ is the same as in formula V; or

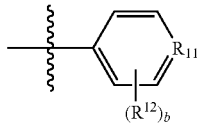

Formula VII wherein $R^{11}$ is a heteroatom and $R^{12}$ is the same as in formula V.

In other embodiments that may provide enhanced bioavailability, metabolic stability and/or aqueous solubility, $R^3$ of formula I or II may be an optionally substituted alkynyl (e.g., an aryl-substituted alkynyl). In certain instances, the alkynyl is ethynyl or a substituted ethynyl. Illustrative substituted ethynyls include an aryl-substituted alkynyl such as phenylethynyl, ethynylpyridine, or ethynylpyrimidine. The aryl ring of the aryl-substituted alkynyl may itself be substituted. Illustrative substituents include alkoxy (e.g. lower alkoxy), halogen-substituted alkoxy (e.g. lower alkoxy), halogenated lower alkyl, alkyl and halogen. The aryl group of the aryl-substituted alkynyl may also be a heterocycloalkyl or heteroaryl as described above.

Formulae VIII-IX below are examples of compounds wherein $R^3$ is an aryl-substituted alkynyl:

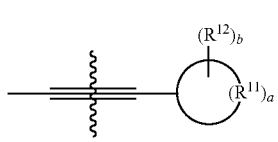

Formula VIII wherein $R^{11}$ is C or a heteroatom that may be at any position on the ring; a is 3 to 6 (e.g., the ring may contain 0 to 4 heteroatoms); $R^{12}$ is selected from at least one of alkoxy (e.g. lower alkoxy), halogen-substituted alkoxy (e.g. lower alkoxy such as trifluoromethoxy), halogenated lower alkyl, alkyl or halogen; and b is 0 to 5; or

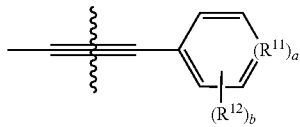

Formula IX wherein $R^{11}$ is a heteroatom, a is 1; and $R^{12}$ is the same as in formula VIII.

In a further embodiment that may provide enhanced bioavailability, metabolic stability and/or aqueous solubility, $R^3$ of formula I or II may be an optionally substituted diarylether. Either one or both of the aryl rings may be substituted phenyl or heteroaryl such as pyridyl or pyrimidyl. Illustrative substituents include alkoxy (e.g. lower alkoxy), halogen-substituted alkoxy (e.g. lower alkoxy such as trifluoromethoxy), halogenated lower alkyl, alkyl, methylsulfonyl and halogen.

Formula X below is an example of wherein $R^3$ is an optionally substituted diphenylether:

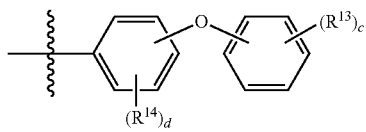

Formula X wherein $R^{13}$ and $R^{14}$ are each individually selected from at least one of alkoxy (e.g. lower alkoxy), halogen-substituted alkoxy (e.g. lower alkoxy such as trifluoromethoxy), halogenated lower alkyl, alkyl and halogen; c is 0 to 5; and d is 0 to 5. In certain embodiments, d is 1 to 4 (preferably d is 1) and $R^{14}$ is a halogen (particularly F). In certain embodiments, c is 1 to 5 (preferably c is 1) and $R^{13}$ is a halogen-substituted alkoxy (e.g. lower alkoxy such as trifluoromethoxy).

In the compounds of formula II, $R^4$ may be hydroxyl, carbonyloxy, or carbonyldioxy. "Carbonyloxy" refers to a divalent structure of the formula —O—C(O)—$R^9$, and "carbonyldioxy" refers to a divalent structure of the formula —O—C(O)—O—$R^9$, wherein $R^9$ is alkyl, alkenyl, alkyl amino, amido, aminocarbonyl, hydroxyalkyl, alkoxyalkyl or alkyl ether. For example, $R^4$ may be a promoiety obtained via esterification of an oxo or hydroxyl group at the 4-position of a precursor compound. In particular, $R^4$ may be an ester or carbonate ester of an organic acid (e.g., succinate, acetate or fumarate), an amino acid (e.g., glycinate), a polyhydric alcohol (e.g, polyethylene glycol or ethylene glycol) or a polyether. For instance, certain compounds have a structure represented by formula III:

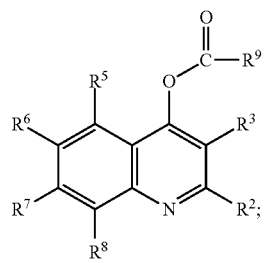

or a structure represented by formula IV:

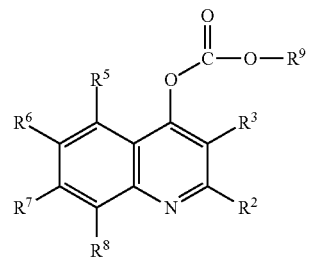

$R^5$, $R^6$, $R^7$ and $R^8$ of formula I or II may be each individually H, halogen, alkoxy, alkyl, haloalkyl, aryl, nitro, cyano, amino, amido, acyl, carboxyl, substituted carboxyl, or —$SO_2R^{10}$, wherein $R^{10}$ is H, alkyl, amino or haloalkyl. In certain embodiments, —$SO_2R^{10}$ is —$SO_2CH_3$, —$SO_2NH_2$, or —$SO_2CF_3$. In other examples, $R^5$ and $R^7$ are not H, and are, in particular, halogen or haloalkyl. In one specific embodiment $R^5$ and $R^7$ are each fluorine and, optionally, $R^6$ and $R^8$ are each H. In another specific embodiment, $R^6$ is not H (e.g., $R^6$ is halogen (particularly chloro or fluoro), haloalkyl, cyano, etc.) and $R^5$, $R^7$ and $R^8$ are each H. In a further specific embodiment, $R^6$ is halogen. In a further specific embodiment, $R^7$ is methoxy. In another specific embodiment, $R^6$ is fluoro and $R^7$ is methoxy.

In particular embodiments of formula I, $R^1$ is H or lower alkyl; $R^2$ is methyl; $R^3$ is branched, linear or cycloalkyl or branched or linear alkenyl; $R^5$ and $R^7$ are each fluorine; and $R^6$ and $R^8$ are each H.

In a further particular embodiment of formula I, $R^1$ is H; $R^2$ is H or methyl (preferably methyl); $R^3$ is cycloalkyl, heterocycloalkyl, heteroaryl, alkynyl or diaryl ether; $R^6$ is halogen; $R^7$ is H or methoxy; and $R^5$ and $R^8$ are each H. More specifically, the $R^3$ group has the structure of any one of formulae V-X above. Even more specifically, $R^3$ is pyrrolidinyl, piperidinyl, pyrrolyl, furanyl, pyranyl, imidazolyl, pyrazolyl, pyridinyl, pyrazinyl, pyrimidinyl, pyridazinyl, isoxazolyl, aryl-substituted ethynyl, or diphenyl ether.

In particular embodiments of formula II, $R^1$ is H or lower alkyl; $R^2$ is methyl; $R^3$ is branched, linear or cycloalkyl or branched or linear alkenyl; $R^4$ is carbonyloxy or carbonyldioxy; and $R^7$ is not methoxy.

Also disclosed herein are compounds of formula XI:

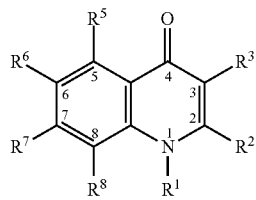

or a pharmaceutically acceptable salt of formula XI, wherein:

$R^1$ is H, hydroxyl, alkoxy, acyl, alkyl, cycloalkyl, aryl, or heteroaryl;

$R^2$ is H, carboxyl, substituted carboxyl, alkyl, haloalkyl, or heteroaryl;

$R^5$, $R^6$, $R^7$ and $R^8$ are each individually H, halogen, alkoxy, alkyl, haloalkyl, aryl, nitro, cyano, amino, amido, acyl, carboxyl, substituted carboxyl, or —$SO_2R^{10}$, wherein $R^{10}$ is H, alkyl, amino or haloalkyl; and $R^3$ is an optionally substituted cycloalkyl, an optionally substituted heterocycloalkyl, an optionally substituted heteroaryl, an optionally substituted alkynyl or an optionally substituted diaryl ether.

In certain embodiments, the $R^3$ group for formula XI has the structure of any one of formulae V-X above.

In a further particular embodiment of formula XI, $R^1$ is H; $R^2$ is H or methyl (preferably methyl); $R^6$ is halogen; $R^7$ is H or methoxy; and $R^5$ and $R^8$ are each H. In specific embodiments, $R^3$ is pyrrolidinyl, piperidinyl, pyrrolyl, furanyl, pyranyl, imidazolyl, pyrazolyl, pyridinyl, pyrazinyl, pyrimidinyl, pyridazinyl, isoxazolyl, aryl-substituted ethynyl, or diphenyl ether.

In certain embodiment, formulae I-XI disclosed above are inclusive of oxo-quinolone-N-oxide analogs thereof.

General Methods Used in Preparation of 4(1H)-Quinolones and Prodrugs of them. The method utilizes the Conrad-Limpach reaction (see FIG. 1), which consists of condensing a substituted (position 2) acetoacetic ester with an aniline, which provides a 2-substituted-3-phenylamino crotonic ester (alternatively formulated as a Schiff base) and is followed by ring-closure in a high-boiling solvent, e.g., Dowtherm A, (atm. p) at ≈250° C., a mixture of 73.5% diphenylether and 26.5% biphenyl, to form the desired quinolone. This method allows for reliable syntheses of quinolones varying in substitution pattern on the benzenoid ring and varying in the length and nature of the substituent group at the 3-position. Once the core 4(1H)-quinolone is synthesized and purified further modifications can be made to enhance activity or physical chemical properties that in turn enhance drug delivery.

More particularly, the Conrad-Limpach synthesis of substituted quinolones (shown in FIG. 1) which requires the condensation of a meso- (=2-) substituted acetoacetic ester with an aniline, followed by condensation of the intermediate 3-anilinocrotonic ester [Walter Salzer, Helmut Timmler, Hans Andersag, Über einen neuen, gegen Vogelmalaria wirksamen Verbindungstypus, Chem. Ber. 81, 12 (1948)] at ≈250° C. This condensation is most conveniently carried out in a stable solvent boiling at that temperature. Useful for this purpose are, e.g. 2-chloro-naphthalene, a mixture of 73.5% diphenyl ether and 26.5% diphenyl (Dowtherm A) or hydrocarbons boiling at that temperature. Dowtherm A was used throughout. An alternative procedure that is useful for heat-sensitive substituents consists of cyclizing the intermediate 3-anilinocrotonic ester by heating with phosphoroxy trichloride to produce a 4-chloroquinoline which may be hydrolyzed to the corresponding 4-quinolone [Gerhard Buchmann, Wolfgang Grimm, J. prakt. Chemie, 17, 135 (1962)].

Figure 6:
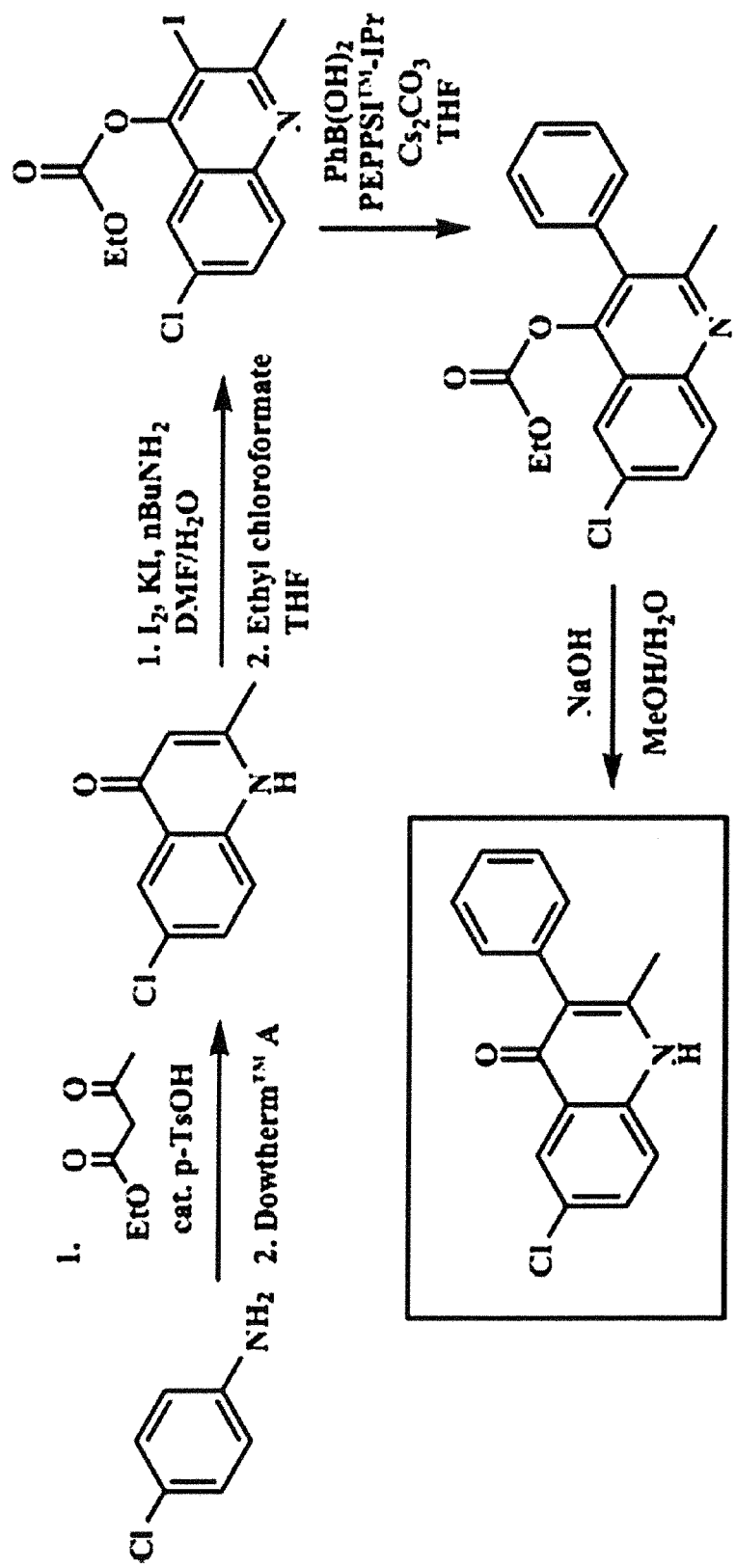
FIG. 6 is an example of an additional reaction scheme for synthesizing compounds disclosed herein.

Certain examples of the compounds may be made by a Suzuki coupling reaction as shown in FIG. 6. Miyaura et al., Tetrahedron letters 1979 Vol. 20 Issue 36, pp 3437-3440. Potential advantages of the Suzuki method are (1) higher yield from more reactive iodide, (2) simplified purification, ethyl acetate/hexane chromatography, (3) quinolone crystallizes out of solution during deprotection reaction.

Figure 7:
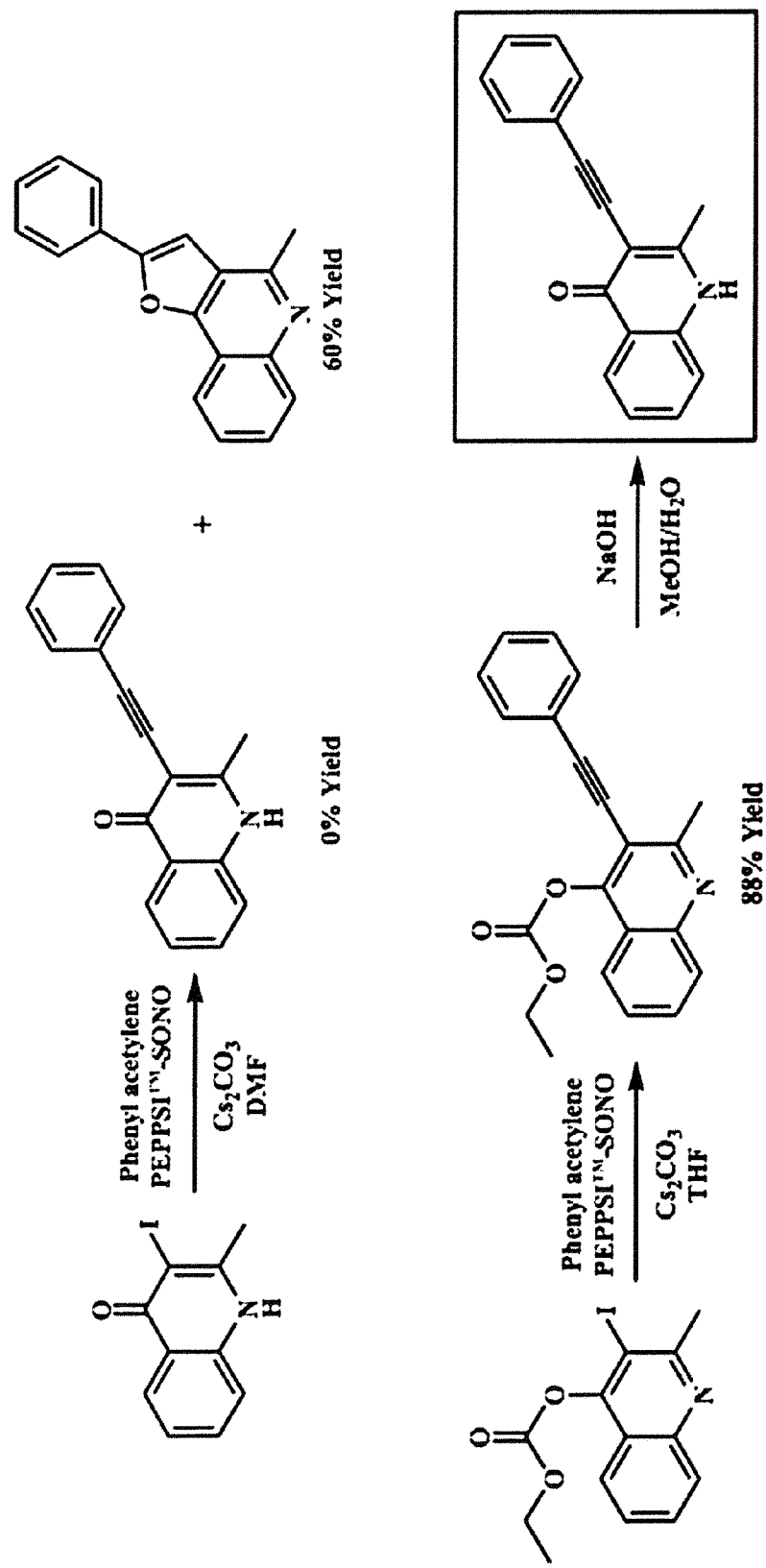
FIG. 7 is an example of an additional reaction scheme for synthesizing compounds disclosed herein.
Figure 8:
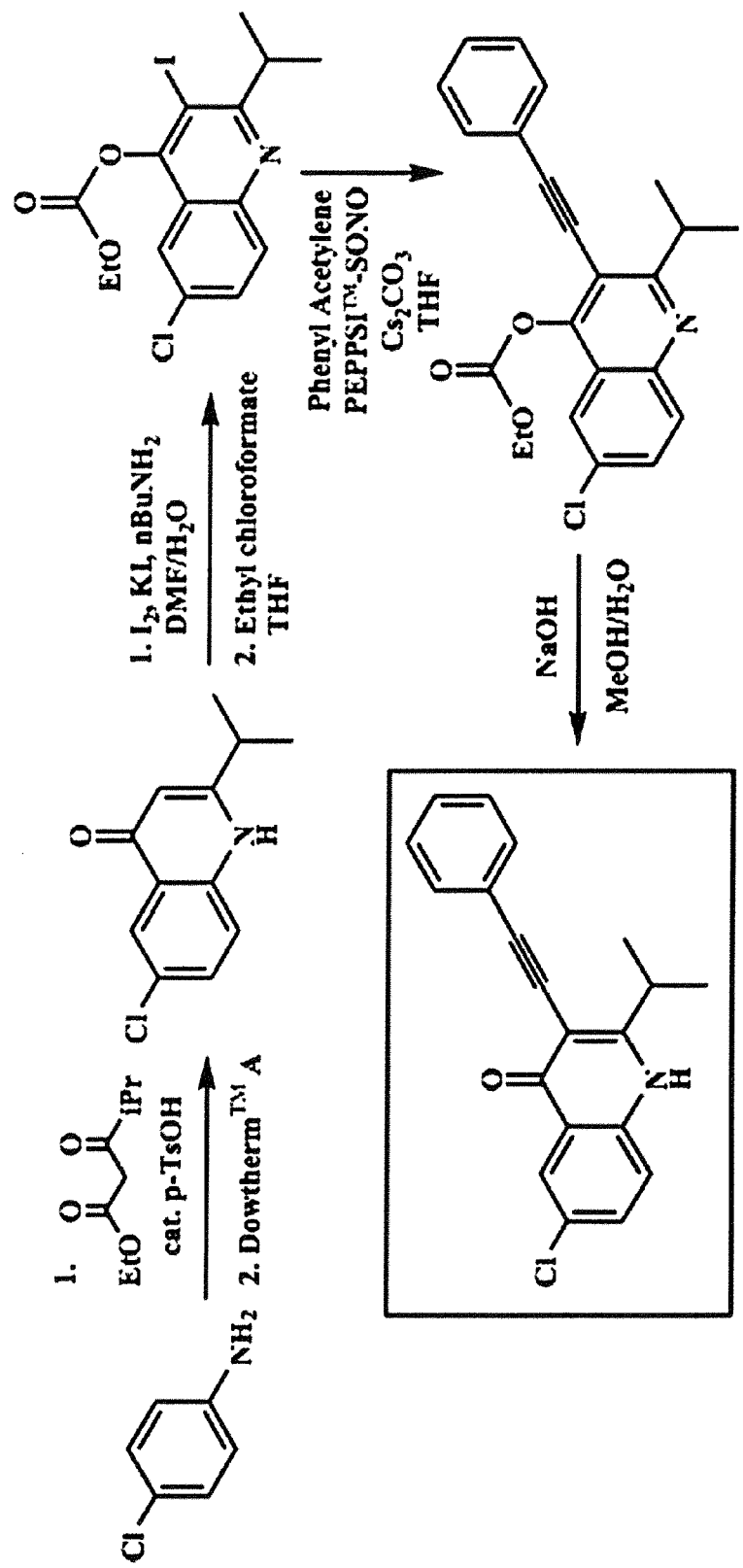
FIG. 8 is an example of an additional reaction scheme for synthesizing compounds disclosed herein.
Figure 10:
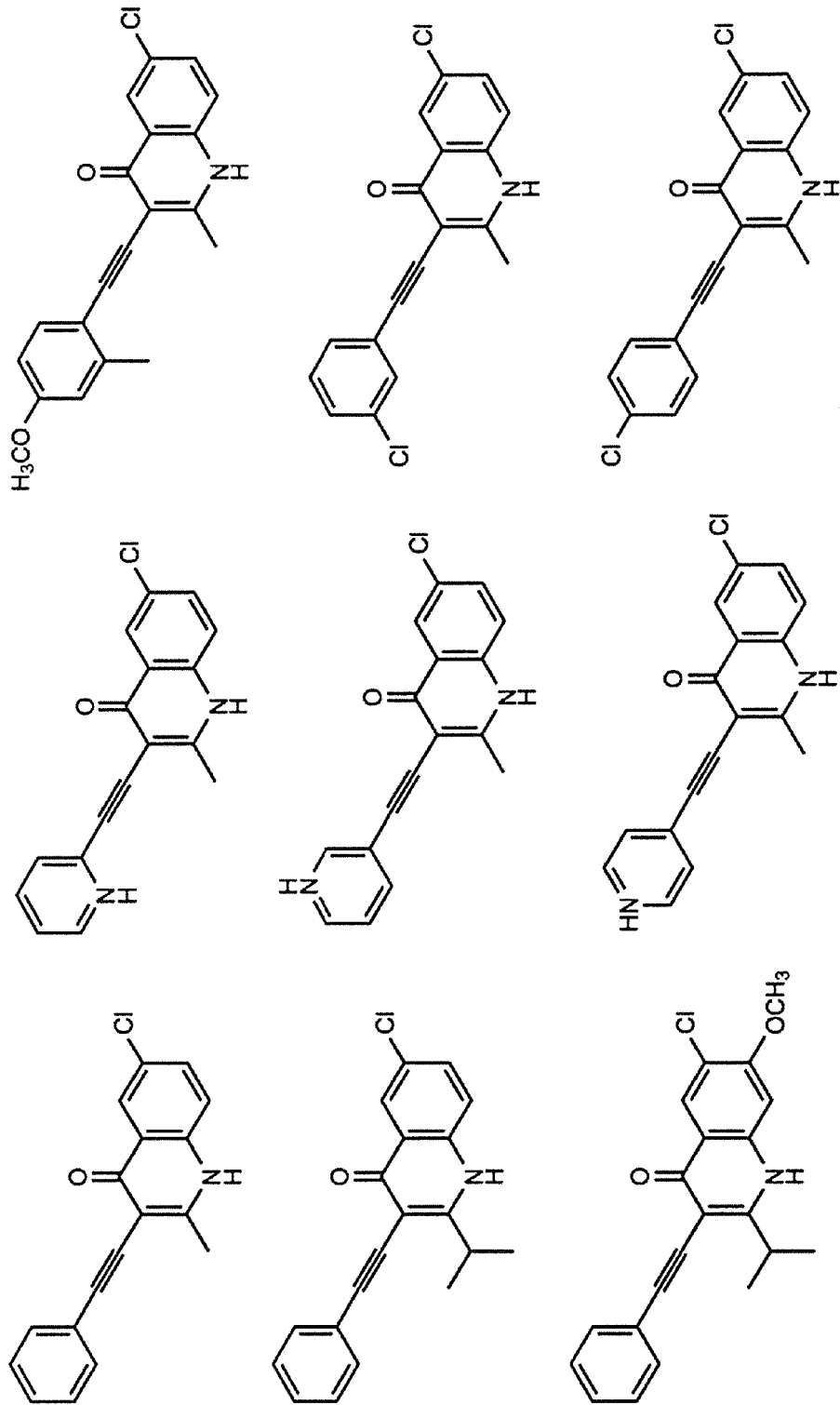
FIG. 10 shows illustrative compounds.
Figure 13:
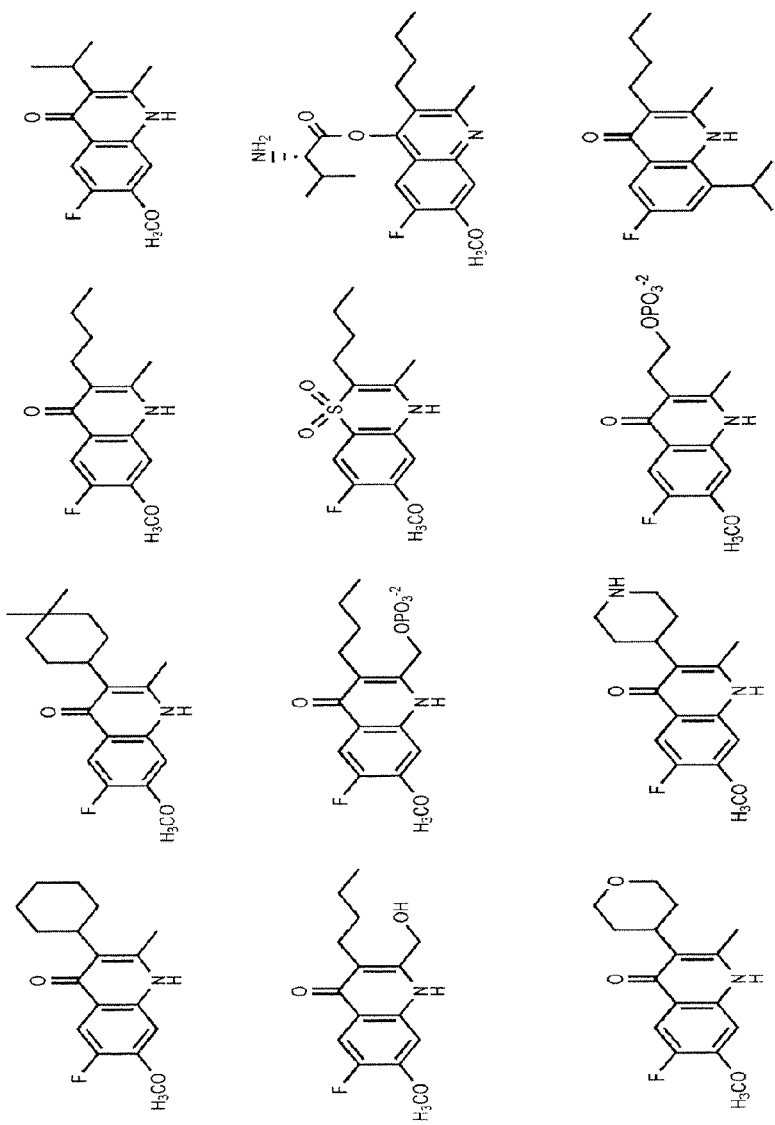
FIG. 13 shows illustrative compounds.
Figure 14:
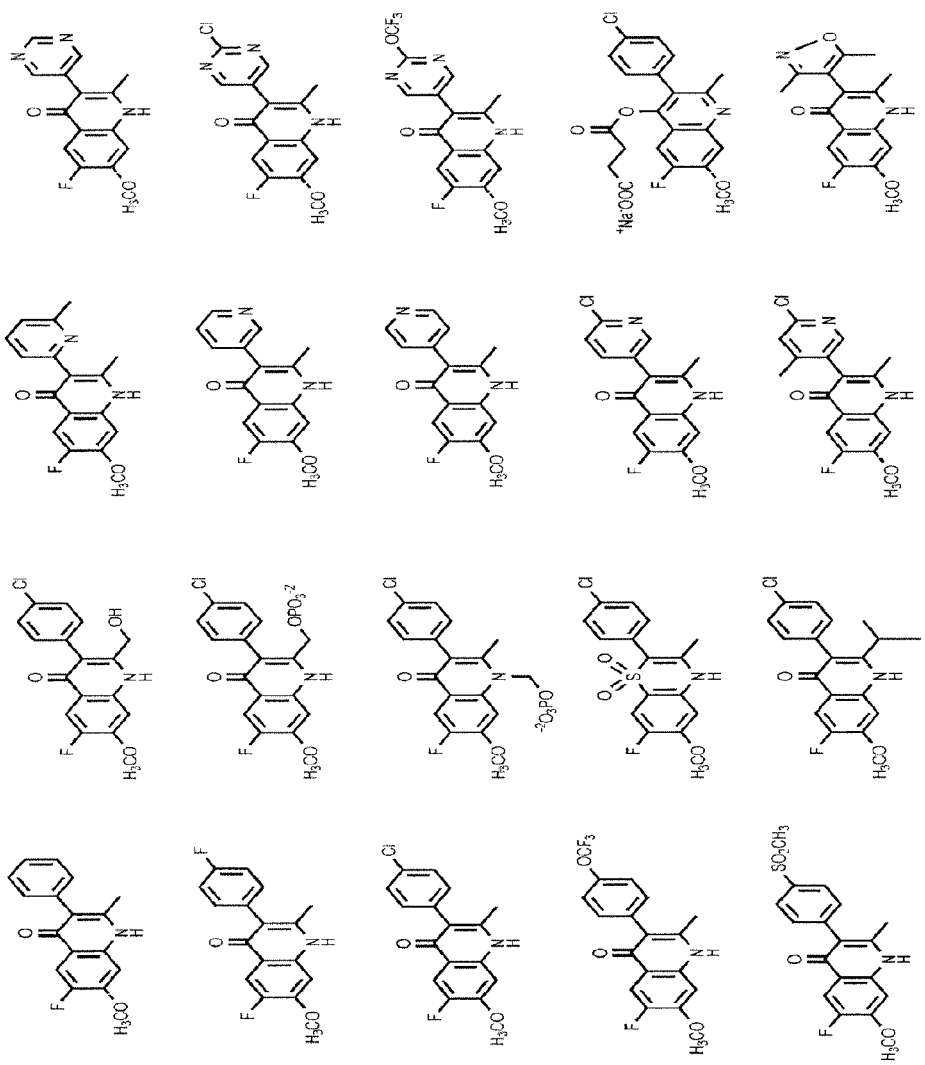
FIG. 14 shows illustrative compounds.
Figure 15:
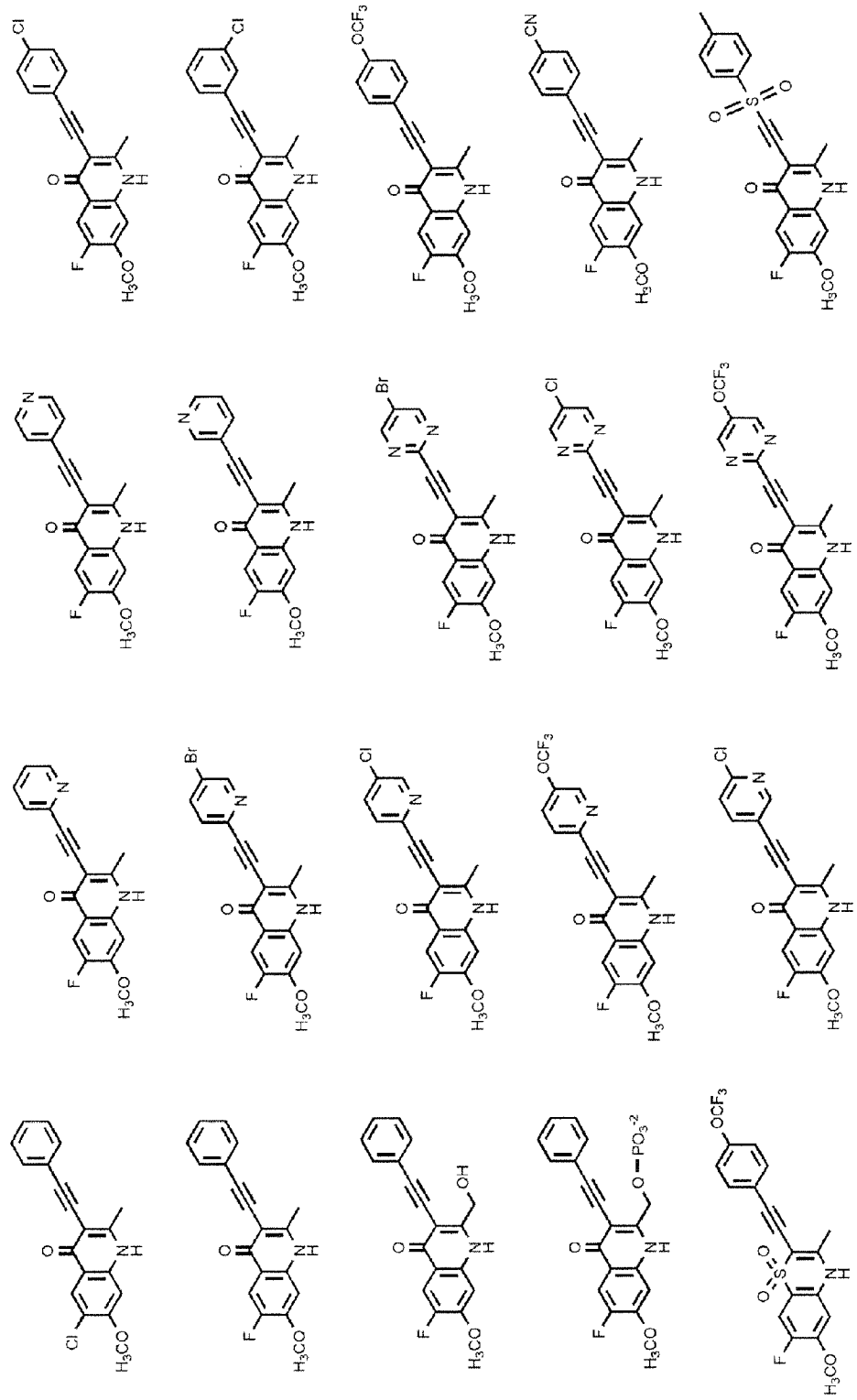
FIG. 15 shows illustrative compounds.
Figure 16:
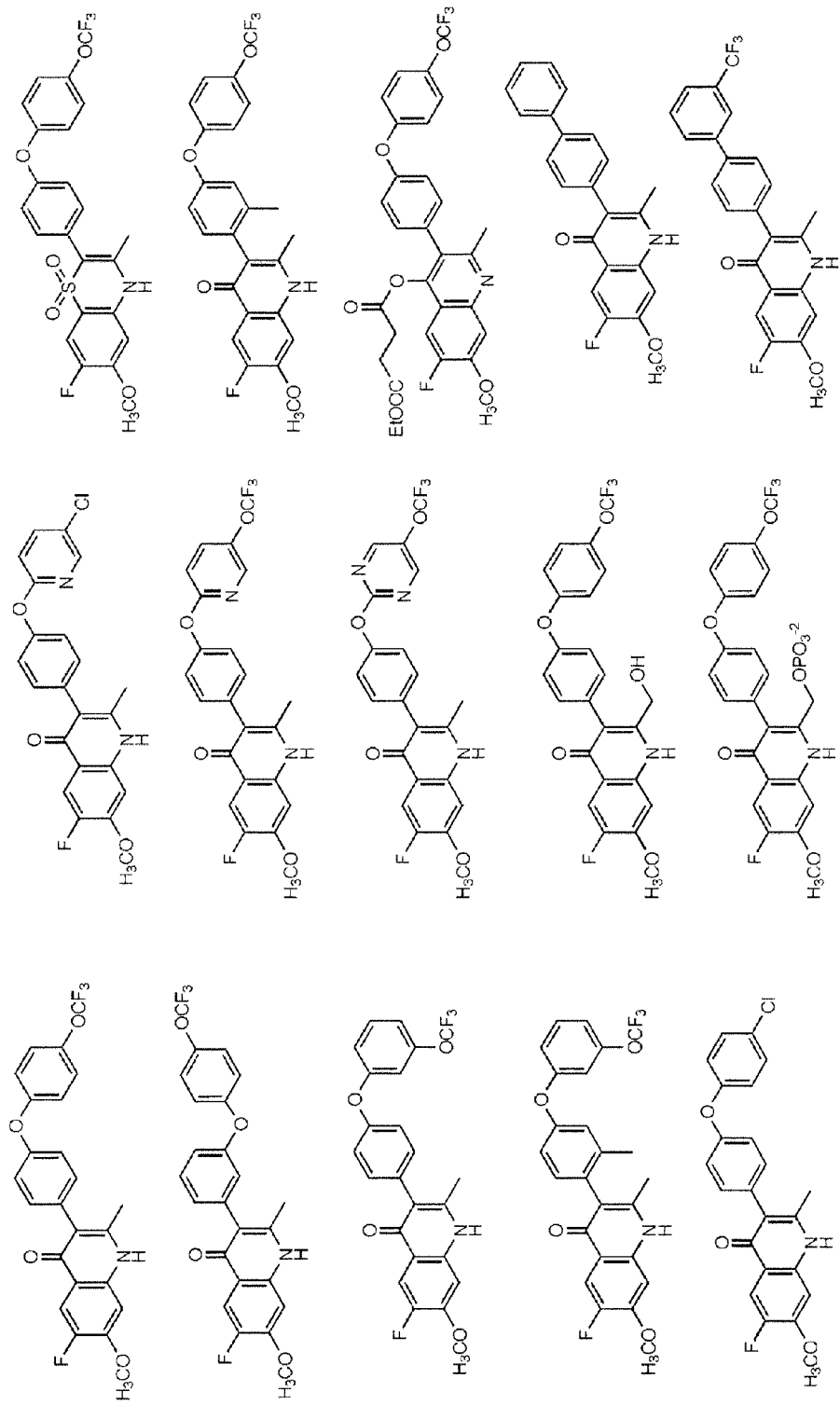
FIG. 16 shows illustrative compounds.

According to another embodiment, certain examples of the compounds may be made by a Sonogashira reaction sequence as shown in FIG. 7. Sonogashira et al., Tetrahedron letters 16 (50): 4467-4470. A further synthesis scheme is shown in FIG. 8 for introducing an isopropyl group at the 2-position.

Composition and Methods

The compounds and pharmaceutical compositions disclosed herein can be used for inhibiting or preventing parasitic diseases. For example, human or animal parasitic diseases include malaria, toxoplasmosis, amebiasis, giardiasis, leishmaniasis, trypanosomiasis, and coccidiosis, caused by organisms such as *Toxoplasma* sp., *Eimeria* sp., *Babesia bovis, Theileria* sp., and also includes infections by helminths, such as ascaris, schistosomes and filarial worms. The compounds and compositions are also effective in the inhibition of fungal pathogens including *Pneumocystis carinii, Aspergillus fumigatus*, and others.

In particular embodiments, the parasitic diseases may be caused by parasites that cause malaria. Particular species of parasites that are included within this group include all species that are capable of causing human or animal infection. Illustrative species include *Plasmodium falciparum, Plasmodium vivax, Plasmodium ovale, Plasmodium knowlesi*, and *Plasmodium malariae*. The compounds and compositions disclosed herein are particularly useful for inhibiting drug-resistant malaria such as chloroquine-resistant malaria or multidrug-resistant malaria that is caused by organisms harboring resistance to chloroquine, quinine, mefloquine, pyrimethamine, dapsone, and/or atovaquone.

Toxoplasmosis is caused by a sporozoan parasite of the Apicomplexa called *Toxoplasma gondii*. It a common tissue parasite of humans and animals. Most of the infections appear to be asymptomatic (90%), however toxoplasmosis poses a serious health risk for immuno-compromised individuals, such as organ transplant recipients, cancer and AIDS patients, and the unborn children of infected mothers. The compounds disclosed herein may be used alone to treat toxoplasmosis or they may be co-administered with "antifolates" such as sulfonamides, pyrimethamine, tirmethoprim, biguanides and/or atovaquone.

In further embodiments, the compounds disclosed herein may be co-administered with another pharmaceutically active compound. For example, the compounds may be co-administered with quinine, chloroquine, atovaquone, proguanil, primaquine, amodiaquine, mefloquine, piperaquine, artemisinin, methylene blue, pyrimethamine, sulfadoxine, artemether-lumefantrine (Coartem®), dapsone-chlorproguanil (LAPDAP®), artesunate, quinidine, clopidol, pyridine/ pyridinol analogs, 4(1H)-quinolone analogs, dihydroartemisinin, a mixture of atovaquone and proguanil, an endoperoxide, an acridone as disclosed in WO 2008/064011 (which is incorporated herein by reference in its entirety), a pharmachin as disclosed in U.S. Provisional Patent Application titled "Compounds for Treating Parasitic Disease" filed Nov. 18, 2008 (which is incorporated herein by reference in its entirety), or any combination of these.

The compounds disclosed herein may be included in pharmaceutical compositions (including therapeutic and prophylactic formulations), typically combined together with one or more phaimaceutically acceptable vehicles or carriers and, optionally, other therapeutic ingredients (for example, antibiotics, anti-inflammatories, or drugs that are used to reduce pruritus such as an antihistamine). The compositions disclosed herein may be advantageously combined and/or used in combination with other antimalarial agents as described above.

Such pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly(epsilon-caprolactone), poly(epsilon-aprolactone-CO-lactic acid), poly(epsilon.-aprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

Typical subjects intended for treatment with the compositions and methods of the present disclosure include humans, as well as non-human primates and other animals. To identify subjects for prophylaxis or treatment according to the methods of the disclosure, accepted screening methods are employed to determine risk factors associated with a parasitic infection to determine the status of an existing disease or condition in a subject. These screening methods include, for example, preparation of a blood smear from an individual suspected of having malaria. The blood smear is then fixed in methanol and stained with Giemsa and examined microscopically for the presence of *Plasmodium* infected red blood cells. These and other routine methods allow the clinician to select patients in need of therapy using the methods and pharmaceutical compositions of the disclosure.

The administration of the compound of the disclosure can be for either prophylactic or therapeutic purpose. When provided prophylactically, the compound is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the compound can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models (for example, whole cell assays that monitor the effect of various drugs on parasite growth rate). Using such models, only ordinary calculations and adjustments are required to determine an appropriate concentration and dose to administer a therapeutically effective amount of the compound (for example, amounts that are effective to elicit a desired immune response or alleviate one or more symptoms of a targeted disease). In alternative embodiments, an effective amount or effective dose of the compound may simply inhibit or enhance one or more selected biological activities correlated with a disease or condition, as set forth herein, for either therapeutic or diagnostic purposes.

The actual dosage of the compound will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.01 mg/kg body weight to about 20 mg/kg body weight, such as about 0.05 mg/kg to about 5 mg/kg body weight, or about 0.2 mg/kg to about 2 mg/kg body weight.

Dosage can be varied by the attending clinician to maintain a desired concentration at a target site (for example, the lungs or systemic circulation). Higher or lower concentrations can be selected based on the mode of delivery, for example, transepidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

The instant disclosure also includes kits, packages and multi-container units containing the herein described pharmaceutical compositions, active ingredients, and/or means for administering the same for use in the prevention and treatment of diseases and other conditions in mammalian subjects. Kits for diagnostic use are also provided. In one embodiment, these kits include a container or formulation that contains one or more of the conjugates described herein. In one example, this component is formulated in a pharmaceutical preparation for delivery to a subject. The conjugate is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

EXAMPLES

Figure 2:
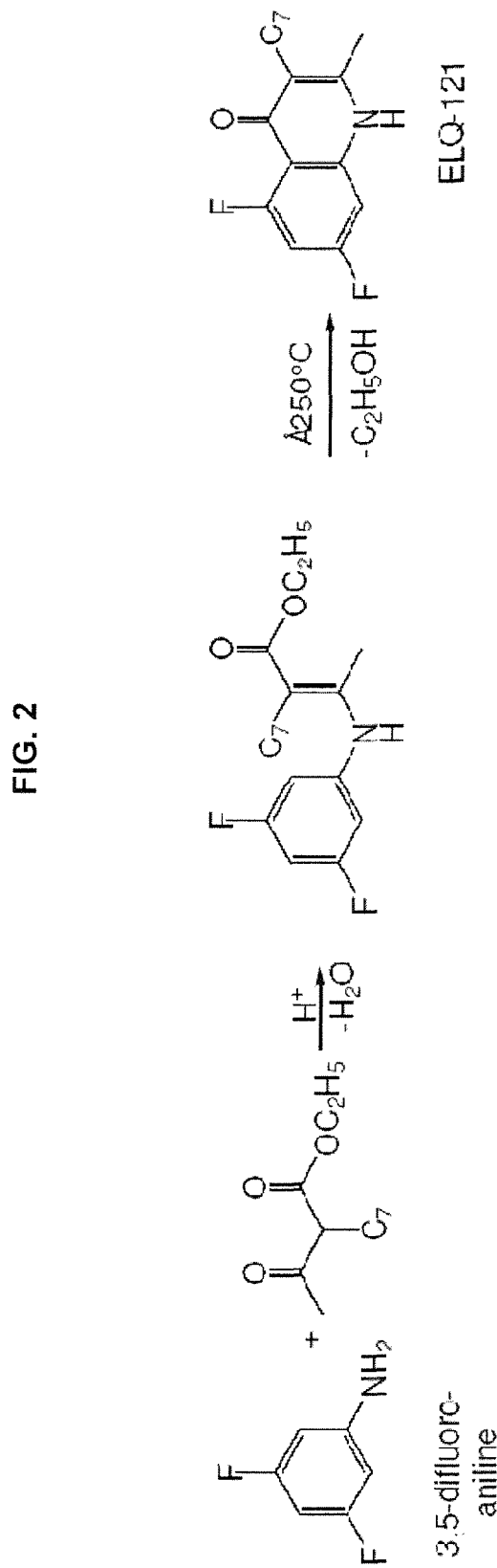
FIG. 2 is a reaction scheme for a specific compound disclosed herein.

FIG. 2 depicts the reaction sequence for preparation of ELQ-121 by the Conrad-Limpach approach.

Synthesis of 2-Methyl-3-(n-heptyl)-5,7-difluorquinolone (ELQ-121)

Ethyl 2-n-heptylacetoacetate (10.0 g, 43.9 mmol), 3,5-difluoroaniline (5.67 g, 43.9 mmol), 200 ml benzene and 0.20 g p-toluenesulfonic acid monohydrate are heated in a flask fitted with a water separator for 20 hours; more acid (0.30 g) is added and water removal continued for 3 more days. Solvent is removed (rotary evaporator) and the residue dropped quickly into 15 ml of boiling Dowtherm A, kept at boiling temperature for 5 minutes and allowed to cool. The product crystallizes out upon cooling. After one and one-half hours the mass is broken up and transferred to a suction funnel; soluble components are washed out with a total of about 50 ml of hexane. Re-crystallization from about 100 ml of dimethylformamide leaves 6.43 g of pure product as shiny flakes (50.0%). M.p. 294-296° C.

$^1$H-n.m.r. spectrum (400 MHz, $(CD_3)_2SO$, $Si(CH_3)_4$=0): $\delta_{CH3(pos.2)}$=2.33 ppm, s, 3H; $C_7$-chain: $\delta_{CH2(pos.3)}$=2.41, dist. t, 2H; $\delta_{(CH2)5(middle)}$=1.2-1.4, indistinct features, 10H; $\delta_{CH3}$=0.87, t, J=6.8 Hz, 3H. $\delta_6$=6.95, d-d-d, $J_{56}$=12, $J_{67}\approx$10, $J_{68}\approx$2.5; $\delta_8\approx$7.0, d-d-d, $J_{58}$=1.35 (not resolved in $^{19}$F-spectrum), $J_{68}$=2.5, $J_{78}$=10.0, H(6)+H(8)=2H; $\delta_{NH}$=11.4, s(br.), 0.85H.

$^{19}$F-n.m.r. spectrum (400 MHz, $(CD_3)_2SO$, $CCl_3F$=0): $\delta_5$=−108.6, t, J=12.7 Hz, 1F; $\delta_7$=−106.3, quartett, J=10.6 Hz, 1F.

Mass spectrum: $M^+$=293, 18%; $(M-C_6H_{13})^+$=208, 100%.

2-Methyl-3-(n-heptyl)-5,7-difluorquinolone (ELQ-121) through hydrolysis of the 4-chloro-2-methyl-3-(n-heptyl)-5,7-difluorquinoline When the anilinocrotonic acid from the above procedure is heated with an excess of $POCl_3$ for about two hours, 4-Chloro-2-methyl-3-(n-heptyl)-5,7-difluorquinoline is obtained. This (2.25 g) heated with 15 ml of conc. HCl and 30 ml of water at reflux temperature for three days, and the product filtered off after cooling and washed with a small amount of ethanol, then ether and ethanol again, 1.45 g (69%) of 2-Methyl-3-(n-heptyl)-5,7-difluorquinolone (Elq-121) is obtained.

It is not necessary to purify the 2-substituted acetoacetates as is illustrated in the following example. Only traces of ethyl acetoacetate may be present, as this will give rise to the formation of a quinolone unsubstituted in position 3:

2-Methyl-3-undecyl-5,7-difluoroquinolone (ELQ-148)

Ethyl 2-(n-undecyl)-acetoacetate was prepared from undecyl iodide (26.6.g) by reaction with an equivalent amount of the sodium derivative of ethyl acetoacetate in ethanol (5 hours, reflux temperature). After cooling the solvent is removed on a rotary evaporator, 300 ml of hexane is added to the residue, and the precipitate of salt is now easily filtered. The product is of sufficient purity (g.c-m.s.) to dispense with further work-up. Reaction of it (6.80 g) with 3,5-difluoroaniline (3.1 g) and 0.30 g of p-toluenesulfonic acid monohydrate in 100 ml of benzene (water separator, 3 days) produced the anilinocrotonic ester with very little of the starting materials left. After removal of the solvent, the crude product was added quickly to 30 ml of boiling Dowtherm A and kept at boiling temperature for about 10 minutes. The product crystallizes out upon cooling and is isolated by filtration and washing with hexane (50 ml).

After re-crystallization from dimethylformaide (150 ml), 4.22 g (50%) of a soft crystal mass is obtained. M.p.=277-278° C.

$^1$H-n.m.r. spectrum (400 MHz, $(CD_3)_2SO$, $Si(CH_3)_4$=0): $\delta_{CH3(pos.2)}$=2.33 ppm, s, 3H; $C_{11}$-chain: $\delta_{CH2(pos.3)}$=2.40, dist. t, 2H; $\delta_{(CH2)9(middle)}$=1.2-1.4, indistinct features, 18H; $\delta_{CH3}$=0.84, t, J=6.8 Hz, 3H. $\delta_6$=6.93, d-d-d, $J_{56}\approx$12, $J_{67}\approx$10, $J_{68}\approx$2.5; $\delta_8\approx$6.98, not resolved H(6)+H(8)=2H; $\delta_{NH}$=11.4, s(br.), 0.9H.

$^{19}$F-n.m.r. spectrum (400 MHz, $(CD_3)_2SO$, $CCl_3F$=0): $\delta_5$=−108.6, t, J=11.65 Hz, 1F; $\delta_7$=−106.3, quartett, J=10.25 Hz, 1F.

Mass spectrum: $M^+$=349, 8%; $(M-C_6H_{13})^+$=208, 100%.

Figure 3:
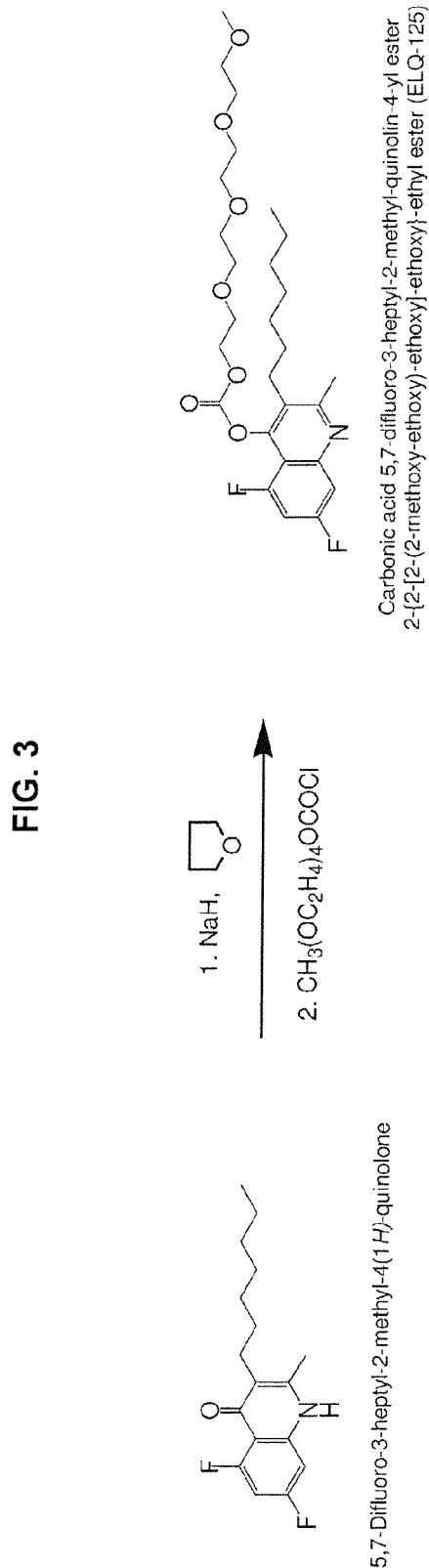
FIG. 3 is a reaction scheme for another specific compound disclosed herein.

Synthesis of the Mixed Carbonate Ester Derivative ELQ-125 of ELQ-121 (See FIG. 3):

0.51 g of 5,7-$F_2$-2-$CH_3$-3-n-$C_7H_{15}$ quinolone (ELQ-121) was stirred in 10 ml of anhydrous tetrahydrofuran with 75 mg of 60% NaH (in paraffin, slight excess) in a lightly capped vial for about one half hour, when a pale yellow almost clear solution resulted. To this solution was added 0.54 g of $CH_3$ (OCH$_2$CH$_2$)$_4$OCOCl (slight excess) with stirring. After 1 day 3 more drops of the acid chloride was added and stirring continued for one more day. The solution was filtered to remove a white precipitate, evaporated and chromatographed on a short column (Kieselgel, 7 cm i.d.×5 cm, CH$_2$Cl$_2$) The sample dissolved in methylene chloride was washed onto the column with 50 ml of CH2Cl2, followed by a 1:1-mixture of ethyl acetate and hexane (isomer mixture). The elution was followed by thin-layer chromatography. Later fractions contained a by-product. The fraction containing our Elq-125 was brought to dryness, leaving 0.46 g of a very pale yellow oil (50% of theory).

$^1$H-n.m.r. spectrum (400 MHz, CDCl$_3$, Si(CH$_3$)$_4$=0): $\delta_{CH3(pos.2)}$=2.74 ppm, s, 3H; C$_7$-chain: $\delta_{CH2(pos.3)}$=2.72, dist. t, overlap with $\delta_{CH3(pos.2)}$, together 5H; $\delta_{CH2(middle)}$=1.2-1.6, indistinct features, 10H; $\delta_{CH3}$=0.88, t, J=6.88 Hz, 3H; polyether chain of carbonate: $\delta$=3.55-3.72, 2 m, 12H; $\delta$=2.82, m, 2H; $\delta$=4.46, m, 2H; $\delta_{CH3}$=3.36, s, 3H. $\delta_6$=6.97, d-d-d; J$_{56}$=8.9, J$_{67}$=9.6, J$_{68}$=2.5, 1H; $\delta_8$=7.48, d-d-d, J$_{58}$=1.3 (not res. in $^{19}$F- spectrum), J$_{68}$=2.5, J$_{78}$=9.6, 1H.

$^{19}$F-n.m.r. spectrum (400 MHz, CDCl$_3$, Si(CH$_3$)$_4$=0): $\delta_5$=−108.6, quartett, J$_{average}$=8.9, 1F; $\delta_7$=−114.2, d-d or t, J≈9.7 Hz, 1F.

Mass spectrum: M$^+$=527, <1%; CH$_3$OCH$_2$CH$_2^+$=59, 100%.

N.2-Dimethyl-3-isopentyl-5,7-difluoroquinoline (ELQ-151)

2-Methyl-3-isopentyl-5,7-difluoroquinolone (ELQ-138), 0.50 g, 5 ml of dry p-dioxane and 150 mg of NaH (60% onin paraffin) were heated in a 25-ml-Carius tube at 120° C. for 5 hours. After cooling the reaction mixture was poured into 100 ml of water and 3 times extracted with 50 ml of ethyl acetate each. The combined extracts were brought to dryness and run through a short column of Kieselgel Merck (5 cm i.d., 4 cm height) with 1:1 ethyl acetate-hexane (isomer mixture), the forerun being discarded. 0.21 g of white crystalline residue remained after evaporation. M.p.=154-155° C.

$^1$H-n.m.r. spectrum (400 MHz, (CD$_3$)$_2$SO, Si(CH$_3$)$_4$=0): $\delta_{CH3(pos.2)}$=2.45 ppm, s, 3H; C$_{i\text{-}Pentyl}$-chain: $\delta_{CH2(pos.3)}$=2.53, dist. t, 2H; $\delta_{CH2(middle)}$=1.21, symm. M., 2H; $\delta_{CH}$=0.1.58, septett, J=6.6 Hz, 1H, $\delta_{CH3}$=0.93, d, J=6.6, 6H. $\delta_6$=7.07, d-d-d, J$_{56}$=12, J$_{67}$=9.6, J$_{68}$≈2.4, 1H; $\delta_8$=7.42, d-d-d, J$_{58}$=1.7 (not resolved in $^{19}$F-spectrum), J$_{68}$=2.4, J$_{78}$=12.1, 1H. $\delta_{NCH3}$=3.68. s, 3H.

$^{19}$F-n.m.r. spectrum (400 MHz, (CD$_3$)$_2$SO, CCl$_3$F=0): $\delta_5$=−107.8, t, J=11.9 Hz; $\delta_7$=−105.7, d-t, J=12.0, J=9.5 Hz.

Mass spectrum: M$^+$=279, 9%, (M-CH$_2$CH(CH$_3$)$_2$+H)$^+$=223, 100%.

Synthesis Scheme for ELQ-300

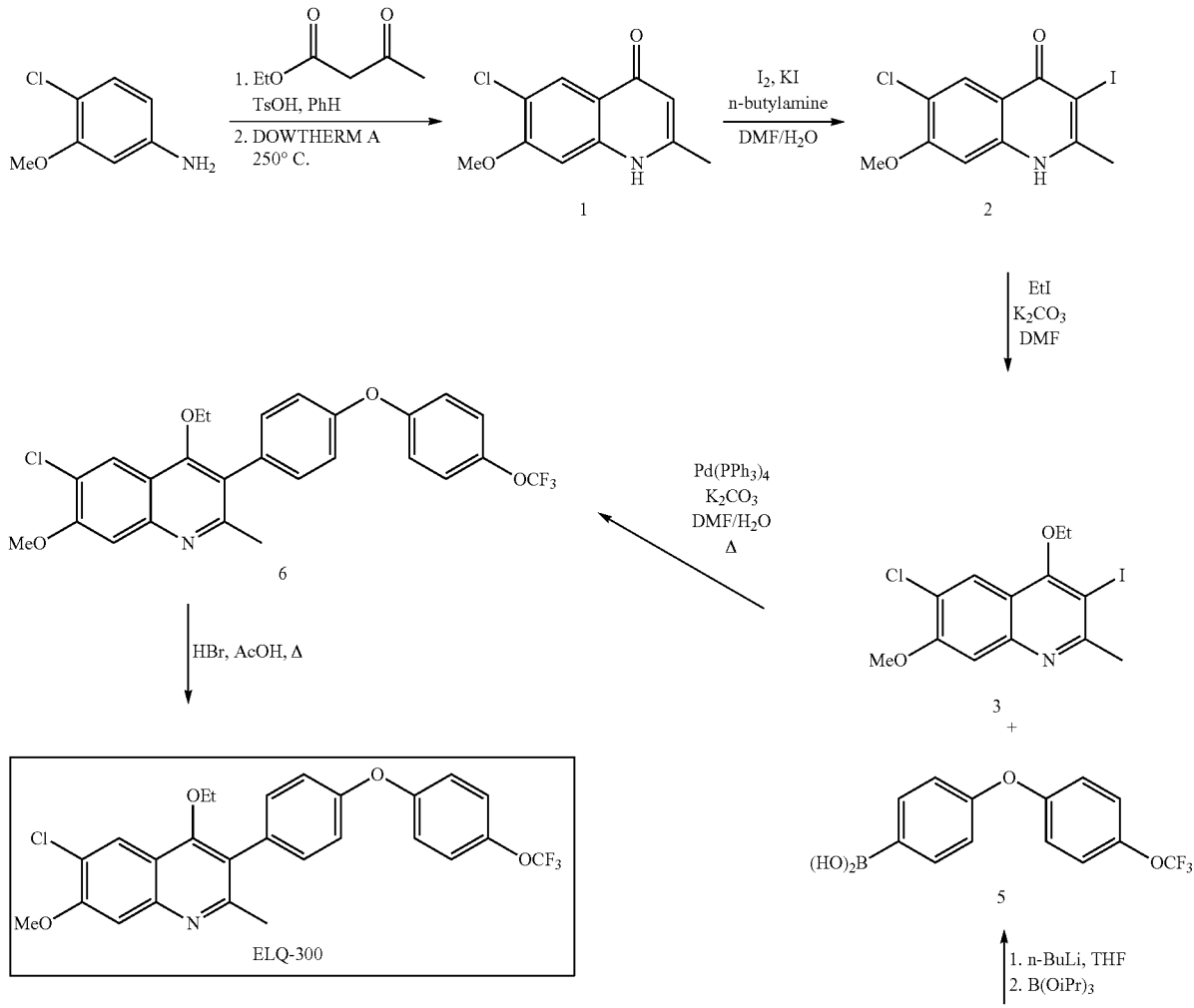

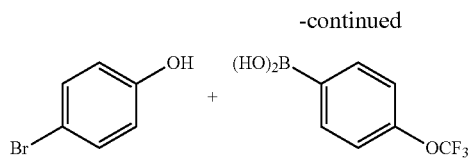

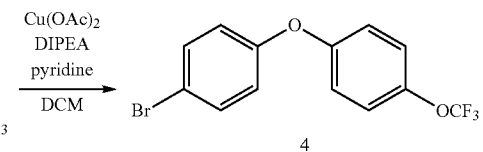

Condensation of 4-chloro-3-methoxy aniline and ethyl acetoacetate followed by thermal cyclization provided 2-methyl-4-quinolone 1 via Conrad-Limpach synthesis. Iodination of 1 with iodine in saturated aqueous potassium iodide solution and n-butylamine provided the 3-iodo-4-quinolone 2. Copper-mediated coupling of 4-bromophenol and 4-trifluoromethoxyphenyl boronic acid with Hunig's base and pyridine afforded the diaryl ether 4. Reaction of the lithium anion of 4 with boron triisopropoxide followed by acidic hydrolysis of the resulting boronic ester provided the boronic acid 5. Suzuki-Miyaura reaction of the 3-iodo-4-quinolone 2 with the boronic acid 5 resulted in difficult to separate mixtures of quinolone starting material and product. This difficulty in separation was likely the result of a combination of pi-stacking and intermolecular hydrogen bonding typical of 4-quinolones. A functional group protection strategy involving the 4-position alcohol was devised that would alleviate this problem by mitigating intermolecular hydrogen bonding. To this end 4-O-carbonates and 4-O-acetates were prepared, but these were found to be labile under Suzuki-Miyaura reaction conditions. A more robust protecting group, a 4-O-ethyl ether, was shown to be stable under these reaction conditions, yet reactive enough to be selectively removed in the presence of an aryl methoxy moiety. The 3-iodo-quinolone 2 was reacted with ethyl iodide and potassium carbonate to give the corresponding ethyl ether 3. Suzuki-Miyaura coupling of 3 with 4-phenoxyphenylboronic acid using palladium tetrakis triphenylphosphine and aqueous potassium carbonate provided 3 in very good yield. ELQ-300 was obtained in quantitative yield by heating the ethyl ether 3 in 30% hydrobromic acid in acetic acid.

Experimental

General. $^1$H NMR spectra were taken on a Varian 400 MHz instrument. Data reported were calibrated to internal TMS (0.0 ppm) for all solvents and are reported as follows: chemical shift, multiplicity (bs, broad singlet; s, singlet; d, doublet; t, triplet; q, quartet; and m, multiplet), coupling constant and integration. High-resolution mass spectrometry (HRMS) using electrospray ionization was performed by the PSU Bio-Analytical Mass Spectrometry Facility. Inert atmosphere operations were conducted under argon in flame-dried glassware. Anhydrous solvents and reagents were purchased from Sigma-Aldrich or Acros and were used without further purification. Final compounds were judged to be >95% pure by $^1$H NMR analysis.

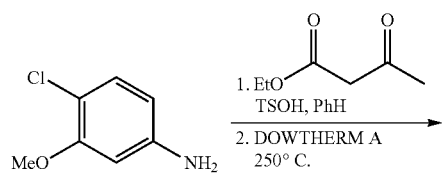

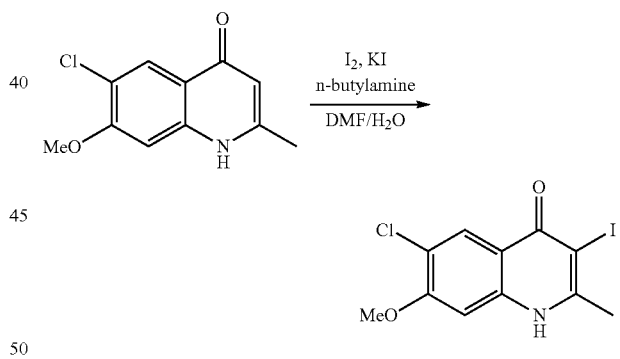

6-Chloro-7-methoxy-2-methylquinolin-4(1H)-one (1). A solution of 5-amino-2-chloroanisole (10.0 g, 63.5 mmol), ethyl acetoacetate (8.1 ml, 63.5 mmol) and catalytic para-toluene sulfonic acid (302 mg, 1.59 mmol) in 65 ml benzene over 4 A molecular sieves was stirred 6 hours at reflux (90° C. external temperature). The reaction mixture was then filtered and concentrated in vacuo. A mixture of the resulting residue and 6.4 ml DOWTHERM A was heated to 250° C. for 20 min. The reaction mixture was cooled to room temperature, and the precipitate was washed with hexanes and ethyl acetate to give 6.43 g (45% yield) of 6-chloro-7-methoxy-2-methylquinolin-4(1H)-one as a light brown solid. $^1$H NMR (400 MHz, DMSO-d6) δ 11.54 (bs, 1H), 7.94 (s, 1H), 7.02 (s, 1H), 5.86 (s, 1H), 3.94 (s, 3H), 2.31 (s, 3H).

6-chloro-3-iodo-7-methoxy-2-methylquinolin-4(1H)-one (2). To a stirred solution of 6-chloro-7-methoxy-2-methylquinolin-4(1H)-one (6.43 g, 28.7 mmol) and n-butylamine (28 ml, 287 mmol) in dimethylformamide (57 ml) cooled by a room temperature water bath was added iodine (7.30 g, 28.7 mmol) in a saturated solution of aqueous potassium iodide (29 ml). The reaction mixture was stirred 12 hours at room temperature. Residual iodine was quenched with 0.1 M aqueous sodium thiosulfate, and the resulting solution was concentrated in vacuo. The residue was resuspended in water and filtered to give 8.93 g (89% yield) of 6-chloro-3-iodo-7-methoxy-2-methylquinolin-4(1H)-one as a light brown powder. $^1$H NMR (400 MHz, DMSO-d6) δ 11.65 (bs, 1H), 7.59 (s, 1H), 6.41 (s, 1H), 3.91 (s, 3H), 2.18 (s, 3H).

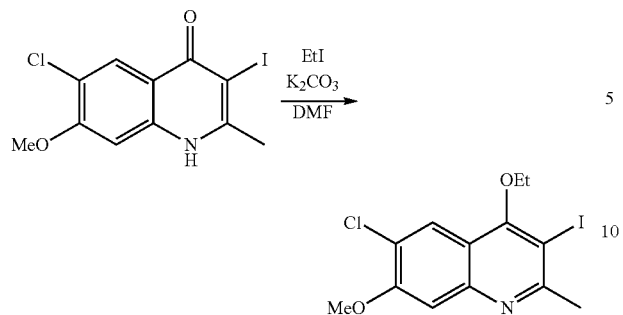

6-chloro-4-ethoxy-3-iodo-7-methoxy-2-methylquinoline (3). To a stirred solution of 6-chloro-3-iodo-7-methoxy-2-methylquinolin-4(1H)-one (2.00 g, 5.72 mmol) in dimethylformamide (57 ml) was added potassium carbonate (1.58 g, 11.4 mmol) at room temperature. The resulting suspension was stirred 0.5 hours at 50° C. Ethyl iodide was added dropwise at room temperature, and the reaction mixture was stirred 8 hours at 50° C. The solvent was removed in vacuo and the resulting residue was resuspended in ethyl acetate and water. The organic layer was extracted with brine, dried over magnesium sulfate and concentrated in vacuo to give 2.12 g (99% yield) of 6-chloro-4-ethoxy-3-iodo-7-methoxy-2-methylquinoline as a light brown solid. $^1$H NMR (400 MHz, CDCl$_3$) δ 7.99 (s, 1H), 7.40 (s, 1H), 4.19 (q, J=7.1 Hz, 2H), 4.02 (s, 3H), 2.92 (s, 3H), 1.61 (t, J=7.1 Hz, 3H).

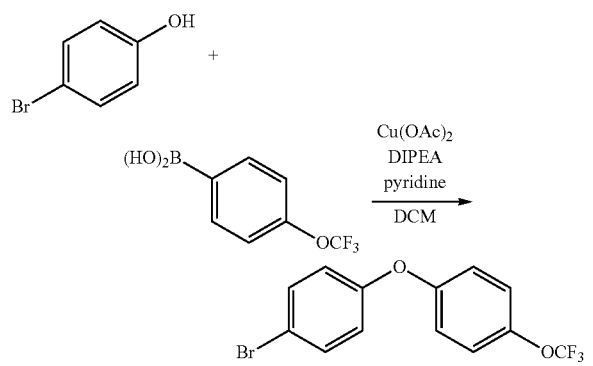

1-Bromo-4-(4-(trifluoromethoxy)phenoxy)benzene (4). To a solution of 4-(trifluoromethoxy)phenylboronic acid (10.0 g, 48.6 mmol) and 4-bromophenol (4.20 g, 24.3 mmol) in dichloromethane (250 ml) over 4 A molecular sieves was added copper (II) acetate (4.41 g, 24.3 mmol), diisopropylethylamine (21 ml, 121 mmol) and pyridine (10 ml, 121 mmol). The reaction mixture was stirred 12 hours at room temperature under positive pressure of dry air and concentrated in vacuo. The resulting residue was resuspended in ethyl acetate and 0.5 M HCl. The organic layer was extracted with water and brine, dried over magnesium sulfate and concentrated in vacuo. Purification by silica gel chromatography (ethyl acetate/hexanes) provided 5.07 g 1-bromo-4-(4-(trifluoromethoxy) phenoxy) benzene (63% yield) as a clear oil. $^1$H NMR (400 MHz, CDCl$_3$) δ 7.45 (d, J=9.3 Hz, 1H), 7.19 (d, J=8.9 Hz, 1H), 6.99 (d, J=9.3 Hz, 1H), 6.89 (d, J=8.9 Hz, 1H).

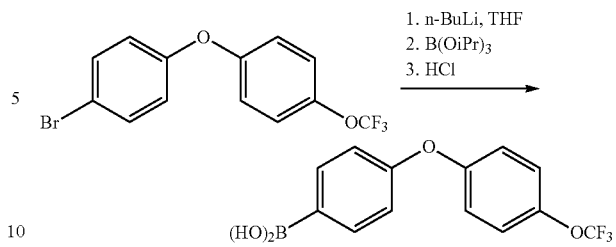

(4-(4-(Trifluoromethoxy)phenoxy)phenyl)boronic acid (5). To a solution of 1-bromo-4-(4-(trifluoromethoxy)phenoxy) benzene (5.07 g, 15.2 mmol) in THF (76 ml) at −78° C. was added n-butyllithium (7.6 ml, 2.5 M in hexanes, 19.0 mmol) dropwise. The reaction mixture was stirred 0.5 hours at −78° C., and triisopropylborate (7.0 ml, 30.4 mmol) was added. The reaction was stirred 4 hours at room temperature, quenched with 1 N HCl and stirred 0.5 hours at 0° C. The aqueous layer was extracted with ethyl acetate. The combined organic layers were extracted with brine and dried over magnesium sulfate. Purification by silica gel chromatography (0-10% methanol in dichloromethane) provided 4.38 g (4-(4-(trifluoromethoxy) phenoxy) phenyl) boronic acid (97% yield) as a light brown viscous oil. $^1$H NMR (400 MHz, CDCl$_3$) δ 8.20 (d, J=8.9 Hz, 1H), 7.26 (d, J=8.9 Hz, 1H), 7.07-7.14 (m, 2H).

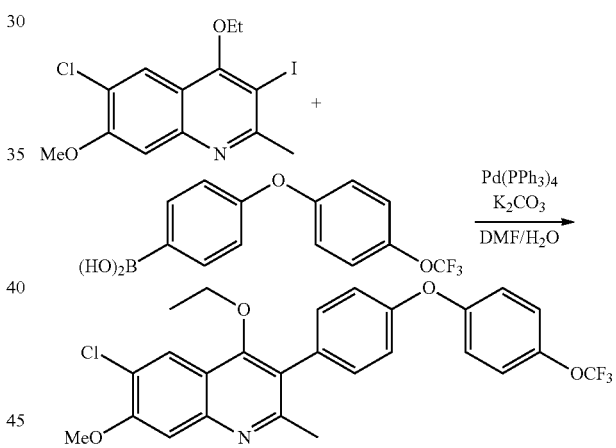

6-chloro-4-ethoxy-7-methoxy-2-methyl-3-(4-(4-(trifluoromethoxy)phenoxy) phenyl) quinoline (6). To a solution of 6-chloro-4-ethoxy-3-iodo-7-methoxy-2-methylquinoline (1.56 g, 4.13 mmol), (4-(4-(trifluoromethoxy)phenoxy) phenyl) boronic acid (1.85 g, 6.20 mmol) and palladium (0) tetrakis triphenylphosphine (239 mg, 0.207 mmol) in degassed dimethylformamide was added 8.25 ml of a 2 N aqueous potassium carbonate solution. The reaction mixture was stirred 18 hours at 85° C., filtered through celite and concentrated in vacuo. The resulting residue was resuspended in dichloromethane and water. The organic layer was extracted with brine, dried over magnesium sulfate and concentrated in vacuo. Purification by silica gel chromatography (0-20% ethyl acetate in dichloromethane) provided 1.18 g 6-chloro-4-ethoxy-7-methoxy-2-methyl-3-(4-(4-(trifluoromethoxy)phenoxy)phenyl)quinoline (57% yield) as a light brown solid. $^1$H NMR (400 MHz, CDCl$_3$) δ 8.11 (s, 1H), 7.43 (s, 1H), 7.31-7.36 (m, 2H), 7.22-7.26 (m, 2H), 7.07-7.14 (m, 4H), 4.04 (s, 3H), 3.71 (q, J=7.1 Hz, 2H), 2.49 (s, 3H), 1.18 (t, J=7.1 Hz, 3H).

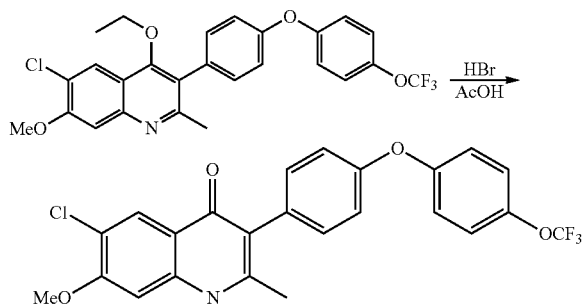

6-chloro-7-methoxy-2-methyl-3-(4-(4-(trifluoromethoxy) phenoxy)phenyl) quinolin-4(1H)-one (ELQ-300). To a solution of 6-chloro-4-ethoxy-7-methoxy-2-methyl-3-(4-(4-(trifluoromethoxy)phenoxy)phenyl)quinoline (1.16 g, 2.30 mmol) in acetic acid (10 ml) was added a 50% aqueous hydrobromic acid solution (5 ml). The reaction mixture was stirred 24 hours at 90° C., cooled and concentrated in vacuo. The resulting residue was resuspended in water, neutralized with 2 N NaOH and filtered. The collected solid was triturated with dichloromethane and filtered to provide 923 mg 6-chloro-7-methoxy-2-methyl-3-(4-(4-(trifluoromethoxy) phenoxy) phenyl) quinolin-4(1H)-one (84% yield) as a white powder. $^1$H NMR (400 MHz, CDCl$_3$) δ 11.97 (s, 1H), 8.05 (s, 1H), 7.42 (d, J=8.7 Hz, 2H), 7.29 (d, J=8.3 Hz, 2H), 7.17 (d, J=8.3 Hz, 2H), 7.12 (s, 1H), 7.08 (d, J=8.7 Hz, 2H), 3.97 (s, 3H), 2.26 (s, 3H). HRMS (EI+) m/z for C$_{24}$H$_{17}$ClF$_3$NO$_4$: calculated 475.0798, found 475.0801.

Preparation of 6-chloro-3-(2-fluoro-4-(4-(trifluoromethoxy)phenoxy)phenyl)-7-methoxy-2-methylquinolin-4(1H)-one [RMMC 391]

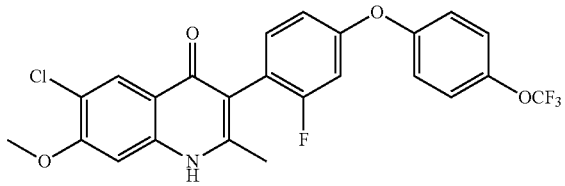 [SMILES: COc1cc2[nH]c(C)c(-c3ccc(Oc4ccc(OC(F)(F)F)cc4)cc3F)c(=O)c2cc1Cl]

An oven-dried Schlenk tube was flame-dried and backfilled with argon (X3). The tube was then charged with 6-chloro-4-ethoxy-3-(2-fluoro-4-(4-(trifluoromethoxy)phenoxy)phenyl)-7-methoxy-2-methylquinoline (0.3 g, 0.8 mmol), Pd(PPh$_3$)$_4$ (0.08 g, 10 mol %), and 2-fluoro-4-(4-(trifluoromethoxy)phenoxy)phenylboronic acid (0.375 g, 1.2 mmol). A rubber septum was then placed on the tube and 2M Na$_2$CO$_3$ (3 mL), DMF (15 mL), were added. The tube was then purged of air by argon for about 1 minute, while stirring and then heated at 90° C. until completion by HPLC analysis ~3 h. After completion, reaction was boiled with 1:1 MeOH/CHCl$_3$, and filtered over celite. The celite was then rinsed with boiling hot DMF. The filtrate was then evaporated on silica gel purified via flash chromatography (33% EtOAc in Hexane). The resulting amorphous solid (0.48 g, 52%) was then dissolved in 4.8 mL of AcOH and 4.8 mL of HBr. This solution was refluxed for 1.5 h. The reaction was poured onto ice and water. The resulting solid was filtered via filtration and recrystallized from DMF twice (0.2 g, 44%).

$^1$H NMR (400 MHz, DMSO) δ 11.79 (s, 1H), 7.99 (d, J=1.3 Hz, 1H), 7.44 (d, J=8.9 Hz, 2H), 7.29 (t, J=8.0 Hz, 1H), 7.23 (dd, J=9.0, 1.2 Hz, 2H), 7.08 (s, 1H), 6.99 (d, J=10.4 Hz, 1H), 6.90 (d, J=10.1 Hz, 1H), 3.97 (s, 3H), 2.20 (s, 3H). $^{13}$C NMR (101 MHz, CDCl$_3$) δ 173.09, 160.46 (d, J=246.6 Hz), 156.79, 156.66 (d, J=246.6 Hz), 154.87, 147.54, 144.07, 139.67, 134.22 (d, J=5.05 Hz), 126.03, 123.04, 120.43, 118.68 (d, J=17.17 Hz), 118.27 (d, J=16.16 Hz), 114.05, 113.93 (d, J=3.03 Hz), 106.13 (d, J=26.26 Hz), 99.51, 56.32, 18.24. $^{19}$F NMR (376 MHz, CDCl$_3$) δ −52.56, −105.28.

Preparation of 2-fluoro-4-(4-(trifluoromethoxy)phenoxy)phenylboronic acid

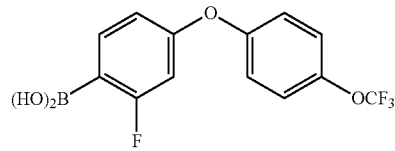 [SMILES: OB(O)c1ccc(Oc2ccc(OC(F)(F)F)cc2)cc1F]

4-(4-(trifluoromethoxy)phenoxy)phenylboronic acid (120). In a flame-dried 25 mL schlenk tube backfilled with argon (X3) a solution of 4-bromo-3-fluorophenol (0.346 g, 2 mmol) in N-methylpyrrolidine (8 mL) under an argon atmosphere was added 4-(trifluoromethoxy)iodobenzene (0.626 mL, 4 mmol), 2,2,6,6-tetramethylheptane-3,5-dione (0.092 mL, 0.44 mmol) and cesium carbonate (1.30 g, 4 mmol). The slurry was degassed by bubbling argon for 15 min and CuCl (0.099 g, 1 mmol) was then added. The reaction mixture was again degassed and then warmed to 100° C. for 7 h. After cooling to room temperature, Et$_2$O (75 mL) was added slowly. The resulting slurry was filtered and the solid washed with Et$_2$O (3×50 mL). The combined filtrates were washed with 2 M NaOH (100 mL), water (100 mL), 1 M aq HCl (100 mL), water (100 mL) and saturated brine (100 mL), the subsequently dried over Na2SO4 and concentrated under reduced pressure. The residue was purified via flash chromatography with 100% Hexane. This column was repeated three times combining the purest fractions each column to obtain pure material due to similarly eluting 4-(trifluoromethoxy) iodobenzene to afford 1-bromo-2-fluoro-4-(4-(trifluoromethoxy)phenoxy)benzene (0.15 g, 45%) as a colorless liquid. To a solution of 1-bromo-2-fluoro-4-(4-(trifluoromethoxy)phenoxy)benzene (2.1 mmol, 0.7 g) and triisopropyl borate (2.7 mmol, 0.63 mL) in dry THF (15 mL) at −78° C. was added dropwise 2.5M BuLi (6.5 mL) in Hexanes over 5 minutes. The reaction was stirred for 3 h at −78° C. at which point 10 mL of 6M HCl is added and the solution is allowed to warm up to room temperature and stir overnight. The reaction mixture was diluted with EtOAc (150 mL) and water (150 mL). The organic layer is taken separately and rinsed with water (150 mL), followed by brine (150 mL) and then dried over Na$_2$SO$_4$. The EtOAc is then concentrated in vacuo to afford a waxy solid which is then treated with 2M NaOH (40 mL) and stirred for 15 min diluted with water (300 mL) and stirred for 20 minutes. The solution is then filtered and the filtrate washed with hexane (3×100 mL). The aqueous layer was carefully acidified to pH 1 with 6 m HCl. The resulting white solid was filtered and dried on a high vacuum overnight to afford the titled compound in 67% yield.

$^1$H NMR (400 MHz, CDCl$_3$) δ 7.78 (t, J=8.1 Hz, 1H), 7.22 (d, J=9.0 Hz, 2H), 7.09-7.02 (m, 2H), 6.80 (dd, J=8.3, 2.2 Hz, 1H), 6.63 (dd, J=12.0, 2.2 Hz, 1H), 5.14 (d, J=6.3 Hz, 2H).

Parasites

*Plasmodium falciparum* strains D6 and Dd2 were obtained from the MR4 (ATCC, Manassas, Va., USA). D6 is sensitive to chloroquine but mildly resistant to mefloquine while Dd2 is resistant to multiple quinoline and antifolate antimalarial agents. Tm90.C2B is resistant to atovaquone, chloroquine, mefloquine, and quinine.

Parasite Culture and Drug Sensitivity

Three different laboratory strains of *P. falciparum* were cultured in human erythrocytes by standard methods under a low oxygen atmosphere (5% $O_2$, 5% $CO_2$, 90% $N_2$) in an environmental chamber as described in Trager, W., and J. B. Jensen. 1976. Human malaria parasites in continuous culture. Science 193:673-5. The culture medium was RPMI-1640, supplemented with 25 mM HEPES buffer, 25 mg/L gentamicin sulfate, 45 mg/L hypoxanthine, 10 mM glucose, 2 mM glutamine, and 0.5% Albumax II (complete medium). The parasites were maintained in fresh human erythrocytes suspended at a 2% hematocrit in complete medium at 37° C. Stock cultures were sub-passaged every 3 to 4 days by transfer of infected red cells to a flask containing complete medium and uninfected erythrocytes.

In vitro antimalarial activity of the compounds was assessed by the SYBR Green I fluorescence-based method (the "MSF assay") described previously by Smilkstein, M., N. Sriwilaijaroen, J. X. Kelly, P. Wilairat, and M. Riscoe. 2004. Simple and inexpensive fluorescence-based technique for high-throughput antimalarial drug screening. Antimicrob Agents Chemother 48:1803-6 with minor modifications (Winter, R. W., J. X. Kelly, M. J. Smilkstein, R. Dodean, G. C. Bagby, R. K. Rathbun, J. I. Levin, D. Hinrichs, and M. K. Riscoe. 2006. Evaluation and lead optimization of anti-malarial acridones. Exp Parasitol 114:47-56). Experiments were set up in triplicate in 96 well plates (Costar, Corning) with two-fold dilutions of each drug across the plate in a total volume of 100 microliters and at a final red blood cell concentration of 2% (v/v). Stock solutions of each drug were prepared by dissolving in ethanol or dimethylsulfoxide (as appropriate) at 10 mM. Each dilution series was initiated at a concentration of 1 µM and the experiment was repeated beginning with a lower initial concentration for those compounds in which the $IC_{50}$ value was below 10 nM. Automated pipeting and dilution was carried out with the aid of a programmable Precision 2000 robotic station (BioTek, Winooski, Vt.). An initial parasitemia of 0.2% was attained by addition of normal uninfected red cells to a stock culture of asynchronous parasite infected red cells (PRBC). The plates were incubated for 72 hrs at 37° C. in an atmosphere of 5% $CO_2$, 5% $O_2$, and 90% $N_2$. After this period the SYBR Green I dye-detergent mixture (100 µl) was added and the plates were incubated at room temperature for an hour in the dark and then placed in a 96-well fluorescence plate reader (Spectramax Gemini-EM, Molecular Diagnostics) for analysis with excitation and emission wavelength bands centered at 497 and 520 nm, respectively. The fluorescence readings were plotted against the logarithm of the drug concentration and curve fitting by nonlinear regression analysis (GraphPad Prism software) yielded the drug concentration that produced 50% of the observed decline relative to the maximum readings in drug-free control wells ($IC_{50}$).

In Vivo Efficacy in a Murine Malaria Model of Patent Infection with *P. yoelii*

The activity of the ester, ELQ-125, against the blood stages was assessed using a modified Thompson procedure (Arba Ager, 1984). Rodent malaria models, vol. 68/I. Springer-Verlag, Berlin. Mice (female, CF1) were infected intravenously with 1-5 million *P. yoelii* parasitized erythrocytes from a donor animal. Drug administration was initiated once the parasitemia had risen to between 3 to 5% as determined microscopically by examination of Giemsa-stained blood smears. The test compound, ELQ-125, was taken into NeoBee® M-5 (Stephan Company, Northfield, Ill., USA) and used without dilution. The drug was administered by gavage once daily for 3 days. On the $4^{th}$ day blood films were prepared and the extent of parasitemia was determined microscopically. $ED_{50}$ and $ED_{90}$ values (mg/kg/day) were derived from the dose required to reduce the parasite burden by 50% and 90%, respectively, relative to drug-free controls. The procedures involved, together with all matters relating to the care and housing of the animals used in this study, were approved by the Portland Va. Medical Center Institutional Animal Care and Use Committee (approval #0807).

Prodrugs containing a water-soluble pro-moiety that could be metabolically released after drug administration were designed and synthesized. A prodrug ester of ELQ-121 was synthesized and it was found that the prodrug formulation (ELQ-125) exhibits improved water solubility, miscibility with NeoBee M-5, a pharmaceutical delivery vehicle, and greatly enhanced in vivo efficacy. In a test of drug efficacy against a patent *P. yoelii* infection in mice with a ≈3-5% parasitemia (5 mice/group) at the beginning of a 3-day (once daily) treatment regimen, doses of 100 mg/kg/day and 50 mg/kg/day completely cleared parasites from the bloodstream without evident toxicity based on weight loss, grooming and locomotion. In each case, ELQ-125, a clear and colorless syrup, was administered orally with NeoBee M-5 (vol.=100 µl). At 25 mg/kg/day, parasitemia was suppressed by >99% relative to controls (assessed on the day following the last dose) and the animals in this group remained parasite-free until they were euthanized 10 days later. A follow-up study in which the drug was administered in 100 µl NeoBee M5 established $ED_{90}$ (22 mg/kg/day) and $ED_{50}$ (11 mg/kg/day) values for ELQ-125 in the same mouse system.

Although not bound by any theory, it is believed that these results have great significance. The poly-ethylene glycol (PEG) promoiety, a "first-of-a-kind" construct, proved to be highly efficacious by oral dosing. Taken together with other enhancements incorporated into the pharmacophore, at least two major obstacles (enhanced solubility and metabolic stability) have been overcome that have blocked the therapeutic advancement of endochin for over 60 years. In addition, by introducing chemical features into the 4(1H)-quinolone core that enhance aqueous solubility without compromising antiparasitic activity or metabolic stability, quinolones can be designed that are efficacious and curative without the promoiety.

In vitro Activity and Pharmaco-Resistance Pattern of Quinolones Against a Panel of *P. Falciparum* Parasites The compounds were screened for antiplasmodial activity in vitro against chloroquine (CQ) sensitive (D6), multidrug resistant (Dd2), and chloroquine/quinine/atovaquone (ATV)-resistant (Tm90.C2B) strains of *P. falciparum*. The compound structures and results are provided in Table 1 (FIG. 4). It may be observed that endochin (ELQ-100) exhibits potent activity with $IC_{50}$ values of ≈3-4 nM vs. D6 and Dd2, and 11.4 nM vs. the ATV-resistant Tm90.C2B clinical isolate, i.e., a modest level of ATV cross-resistance. Exploration of the structure-activity relationships revealed that the potency of the endochin molecule can be greatly influenced by chemical modification. The following observations on the structure-activity relationships (SAR) can be made:

1. It may be observed that the length of the 3-position side chain influences the antiplasmodial effect. Our data show that the 7 carbon chain length (endochin) is superior to C6>C5>C4 with values ranging from ≈3 nM (ELQ-100) to ≈30 nM (C4, ELQ-115). ELQ-103 with a trifluoroundecyl side chain exhibits $IC_{50}$ values in the low nanomolar range for all 3 tested strains.

2. Replacement of the 7-$OCH_3$ group by hydroxy (ELQ-117) greatly diminishes antiplasmodial activity whereas replacement by either Cl (ELQ-109) or F (ELQ-120) results in only a modest reduction in in vitro potency. Derivatives bearing other electronegative substituents at the 7-position (e.g., CN, $CF_3$, $OCF_3$, and $NO_2$) proved inferior, and all of these molecules exhibited modest to significant cross-resistance against the Tm90.C2B strain. It is interesting that the in vitro activity of the 7-H analog (ELQ-127) is weakened by roughly 5-fold relative to that of endochin however it remains equally active against all three parasite strains.

3. In certain embodiment, the 2-$CH_3$ group may be important because replacement of it with a hydroxy is accompanied by a dramatic loss of effectiveness, e.g., compare ELQ-100 to ELQ-106 vs. the D6 strain with $IC_{50}$ values of 3.8 nM and >2,500 nM, respectively.

4. Moving the chlorine atom from the 7 position (e.g., ELQ-109) to the 6-position (e.g., ELQ-130) results in a modest reduction in antimalarial response (strain D6 $IC_{50}$ values of 5.8 nM and 22.2 nM, respectively) however equal sensitivity is observed against the atovaquone-resistant Tm90.C2B clinical isolate only for ELQ-130. Similar results were observed for the congener with a fluorine atom at position 6 (ELQ-131). Taken together with results from the 7-H derivative, ELQ-127, these observations combine to suggest that the mutation appearing in the cytochrome b gene of this clinical isolate (which is linked to a high level of atovaquone resistance) introduces steric hindrance to bulky substituents occupying the 7-position of quinolone ring system.

5. Placement of 2 halogens on the benzenoid ring had a mixed effect. The 5,7-dichloro endochin analog (ELQ-124) exhibited weak in vitro activity while the corresponding 5,7-difluoro construct (ELQ-121) proved to be one of the most potent compounds in the tested series with $IC_{50}$ values of ≈0.05 nM against D6 and Dd2 and about 300 times higher against Tm90.C2B. By contrast, the 6,8-difluoro positional isomer was vastly inferior with $IC_{50}$ values ranging from ≈110 nM to 134 nM for all 3 strains, i.e., potency was diminished by ≈2.000-fold.

6. Particularly revealing are the results of testing ELQ-134 and ELQ-119, structural analogs of the most potent quinolone construct. ELQ-134 is the N-methyl derivative of ELQ-121 and it shows greatly diminished potency (roughly 300-fold reduced); its metabolic stability will be evaluated. ELQ-119 contains a chlorine atom at the 4-position and it is over a 1,000 times less potent than the parent drug based on in vitro testing.

Determination of anti-*T. gondii* $IC_{50}$ and $TD_{50}$ values—use of the 2F strain. This method, which employs tachyzoites of *Toxoplasma gondii* strain 2F that constitutively expresses cytoplasmic Beta-galactosidase, has been described recently by Jones-Brando et al. (Jones-Brando, L., D'angelo, J., Posner, G H, and Yolken, R., 2006, In vitro inhibition of *Toxoplasma gondii* by four new derivatives of artemisinin, *Antimicrobial Agents and Chemotherapy* 50: 4206-8). The compounds disclosed herein were examined at concentrations ranging from 0 to 320 μM; the initial test range is from 10 nM to 320 μM and if necessary a follow-up test was conducted in a lower concentration range sufficient to bracket the $IC_{50}$. Briefly, each drug was dissolved in ethanol or DMSO, as appropriate, at a concentration of 10 mM and diluted with complete Dulbecco's modified Eagle's medium (DMEM) to 1,000 μM. Test and control drugs were added to human foreskin fibroblasts (HFF) cells that were grown overnight in 96-well plates in DMEM containing 10% fetal calf serum. On the following day the culture medium was replaced with DMEM containing 1% fetal calf serum. After drug addition, 50 *T. gondii* tachyzoites were then added to each well and the plates were incubated at 37° C. in a humidified atmosphere with supplemental 5% $CO_2$. After 96 hrs the substrate for beta-galactosidase, chlorophenolred-beta-D-galactopyranoside (CPRG), was added and the plates were incubated for another 24 hr. After this period, Triton X-100 is added to inactivate the parasite and the color reactions in the wells were read in a microplate reader. The data were analyzed as detailed below. For anti-*T. gondii* $IC_{50}$ determinations, the plates are read at 570-650 nm. The amount of absorbance (570-650 nm) in wells containing drug, parasites, and CPRG reagent is compared to that in control wells containing *T. gondii*, HFF cells and CPRG. The amount of absorbance in these wells is directly proportional to the amount of beta-galactosidase activity and thus correlative to the number of viable tachyzoites in each well. Thus, a decrease in the amount of absorbance indicates an inhibition of parasite growth. Percent inhibition is calculated for each drug concentration and then the median inhibitory concentration reducing parasite growth by 50% relative to no-drug controls ($IC_{50}$) is calculated by extrapolation of the dose-response curve on a log-linear plot employing the portions of the curve that transect the 50% response point. Cytotoxicity induced by each ELQ against HFF cells is determined by use of the CellTiter 96 Aqueous One Reagent (Promega) yielding $TD_{50}$ (median cytotoxic dose) values calculated in the same manner as the $IC_{50}$. The primary goal of the drug testing studies is the determination of the median inhibitory ($IC_{50}$) and cytotoxic ($TD_{50}$) concentrations. The ratio of the $TD_{50}/IC_{50}$ is used to generate the the in vitro therapeutic index (IVTI), a measure of selectivity, for each compound.

Figure 5:
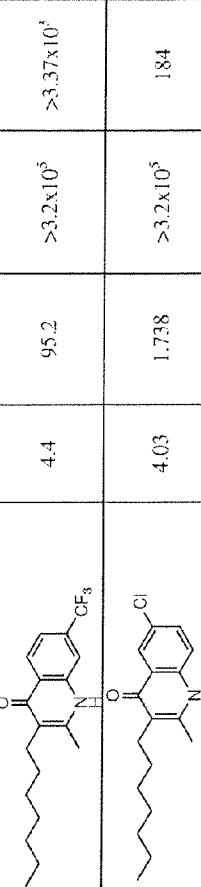
FIG. 5 is a table listing compounds and their activity against *Toxoplasma gondii* in vitro.

The compounds and results are shown in Table 2 (FIG. 5). In summary of our findings of the structure-activity profiles of endochin-like quinolones (ELQs) as antitoxoplasmic agents, we observe essentially the same correlation as observed for *Plasmodium falciparum* except that the N-alkyl derivatives (e.g., ELQ-134) exhibit enhanced growth inhibitory activity against *Toxoplasma gondii*.

Several embodiments of the compounds, composition and method disclosed herein are described below with reference to the following numbered paragraphs:

1. A compound of formula I:

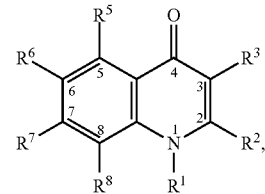

or formula II:

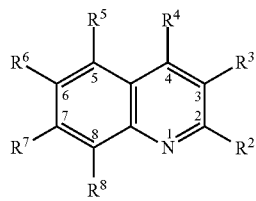

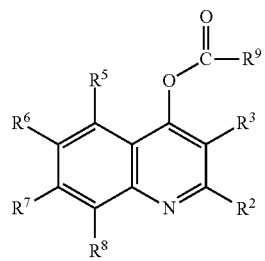

or a pharmaceutically acceptable salt of formula I or formula II, wherein:

$R^1$ is H, hydroxyl, alkoxy, acyl, alkyl, cycloalkyl, aryl, or heteroaryl;

$R^2$ is methyl, haloalkyl, or heteroaryl;

$R^4$ is hydroxyl, carbonyloxy, or carbonyldioxy;

$R^3$ is aliphatic, aryl, aralkyl, or alkylaryl; and $R^5$, $R^6$, $R^7$ and $R^8$ are each individually H, halogen, alkoxy, alkyl, haloalkyl, aryl, nitro, cyano, amino, amido, acyl, carboxyl, substituted carboxyl, or —$SO_2R^{10}$, wherein $R^{10}$ is H, alkyl, amino or haloalkyl;

provided that in formula I, $R^5$ and $R^7$ are not both H or $R^6$ is not H or methoxy; and in formula II that if $R^4$ is carbonyldioxy then $R^7$ is not methoxy.

2. The compound of paragraph 1, wherein $R^5$ and $R^7$ of formula I or II are each halogen or haloalkyl.

3. The compound of paragraph 1, wherein $R^5$ and $R^7$ of formula I or II are each F.

4. The compound of any one of paragraphs 1 to 3, wherein $R^4$ is carbonyloxy or carbonyldioxy.

5. The compound of any one of paragraphs 1 to 4, wherein $R^7$ of formula I or II is not methoxy.

6. The compound of any one of paragraphs 1 to 5, wherein $R^6$ of formula I or II is halogen and $R^5$ and $R^7$ are each H.

7. The compound of any one of paragraphs 1 to 6, wherein $R^2$ of formula I or II is methyl.

8. The compound of any one of paragraphs 1 to 7, wherein $R^3$ of formula I or II is a branched alkyl, linear alkyl, cycloalkyl, alkoxy, branched alkenyl, linear alkenyl or cycloalkenyl.

9. The compound of paragraph 8, wherein the branched or linear alkyl or branched or linear alkenyl is substituted at its terminal end with one or more fluorine atoms.

10. The compound of any one of paragraphs 1 to 9, wherein $R^1$ is H, alkyl, or cycloalkyl.

11. The compound of any one of paragraphs 1 to 9, wherein $R^1$ is alkyl.

12. The compound of paragraph 1, wherein in formula I:
$R^1$ is H or alkyl;
$R^2$ is methyl;
$R^5$ and $R^7$ are each F; and
$R^6$ and $R^8$ are each H.

13. The compound of paragraph 1, wherein in formula I:
$R^1$ is H or alkyl;
$R^2$ is methyl;
$R^5$, $R^7$ and $R^8$ are each H; and
$R^6$ is halogen.

14. The compound of any one of paragraphs 1 to 13, wherein $R^8$ of formula I or II is H.

15. The compound of any one of paragraphs 1 to 11 or 14, wherein the compound of formula II has a structure represented by formula III:

wherein $R^9$ is alkyl, alkenyl, alkyl amino, amido, aminocarbonyl, hydroxyalkyl, alkoxyalkyl or alkyl ether.

16. The compound of any one of paragraphs 1 to 11 or 14, wherein the compound of formula II has a structure represented by formula IV:

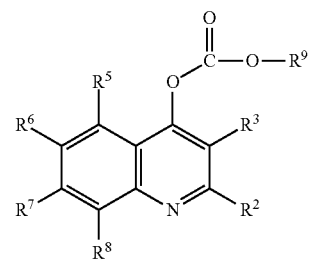

wherein $R^9$ is alkyl, alkenyl, alkyl amino, amido, aminocarbonyl, hydroxyalkyl, alkoxyalkyl or alkyl ether.

17. The compound of any of paragraphs 1 to 7 or 10 to 16, wherein $R^3$ is cycloalkyl, hetero-cycloalkyl, aliphatic ether, trifluoromethoxy-aliphatic ether, arahaloalkyl, trifluoromethoxy-diarylether, alkyl-heteroaryl, or alkyl-halogenated heteroaryl.

18. The compound of any one of paragraphs 1 to 7 or 10 to 16, wherein $R^3$ is a cycloalkyl, heterocycloalkyl, or heteroaryl.

19. The compound of paragraph 18, wherein $R^3$ is

Formula V

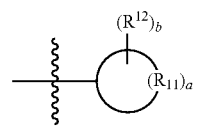

wherein $R^{11}$ is C or a heteroatom that may be at any position on the ring; a is 3 to 6; $R^{12}$ is selected from at least one of alkoxy, halogen-substituted alkoxy, halogenated lower alkyl, alkyl, methylsulfonyl, or halogen; and b is 0 to 5.

20. The compound of any one of paragraphs 1 to 7 or 10 to 16, wherein $R^3$ is an alkynyl.

21. The compound of paragraph 20, wherein $R^3$ is

Formula VIII

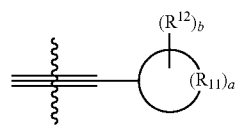

wherein $R^{11}$ is C or a heteroatom that may be at any position on the ring; a is 3 to 6; $R^{12}$ is selected from at least one of alkoxy, halogen-substituted alkoxy, halogenated lower alkyl, alkyl, methylsulfonyl, or halogen; and b is 0 to 5.

22. The compound of any one of paragraphs 1 to 7 or 10 to 16, wherein $R^3$ is a diaryl ether.

23. The compound of paragraph 22, wherein $R^3$ is

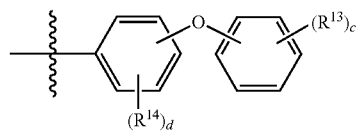

Formula X wherein $R^{13}$ and $R^{14}$ are each individually selected from at least one of alkoxy, halogen-substituted alkoxy, halogenated lower alkyl, alkyl, methylsulfonyl, or halogen; c is 0 to 5; and d is 0 to 5.

24. The compound of paragraph 1, wherein $R^1$ is H; $R^2$ is H or methyl; $R^3$ is cycloalkyl, heterocycloalkyl, heteroaryl, alkynyl or diaryl ether; $R^6$ is halogen; $R^7$ is H or methoxy; and $R^5$ and $R^8$ are each H.

25. A compound of formula XI:

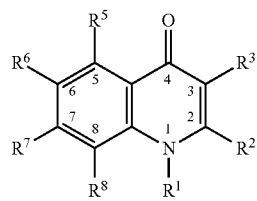

or a pharmaceutically acceptable salt of formula XI, wherein:

$R^1$ is H, hydroxyl, alkoxy, acyl, alkyl, cycloalkyl, aryl, or heteroaryl;

$R^2$ is H, carboxyl, substituted carboxyl, alkyl, haloalkyl, or heteroaryl;

$R^5$, $R^6$, $R^7$ and $R^8$ are each individually H, halogen, alkoxy, alkyl, haloalkyl, aryl, nitro, cyano, amino, amido, acyl, carboxyl, substituted carboxyl, or —$SO_2R^{10}$, wherein $R^{10}$ is H, alkyl, amino or haloalkyl; and $R^3$ is an optionally substituted cycloalkyl, an optionally substituted heterocycloalkyl, an optionally substituted heteroaryl, an optionally substituted alkynyl or an optionally substituted diaryl ether.

26. The compound of paragraph 25, wherein $R^1$ is H; $R^2$ is H or methyl; $R^6$ is halogen; $R^7$ is H or methoxy; and $R^5$ and $R^8$ are each H.

27. A composition comprising a pharmacologically active amount of at least one compound of any one of paragraphs 1 to 26 or a pharmaceutically acceptable salt thereof, and at least one pharmaceutically acceptable carrier.

28. A method for inhibiting a parasitic or infectious disease in a subject comprising administering to the subject a therapeutically effective amount of a compound of any one of paragraphs 1 to 26 or a pharmaceutically acceptable salt thereof.

29. The method of paragraph 28, wherein the parasitic disease is malaria.

30. The method of paragraph 29, wherein the malaria is multidrug-resistant malaria.

31. The method of paragraph 29, wherein the malaria is chloroquine-resistant malaria.

32. The method of paragraph 29, wherein the compound exhibits equipotency against chloroquine-resistant and multidrug-resistant strains of *Plasmodium* parasites.

33. The method of any one of paragraphs 28 to 32, wherein the compound of any one of paragraphs 1 to 26 is co-administered with at least one other antimalarial agent.

34. A method for inhibiting a parasitic disease in a subject comprising administering to the subject a therapeutically effective amount of a composition of paragraph 27.

35. The method of any one of paragraphs 28 to 34, wherein the method comprises prophylactic treating the subject against chloroquine-resistant or multidrug-resistant malaria.

36. The method of paragraph 28, wherein the parasitic disease is toxoplasmosis.

In view of the many possible embodiments to which the principles of the disclosed compounds and methods may be applied, it should be recognized that the illustrated embodiments are only preferred examples and should not be taken as limiting the scope of the invention.

What is claimed is:

1. A method for inhibiting malaria or toxoplasmosis in a subject comprising administering to the subject a therapeutically effective amount of a compound of formula I:

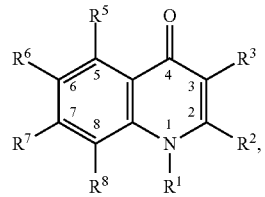

or formula II:

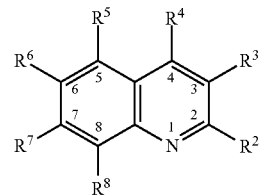

or a pharmaceutically acceptable salt of formula I or formula II, wherein:

$R^1$ is H, hydroxyl, alkoxy, acyl, alkyl, cycloalkyl, aryl, or heteroaryl;

$R^2$ is methyl, haloalkyl, or heteroaryl;

$R^4$ is carbonyloxy, or carbonyldioxy;

$R^3$ is diarly ether; and $R^5$ and $R^7$ are each individually H, halogen, alkoxy, alkyl, haloalkyl, aryl, nitro, cyano, amino, amido, acyl, carboxyl, substituted carboxyl, or —$SO_2R^{10}$, wherein $R^{10}$ is H, alkyl, amino or haloalkyl;

$R^6$ is H, halogen, alkoxy, alkyl, haloalkyl, aryl, cyano, amino, amido, acyl, carboxyl, substituted carboxyl, or —$SO_2R^{10}$, wherein $R^{10}$ is H, alkyl, amino or haloalkyl; and $R^8$ is H, halogen, alkoxy, haloalkyl, aryl, nitro, cyano, amino, amido, acyl, carboxyl, substituted carboxyl, or —$SO_2R^{10}$, wherein $R^{10}$ is H, alkyl, amino or haloalkyl;

provided that in formula I, $R^6$ is not H or methoxy; and in formula II that if $R^4$ is carbonyldioxy, then $R^7$ is not methoxy.

2. The method of claim 1, wherein $R^5$ and $R^7$ of formula I or II are each halogen or haloalkyl.

3. The method of claim 1, wherein $R^4$ is carbonyloxy or carbonyldioxy.

4. The method of claim 1, wherein $R^2$ of formula I or II is methyl.

5. The method of claim 1, wherein $R^1$ is H, alkyl, or cycloalkyl.

6. The method of claim 1, wherein the compound of formula II has a structure represented by formula III:

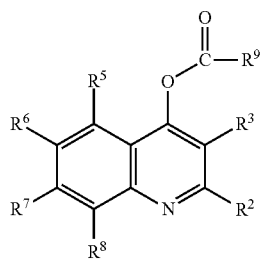

wherein $R^9$ is alkyl, alkenyl, alkyl amino, amido, aminocarbonyl, hydroxyalkyl, alkoxyalkyl or alkyl ether.

7. The method of claim 1, wherein the compound of formula II has a structure represented by formula IV:

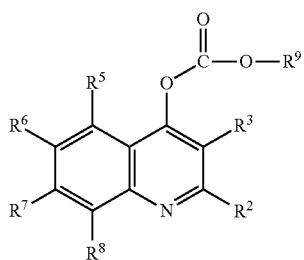

wherein $R^9$ is alkyl, alkenyl, alkyl amino, amido, aminocarbonyl, hydroxyalkyl, alkoxyalkyl or alkyl ether.

8. The method of claim 1, wherein the compound is a compound of formula I; and $R^3$ is trifluoromethoxy-diarylether.

9. The method of claim 8, wherein $R^7$ is methoxy.

10. The method of claim 8, wherein $R^6$ is halogen.

11. The method of claim 1, wherein $R^3$ is

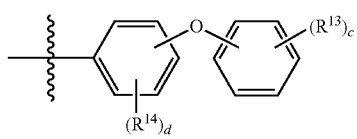

Formula X wherein $R^{13}$ and $R^{14}$ are each individually selected from at least one of alkoxy, halogen-substituted alkoxy, halogenated lower alkyl, alkyl, methylsulfonyl, or halogen; c is 0 to 5; and d is 0 to 5.

12. The method of claim 1, wherein $R^1$ is H; $R^2$ is methyl; $R^6$ is halogen; $R^7$ is H or methoxy; and $R^5$ and $R^8$ are each H.

13. The method of claim 1, wherein the compound is a compound, or a pharmaceutically acceptable salt thereof, having a structure of:

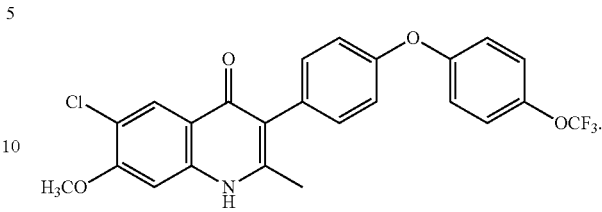

14. The method of claim 1, wherein the compound is a compound, or a pharmaceutically acceptable salt thereof, having a structure of:

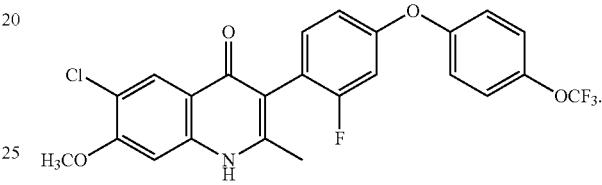

15. The method of claim 1, wherein the compound is a compound of claim 1, or a pharmaceutically acceptable salt thereof, having a structure of:

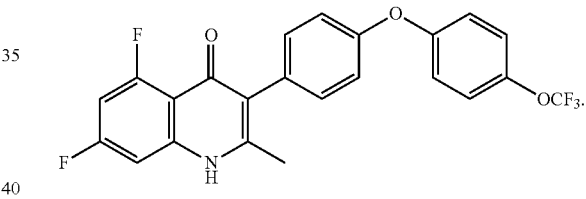

16. The method of claim 1, wherein the method inhibits malaria.

17. The method of claim 16, wherein the malaria is multi-drug-resistant malaria.

18. The method of claim 16, wherein the malaria is chloroquine-resistant malaria.

19. The method of claim 16, wherein the compound exhibits equipotency against chloroquine-resistant and multidrug-resistant strains of *Plasmodium* parasites.

20. The method of claim 16, wherein the compound is co-administered with at least one other antimalarial agent.

21. The method of claim 1, wherein the method comprises prophylactic treating the subject against chloroquine-resistant or multidrug-resistant malaria.

22. The method of claim 1, wherein the method inhibits toxoplasmosis.

23. The method of claim 13, wherein the method inhibits malaria.

24. The method of claim 14, wherein the method inhibits malaria.

25. A method for inhibiting malaria or toxoplasmosis in a subject comprising administering to the subject a therapeutically effective amount of a compound of formula XI:

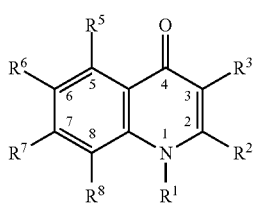

or a pharmaceutically acceptable salt of formula XI, wherein:
$R^1$ is H, hydroxyl, alkoxy, acyl, alkyl, cycloalkyl, aryl, or heteroaryl;
$R^2$ is H, carboxyl, substituted carboxyl, alkyl, haloalkyl, or heteroaryl;
$R^5$, $R^7$ and $R^8$ are each individually H, halogen, alkoxy, alkyl, haloalkyl, aryl, nitro, cyano, amino, amido, acyl, carboxyl, substituted carboxyl, or —$SO_2R^{10}$, wherein $R^{10}$ is H, alkyl, amino or haloalkyl;
$R^6$ is halogen: and
$R^3$ is an optionally substituted heteroaryl, an optionally substituted alkynyl or an optionally substituted diaryl ether.

26. The method of claim 25, wherein $R^1$ is H; $R^2$ is H or methyl; $R^7$ is H or methoxy; and $R^5$ and $R^8$ are each H.

27. The method of claim 25, wherein $R^3$ is

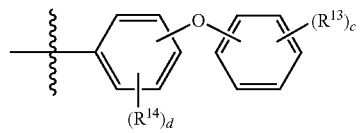

Formula X wherein $R^{13}$ and $R^{14}$ are each individually selected from at least one of alkoxy, halogen-substituted alkoxy, halogenated lower alkyl, alkyl, methylsulfonyl, or halogen; c is 0 to 5; and d is 0 to 5.

28. The method of claim 27, wherein the method inhibits malaria.

29. A method for inhibiting malaria or toxoplasmosis in a subject comprising administering to the subject a therapeutically effective amount of A compound of formula I:

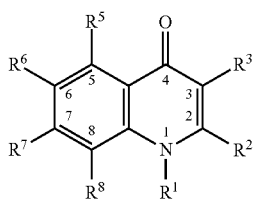

or a pharmaceutically acceptable salt of formula I, wherein:
$R^1$ is H, hydroxyl, alkoxy, acyl, alkyl, cycloalkyl, aryl, or heteroaryl;
$R^2$ is methyl, haloalkyl, or heteroaryl;
$R^3$ is trifluoromethoxy-diarylether; and
$R^5$, $R^6$, and $R^7$ and $R^8$ are each individually H, halogen, alkoxy, alkyl, haloalkyl, aryl, nitro, cyano, amino, amido, acyl, carboxyl, substituted carboxyl, or —$SO_2R^{10}$, wherein $R^{10}$ is H, alkyl, amino or haloalkyl;
provided that in formula I, $R^5$ and $R^7$ are not both H or $R^6$ is not H or methoxy.

30. A method for inhibiting malaria or toxoplasmosis in a subject comprising administering to the subject a therapeutically effective amount of a compound of formula I:

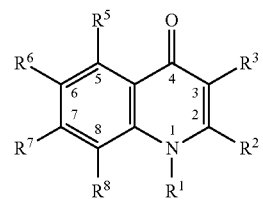

or a pharmaceutically acceptable salt of formula I, wherein:
$R^1$ is H, hydroxyl, alkoxy, acyl, alkyl, cycloalkyl, aryl, or heteroaryl;
$R^2$ is methyl, haloalkyl, or heteroaryl;
$R^3$ is

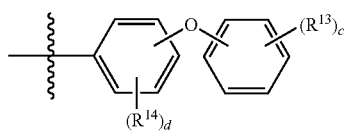

Formula X wherein $R^{13}$ and $R^{14}$ are each individually selected from at least one of alkoxy, halogen-substituted alkoxy, halogenated lower alkyl, alkyl, methylsulfonyl, or halogen; c is 0 to 5; and d is 0 to 5; and
$R^5$, $R^6$, and $R^7$ and $R^8$ are each individually H, halogen, alkoxy, alkyl, haloalkyl, aryl, nitro, cyano, amino, amido, acyl, carboxyl, substituted carboxyl, or —$SO_2R^{10}$, wherein $R^{10}$ is H, alkyl, amino or haloalkyl;
provided that in formula I, $R^5$ and $R^7$ are not both H or $R^6$ is not H or methoxy.

31. A method for inhibiting malaria or toxoplasmosis in a subject comprising administering to the subject a therapeutically effective amount of a compound of formula I:

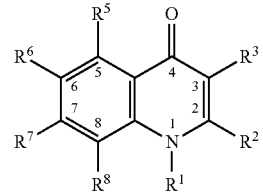

or a pharmaceutically acceptable salt of formula I, wherein:
$R^1$ is H, hydroxyl, alkoxy, acyl, alkyl, cycloalkyl, aryl, or heteroaryl;
$R^2$ is methyl, haloalkyl, or heteroaryl;
$R^3$ is trifluoromethoxy-diarylether; and
$R^5$ and $R^7$ are each individually H, halogen, alkoxy, alkyl, haloalkyl, aryl, nitro, cyano, amino, amido, acyl, carboxyl, substituted carboxyl, or —$SO_2R^{10}$, wherein $R^{10}$ is H, alkyl, amino or haloalkyl;
$R^6$ is H, halogen, alkoxy, alkyl, haloalkyl, aryl, cyano, amino, amido, acyl, carboxyl, substituted carboxyl, or —$SO_2R^{10}$, wherein $R^{10}$ is H, alkyl, amino or haloalkyl; and $R^8$ is H, halogen, alkoxy, haloalkyl, aryl, nitro, cyano, amino, amido, acyl, carboxyl, substituted carboxyl, or —$SO_2R^{10}$, wherein $R^{10}$ is H, alkyl, amino or haloalkyl; provided that in formula I, $R^6$ is not H or methoxy.

* * * * *